US012655446B2

(12) United States Patent　　　　(10) Patent No.: US 12,655,446 B2
Rivella et al.　　　　　　　　　　　(45) Date of Patent: Jun. 16, 2026

(54) COMPOSITIONS AND METHODS FOR HEMOGLOBIN PRODUCTION

(71) Applicant: The Children's Hospital of Philadelphia, Philadelphia, PA (US)

(72) Inventors: Stefano Rivella, Philadelphia, PA (US); Laura Breda, Philadelphia, PA (US); Alisa Dong, Glendale, CA (US); Silvia Pires Lourenco, Philadelphia, PA (US); Amaliris Gonzalez, Philadelphia, PA (US)

(73) Assignee: THE CHILDREN'S HOSPITAL OF PHILADELPHIA, Philadephia (PA)

( * ) Notice: Subject to any disclaimer, the term of this patent is extended or adjusted under 35 U.S.C. 154(b) by 557 days.

(21) Appl. No.: 17/049,061

(22) PCT Filed: Apr. 30, 2019

(86) PCT No.: PCT/US2019/029787
§ 371 (c)(1),
(2) Date: Oct. 20, 2020

(87) PCT Pub. No.: WO2019/213011
PCT Pub. Date: Nov. 7, 2019

(65) Prior Publication Data
US 2023/0287449 A1　　Sep. 14, 2023

Related U.S. Application Data

(60) Provisional application No. 62/664,788, filed on Apr. 30, 2018.

(51) Int. Cl.
| | |
|---|---|
| *C12N 15/86* | (2006.01) |
| *A61P 7/00* | (2006.01) |
| *C07K 14/805* | (2006.01) |
| *C12N 15/113* | (2010.01) |
| *C12N 15/867* | (2006.01) |

(52) U.S. Cl.
CPC .............. *C12N 15/86* (2013.01); *A61P 7/00* (2018.01); *C07K 14/805* (2013.01); *C12N 15/113* (2013.01); *C12N 15/867* (2013.01); *C12N 2740/16043* (2013.01); *C12N 2830/48* (2013.01); *C12N 2830/50* (2013.01)

(58) Field of Classification Search
CPC .... C12N 15/86; C12N 15/113; C12N 15/867; C12N 2740/16043; C12N 2830/48; C12N 2830/50; A61P 7/00; C07K 14/805
See application file for complete search history.

(56) References Cited

U.S. PATENT DOCUMENTS

| | | | | |
|---|---|---|---|---|
| 7,541,179 | B2 * | 6/2009 | Sadelain | C12N 15/86 |
| | | | | 435/320.1 |
| 7,901,671 | B2 | 3/2011 | Leboulch et al. | |
| 8,058,061 | B2 * | 11/2011 | Sadelain | A61P 7/06 |
| | | | | 435/325 |
| 9,068,199 | B2 | 6/2015 | Leboulch et al. | |
| 11,311,632 | B2 * | 4/2022 | Rivella | A61P 7/06 |
| 2003/0022303 | A1 | 1/2003 | Sadelain et al. | |
| 2009/0124566 | A1 | 5/2009 | Chi et al. | |
| 2009/0156534 | A1 | 6/2009 | Lisowski et al. | |
| 2009/0274671 | A1 | 11/2009 | Sadelain et al. | |
| 2012/0009161 | A1 | 1/2012 | Leboulch et al. | |
| 2012/0039932 | A1 | 2/2012 | Allen et al. | |
| 2015/0224209 | A1 | 8/2015 | Kohn et al. | |
| 2017/0157270 | A1 | 6/2017 | Kohn et al. | |
| 2017/0173185 | A1 | 6/2017 | Sadelain et al. | |
| 2018/0008725 | A1 | 1/2018 | Rivella et al. | |
| 2018/0051059 | A1 | 2/2018 | Blobel et al. | |
| 2018/0363004 | A1 | 12/2018 | Heffner et al. | |
| 2021/0222200 | A1 * | 7/2021 | Rivella | C12N 15/86 |
| 2022/0389448 | A1 * | 12/2022 | Rivella | C07K 14/47 |

FOREIGN PATENT DOCUMENTS

| | | | |
|---|---|---|---|
| WO | 2002/010454 | A2 | 2/2002 |
| WO | 2003/002155 | A1 | 1/2003 |
| WO | 2004/083383 | A2 | 9/2004 |
| WO | 2011/011584 | A1 | 1/2011 |
| WO | 2013/184197 | A1 | 12/2013 |

(Continued)

OTHER PUBLICATIONS

Fraser et al. 1993. Each hypersensitive site of the human β-globin locus control region confers a different developmental pattern of expression on the globin genes. Gene Develop. 7:106-113 (Year: 1993).*

(Continued)

*Primary Examiner* — Nancy J Leith
*Assistant Examiner* — Ruth Sophia Arieti
(74) *Attorney, Agent, or Firm* — Robert C. Netter, Jr.; Dann, Dorfman, Herrell & Skillman

(57) ABSTRACT

In one aspect of the instant invention, lentiviral vectors are provided, particularly for treating hemoglobinopathies. Composition comprising the lentiviral vector are also encompassed by the instant invention. In accordance with another aspect of the instant invention, methods of inhibiting, treating, and/or preventing a hemoglobinopathy (e.g., sickle cell disease or thalassemia) in a subject are provided. In a particular embodiment, the method comprises administering a viral vector of the instant invention to a subject in need thereof hemoglobinopathy. In a particular embodiment, the subject has sickle cell anemia.

10 Claims, 62 Drawing Sheets

Figure 1A:
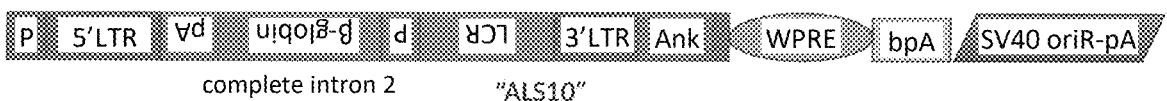

Specification includes a Sequence Listing.

(56) References Cited

FOREIGN PATENT DOCUMENTS

| WO | 2014/043131 A1 | 3/2014 |
| WO | 2014/108812 A2 | 7/2014 |
| WO | 2016/118715 A1 | 7/2016 |
| WO | 2017/079591 A2 | 5/2017 |
| WO | WO-2017003792 A1 * | 7/2017 | ............ A61K 35/28 |
| WO | 2017/191274 A2 | 11/2017 |
| WO | 2020/056400 A1 | 3/2020 |

OTHER PUBLICATIONS

Dutta and Goodsell. 2003. Molecule of the Month: Hemoglobin. PDB-101 May 2003 (Year: 2003).*

Oh et al. 2007. Lentiviral vector design using alternative RNA export elements. Retrovirology 4:38 (Year: 2007).*

Emery. 2011. The Use of Chromatin Insulators to Improve the Expression and Safety of Integrating Gene Transfer Vectors. Hum. Gene Ther. 22:761-774 (Year: 2011).*

U.S. Appl. No. 17/694,841, filed Mar. 2022.*

Kannengiesser, et al., "Missense SLC25A38 variations play an important role in autosomal recessive inherited sideroblastic anemia" Haematoloica (2011) 96(6):808-813.

Guernsey, et al., "Mutations in mitochondrial carrier family gene SLC25A38 cause nonsyndromic autosomal recessive congenital sideroblastic anemia" Nat. Genet. (2009) 41(6): 651-653.

Dufay, J.N., "Defining the role of Hem25 in mitochondrial function: implications for congenital sideroblastic anemia" Master of Science Thesis, Dalhousie University, Hailfax, Nova Scotia (2015) Retrieved from the internet: https://dalspace.library.dal.ca/handle/10222/58896.

Chiabrando, et al., "Heme and erythropoieis: more than a structural role" Haematologica (2014) 99(6):973-83.

Musallam, K.M., et al., "Non-transfusion-dependent thalassemias" Haematologica (2013) 98(6):833-44.

Rivella, S., "The role of ineffective erythropoiesis in non-transfusion-dependent thalassemia" Blood Rev. (2012) 26 Suppl 1:S12-5.

Ginzburg, Y., et al., "β-thalassemia: a model for elucidating the dynamic regulation of ineffective erythropoiesis and iron metabolism" Blood (2011) 118(16):4321-30.

May, C., et al., "Successful treatment of murine beta-thalassemia intermedia by transfer of the human beta-globin gene" Blood (2002) 99(6):1902-8.

May, C., et al., "Therapeutic haemoglobin synthesis in beta-thalassaemic mice expressing lentivirus-encoded human beta-globin" Nature (2000) 406(6791):82-6.

Rivella, S., et al., "A novel murine model of Cooley anemia and its rescue by lentiviral-mediated human beta-globin gene transfer" Blood (2003) 101(8):2932-9.

Breda, L., et al., "Therapeutic hemoglobin levels after gene transfer in β-thalassemia mice and in hematopoietic cells of β-thalassemia and sickle cells disease patients" PLoS One (2012) 7(3):e32345.

Pawliuk, R., et al., "Correction of sickle cell disease in transgenic mouse models by gene therapy" Science (2001) 294(5550):2368-71.

Cavazzana-Calvo, M., et al., "Transfusion independence and HMGA2 activation after gene therapy of human β-thalassaemia" Nature (2010) 467(7313):318-22.

Samakoglu, S., et al., "A genetic strategy to treat sickle cell anemia by coregulating globin transgene expression and RNA interference" Nat. Biotechnol. (2006) 24(1):89-94.

Deng, W., et al., "Reactivation of developmentally silenced globin genes by forced chromatin looping" Cell (2014) 158(4):849-860.

Negre, O., et al., "Gene Therapy of the β-Hemoglobinopathies by Lentiviral Transfer of the β(A(T87Q))—Globin Gene" Hum Gene Ther. (2016) 27(2):148-65.

Bokinni, et al., "Producing and evaluating a novel lentiviral vector for beta-thalassaemia gene therapy" BMC Proceedings (2012) 6(Suppl 4):015.

Leboulch, P., et al., "Mutagenesis of retroviral vectors transducing human beta-globin gene and beta-globin locus control region derivatives results in stable transmission of an active transcriptional structure" EMBO J. (1994) 13 (13):3065-76.

Arumugam, P., et al., "Genetic Therapy for Beta-Thalassemia: From the Bench to the Bedside" Hematology Am. Soc. Hematol. Educ. Program (2010) 2010(1):445-450.

Lisowski, et al., "Current status of globin gene therapy for the treatment of beta-thalassaemia" Br. J. Haematol. (2008) 141(3):335-45.

Antoniou, et al., "Efficient 3'-end formation of human beta-globin mRNA in vivo requires sequences within the last intron but occurs independently of the splicing reaction" Nucleic Acids Res. (1998) 26(3):721-9.

El-Rashidi, et al., "The role of soluble transferrin receptor in iron overload in children with chronic hemolytic anemia" Menoufia Medical Journal (2013) 26:132-137.

Li, et al., "Transferrin therapy ameliorates disease in beta-thalassemic mice" Nat Med. (2010) 16(2):177-82.

Huebers, et al., "The physiology of transferrin and transferrin receptors" Physiol. Rev. (1987) 67(2):520-82.

Abelson, et al. "tRNA Splicing" J. Biol. Chem. (1998) 273(21):12685-12688.

Molecular Biology Web Book, Chapter 5: Posttranscriptional Processes, A4: RNA Splicing, obtained at https://www.web-books.com/MoBio/Free/Ch5A4.htm (2019) pp. 1-5.

Wikipedia, Complementary DNA, obtained at https://en.wikipedia,org/wiki/Complementary_DNA (2019) pp. 1-3.

Drakopoulou, et al., "Towards more successful gene therapy clinical trials for β-thalassemia" Curr Mol Med. (2013) 13(8):1314-30.

Guda, et al., "miRNA-embedded shRNAs for Lineage-specific BCL11A Knockdown and Hemoglobin F Induction" Molecular Therapy (2015) 23(9):1465-1474.

Fellmann, et al., "An Optimized microRNA Backbone for Effective Single-Copy RNAi" Cell Reports (2013) 6:1704-1713.

Zaiss, et al., "RNA 3' readthrough of oncoretrovirus and lentivirus: implications for vector safety and efficacy" J Virol. (2002) 76(14):7209-19.

Puthenveetil, et al., "Successful correction of the human beta-thalassemia major phenotype using a lentiviral vector" Blood (2004) 104(12):3445-53.

Wilber, et al., "Therapeutic levels of fetal hemoglobin in erythroid progeny of β-thalassemic CD34+ cells after entiviral vector-mediated gene transfer" Blood (2011) 117(10):2817-26.

Miccio, et al., "The GATA1-HS2 enhancer allows persistent and position-independent expression of a β-globin transgene" PLoS One (2011) 6(12):e27955.

Lourenco, et al., "Screening Vectors for the Treatment of ß-Globinopathies: a Quest for More Efficient Therapies" American Society of Gene & Cell Therapy, Chicago (2018) available at https://plan.core-apps.com/asgct2018/abstract/a87546bc-e7ce-4fb8-9998-d59aa67babb5.

Ikawa, et al., "High Levels of Transduction in CD34 Positive Cells and Toxicology Studies Using New Lentiviral Vectors for the Cure of Hemoglobinopathies" Molecular Therapy (2019) 27(4S1):285.

Lourenco, et al., "HbA and HbF Simultaneous Induction by Double-Pronged Lentiviral Vector ATM1.1 Outperforms Beta-Globin-Based Gene Addition and miRNA-Based Gamma-Globin Reactivation in SCD-Derived Erythroblasts" Molecular Therapy (2019) 27(4S1):279.

Lisowski, et al., "Locus control region elements HS1 and HS4 enhance the therapeutic efficacy of globin gene transfer in beta-thalassemic mice" Blood (2007) 110:4175-4178.

Rai, et al., "Gene therapy for hemoglobin disorders—a mini-review" J. Rare Dis. Res. Treat. (2016) 1(2): 25-31.

Dong, et al., "Gene therapy for hemoglobinopathies: progress and challenges" Transl. Res. (2013) 161(4):293-306.

Han, et al., "Fetal gene therapy of α-thalassemia in a mouse model" Proc. Natl. Acad. Sci. (2007) 104(21):9007-11.

Mauro, et al., "A critical analysis of codon optimization in human therapeutics" Trends Mol. Med. (2014) 20(11):604-613.

* cited by examiner complete intron 2        "ALS10"

VCN=1.37 ± 0.2

VCN=1.29 ± 0.07          VCN=1.7

```
ctgtcagaccaagtttactcatatatactttagattgatttaaaacttca
+-+-+-+-+-+-+-+-+-+-+-+-+-+-+-+-+-+-+-+-+-+-+-+-+-+    50
                    pBSSK+ plasmid
```

```
tttttaatttaaaaggatctaggtgaagatccttttttgataatctcatga
+-+-+-+-+-+-+-+-+-+-+-+-+-+-+-+-+-+-+-+-+-+-+-+-+-+    100
                    pBSSK+ plasmid
```

```
ccaaaatcccttaacgtgagttttcgttccactgagcgtcagaccccgta
+-+-+-+-+-+-+-+-+-+-+-+-+-+-+-+-+-+-+-+-+-+-+-+-+-+    150
                    pBSSK+ plasmid
```

```
gaaaagatcaaaggatcttcttgagatcctttttttctgcgcgtaatctg
+-+-+-+-+-+-+-+-+-+-+-+-+-+-+-+-+-+-+-+-+-+-+-+-+-+    200
                    pBSSK+ plasmid
```

```
ctgcttgcaaacaaaaaaaccaccgctaccagcggtggtttgtttgccgg
+-+-+-+-+-+-+-+-+-+-+-+-+-+-+-+-+-+-+-+-+-+-+-+-+-+    250
                    pBSSK+ plasmid
```

```
atcaagagctaccaactcttttttccgaaggtaactggcttcagcagagcg
+-+-+-+-+-+-+-+-+-+-+-+-+-+-+-+-+-+-+-+-+-+-+-+-+-+    300
                    pBSSK+ plasmid
```

```
cagataccaaatactgtccttctagtgtagccgtagttaggccaccactt
+-+-+-+-+-+-+-+-+-+-+-+-+-+-+-+-+-+-+-+-+-+-+-+-+-+    350
                    pBSSK+ plasmid
```

```
caagaactctgtagcaccgcctacatacctcgctctgctaatcctgttac
+-+-+-+-+-+-+-+-+-+-+-+-+-+-+-+-+-+-+-+-+-+-+-+-+-+    400
                    pBSSK+ plasmid
```

```
cagtggctgctgccagtggcgataagtcgtgtcttaccgggttggactca
+-+-+-+-+-+-+-+-+-+-+-+-+-+-+-+-+-+-+-+-+-+-+-+-+-+    450
                    pBSSK+ plasmid
```

FIG. 4B

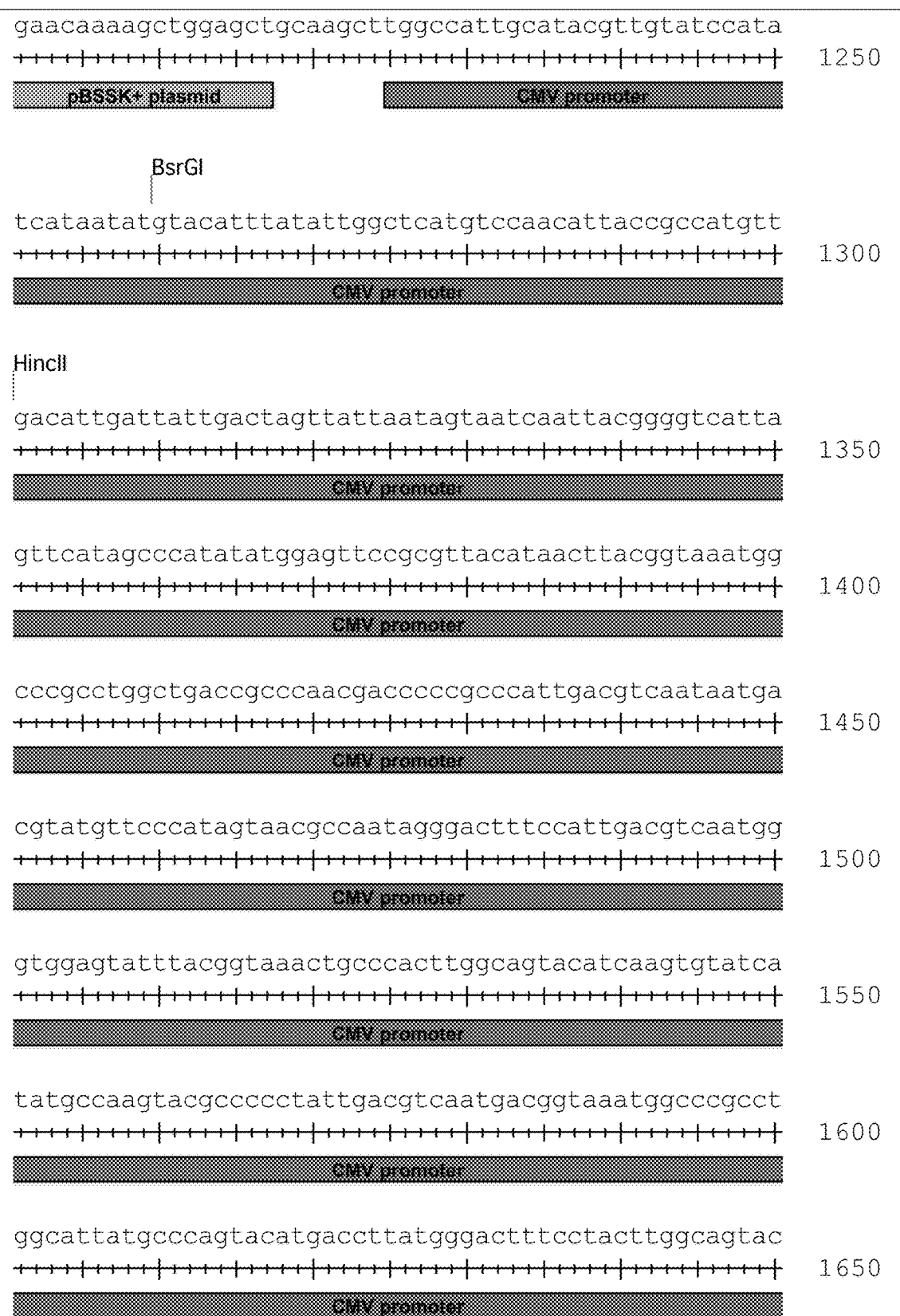

```
gaacaaaagctggagctgcaagcttggccattgcatacgttgtatccata
+-+-+-+-+-+-+-+-+-+-+-+-+-+-+-+-+-+-+-+-+-+-+-+-+-+    1250
```
pBSSK+ plasmid                CMV promoter BsrGI
```
tcataatatgtacatttatattggctcatgtccaacattaccgccatgtt
+-+-+-+-+-+-+-+-+-+-+-+-+-+-+-+-+-+-+-+-+-+-+-+-+-+    1300
```
CMV promoter HincII
```
gacattgattattgactagttattaatagtaatcaattacggggtcatta
+-+-+-+-+-+-+-+-+-+-+-+-+-+-+-+-+-+-+-+-+-+-+-+-+-+    1350
```
CMV promoter

```
gttcatagcccatatatggagttccgcgttacataacttacggtaaatgg
+-+-+-+-+-+-+-+-+-+-+-+-+-+-+-+-+-+-+-+-+-+-+-+-+-+    1400
```
CMV promoter

```
cccgcctggctgaccgcccaacgacccccgcccattgacgtcaataatga
+-+-+-+-+-+-+-+-+-+-+-+-+-+-+-+-+-+-+-+-+-+-+-+-+-+    1450
```
CMV promoter

```
cgtatgttcccatagtaacgccaatagggactttccattgacgtcaatgg
+-+-+-+-+-+-+-+-+-+-+-+-+-+-+-+-+-+-+-+-+-+-+-+-+-+    1500
```
CMV promoter

```
gtggagtatttacggtaaactgcccacttggcagtacatcaagtgtatca
+-+-+-+-+-+-+-+-+-+-+-+-+-+-+-+-+-+-+-+-+-+-+-+-+-+    1550
```
CMV promoter

```
tatgccaagtacgccccctattgacgtcaatgacggtaaatggcccgcct
+-+-+-+-+-+-+-+-+-+-+-+-+-+-+-+-+-+-+-+-+-+-+-+-+-+    1600
```
CMV promoter

```
ggcattatgcccagtacatgaccttatgggactttcctacttggcagtac
+-+-+-+-+-+-+-+-+-+-+-+-+-+-+-+-+-+-+-+-+-+-+-+-+-+    1650
```
CMV promoter

FIG. 4B (Cont'd)

agaattacaaaaacaaattacaaaaattcaaaattttatCGATAAGCTTG
├─┼─┼─┼─┼─┼─┼─┼─┼─┼─┼─┼─┼─┼─┼─┼─┼─┼─┼─┼─┼─┼─┼─┤   3600

—————————————— HIV —————————————● cPPT or FLAP

GGAGTTCCGCGTGTTGGGGGTGGACCATCCTCTAGGTATTGAATAAGAAA
├─┼─┼─┼─┼─┼─┼─┼─┼─┼─┼─┼─┼─┼─┼─┼─┼─┼─┼─┼─┼─┼─┼─┤   3650

AATGAAGTTAAGGTGGTTGATGGTAACACTATGCTAATAACTGCAGAGCC
├─┼─┼─┼─┼─┼─┼─┼─┼─┼─┼─┼─┼─┼─┼─┼─┼─┼─┼─┼─┼─┼─┼─┤   3700

AGAAGCACCATAAGGGACATGATAAGGGAGCCAGCAGACCTCTGATCTCT
├─┼─┼─┼─┼─┼─┼─┼─┼─┼─┼─┼─┼─┼─┼─┼─┼─┼─┼─┼─┼─┼─┼─┤   3750

TCCTGAATGCTAATCTTAAACATCCTGAGGAAGAATGGGACTTCCATTTG
├─┼─┼─┼─┼─┼─┼─┼─┼─┼─┼─┼─┼─┼─┼─┼─┼─┼─┼─┼─┼─┼─┼─┤   3800

EcoNI
┊

GGGTGGGCCTATGATAGGGTAATAAGACAGTAGTGAATATCAAGCTACAA
├─┼─┼─┼─┼─┼─┼─┼─┼─┼─┼─┼─┼─┼─┼─┼─┼─┼─┼─┼─┼─┼─┼─┤   3850

AAAGCCCCCTTTCAAATTCTTCTCAGTCCTAACTTTTCATACTAAGCCCA
├─┼─┼─┼─┼─┼─┼─┼─┼─┼─┼─┼─┼─┼─┼─┼─┼─┼─┼─┼─┼─┼─┼─┤   3900

PfoI
┊

GTCCTTCCAAAGCAGACTGTGAAAGAGTGATAGTTCCGGGAGACTAGCAC
├─┼─┼─┼─┼─┼─┼─┼─┼─┼─┼─┼─┼─┼─┼─┼─┼─┼─┼─┼─┼─┼─┼─┤   3950

TGCAGATTCCGGGTCACTGTGAGTGGGGGAGGCAGGGAAGAAGGGCTCAC
├─┼─┼─┼─┼─┼─┼─┼─┼─┼─┼─┼─┼─┼─┼─┼─┼─┼─┼─┼─┼─┼─┼─┤   4000

AGGACAGTCAAACCATGCCCCCTGTTTTTCCTTCTTCAAGTAGACCTCTA
├─┼─┼─┼─┼─┼─┼─┼─┼─┼─┼─┼─┼─┼─┼─┼─┼─┼─┼─┼─┼─┼─┼─┤   4050

TAAGACAACAGAGACAACTAAGGCTGAGTGGCCAGGCGAGGAGAAACCAT
├─┼─┼─┼─┼─┼─┼─┼─┼─┼─┼─┼─┼─┼─┼─┼─┼─┼─┼─┼─┼─┼─┼─┤   4100

CTCGCCGTAAAACATGGAAGGAACACTTCAGGGGAAAGGTGGTATCTCTA
├─┼─┼─┼─┼─┼─┼─┼─┼─┼─┼─┼─┼─┼─┼─┼─┼─┼─┼─┼─┼─┼─┼─┤   4150

FIG. 4B (Cont'd)

AGCAAGAGAACTGAGTGGAGTCAAGGCTGAGAGATGCAGGATAAGCAAAT

+++++++++++++++++++++++++++++++++++++++++++++++++  4200

GGGTAGTGAAAAGACATTCATGAGGACAGCTAAAACAATAAGTAATGTAA

+++++++++++++++++++++++++++++++++++++++++++++++++  4250

AATACAGCATAGCAAAACTTTAACCTCCAAATCAAGCCTCTACTTGAATC

+++++++++++++++++++++++++++++++++++++++++++++++++  4300

CTTTTCTGAGGGATGAATAAGGCATAGGCATCAGGGGCTGTTGCCAATGT

+++++++++++++++++++++++++++++++++++++++++++++++++  4350

GCATTAGCTGTTTGCAGCCTCACCTTCTTTCATGGAGTTTAAGATATAGT

+++++++++++++++++++++++++++++++++++++++++++++++++  4400

GTATTTTCCCAAGGTTTGAACTAGCTCTTCATTTCTTTATGTTTTAAATG

+++++++++++++++++++++++++++++++++++++++++++++++++  4450

Swal

CACTGACCTCCCACATTCCCTTTTTAGTAAAATATTCAGAAATAATTTAA

+++++++++++++++++++++++++++++++++++++++++++++++++  4500

ATACATCATTGCAATGAAAATAAATGTTTTTTATTAGGCAGAATCCAGAT

+++++++++++++++++++++++++++++++++++++++++++++++++  4550 beta-globin 3' UTR polyA

GCTCAAGGCCCTTCATAATATCCCCCAGTTTAGTAGTTGGACTTAGGGAA

+++++++++++++++++++++++++++++++++++++++++++++++++  4600 beta-globin 3' UTR

CAAAGGAACCTTTAATAGAAATTGGACAGCAAGAAAGCGAGCTTAGTGAT

+++++++++++++++++++++++++++++++++++++++++++++++++  4650 beta-globin 3' UTR    exon 3

ACTTGTGGGCCAGGGCATTAGCCACACCAGCCACCACTTTCTGATAGGCA

+++++++++++++++++++++++++++++++++++++++++++++++++  4700 exon 3

FIG. 4B (Cont'd)

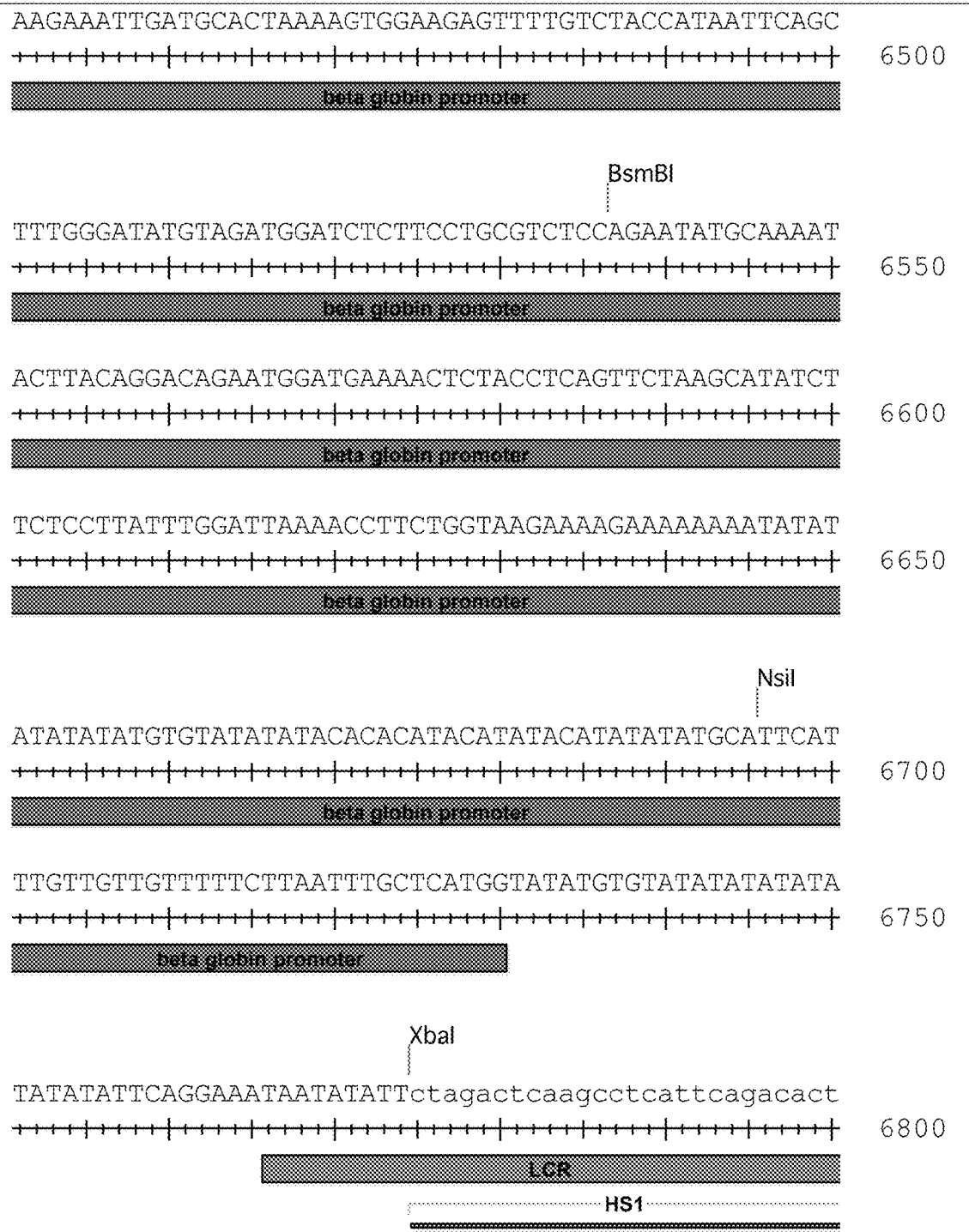

AAGAAATTGATGCACTAAAAGTGGAAGAGTTTTGTCTACCATAATTCAGC
6500
beta globin promoter

BsmBI
TTTGGGATATGTAGATGGATCTCTTCCTGCGTCTCCAGAATATGCAAAAT
6550
beta globin promoter ACTTACAGGACAGAATGGATGAAAACTCTACCTCAGTTCTAAGCATATCT
6600
beta globin promoter TCTCCTTATTTGGATTAAAACCTTCTGGTAAGAAAGAAAAAAATATAT
6650
beta globin promoter NsiI
ATATATATGTGTATATATACACACATACATATACATATATATGCATTCAT
6700
beta globin promoter TTGTTGTTGTTTTTCTTAATTTGCTCATGGTATATGTGTATATATATATA
6750
beta globin promoter XbaI
TATATATTCAGGAAATAATATATTctagactcaagcctcattcagacact
6800
LCR
HS1

FIG. 4B (Cont'd)

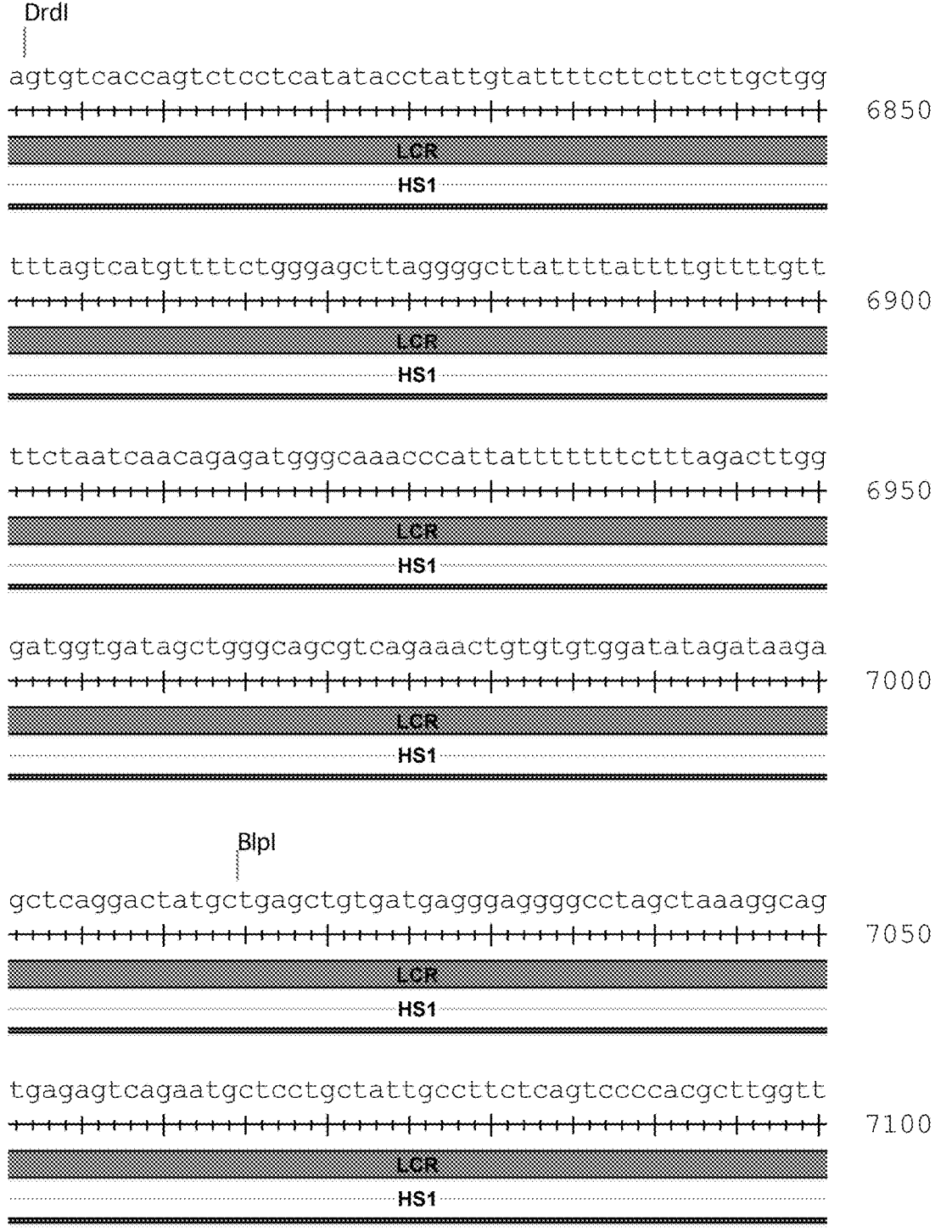

CTTTGCTTCATTGCCCCATCCATCTGATCCTCCTCATCAGTGCAGCACAG
+++++|+++++|+++++|+++++|+++++|+++++|+++++|+++++|+++++|+++++|    9000

LCR

HS3

PspOMI
Apal

GGCCCATGAGCAGTAGCTGCAGAGTCTCACATAGGTCTGGCACTGCCTCT
+++++|+++++|+++++|+++++|+++++|+++++|+++++|+++++|+++++|+++++|    9050

LCR

HS3

PciI
AflIII

GACATGTCCGACCTTAGGCAAATGCTTGACTCTTCTGAGCTCAGTCTTGT
+++++|+++++|+++++|+++++|+++++|+++++|+++++|+++++|+++++|+++++|    9100

LCR

HS3

TstI'

CATGGCAAAATAAAGATAATAATAGTGTTTTTTTATGGAGTTAGCGTGAG
+++++|+++++|+++++|+++++|+++++|+++++|+++++|+++++|+++++|+++++|    9150

LCR

HS3

TstI

GATGGAAAACAATAGCAAAATTGATTAGACTATAAAAGGTCTCAACAAAT
+++++|+++++|+++++|+++++|+++++|+++++|+++++|+++++|+++++|+++++|    9200

LCR

HS3

FIG. 4B (Cont'd)

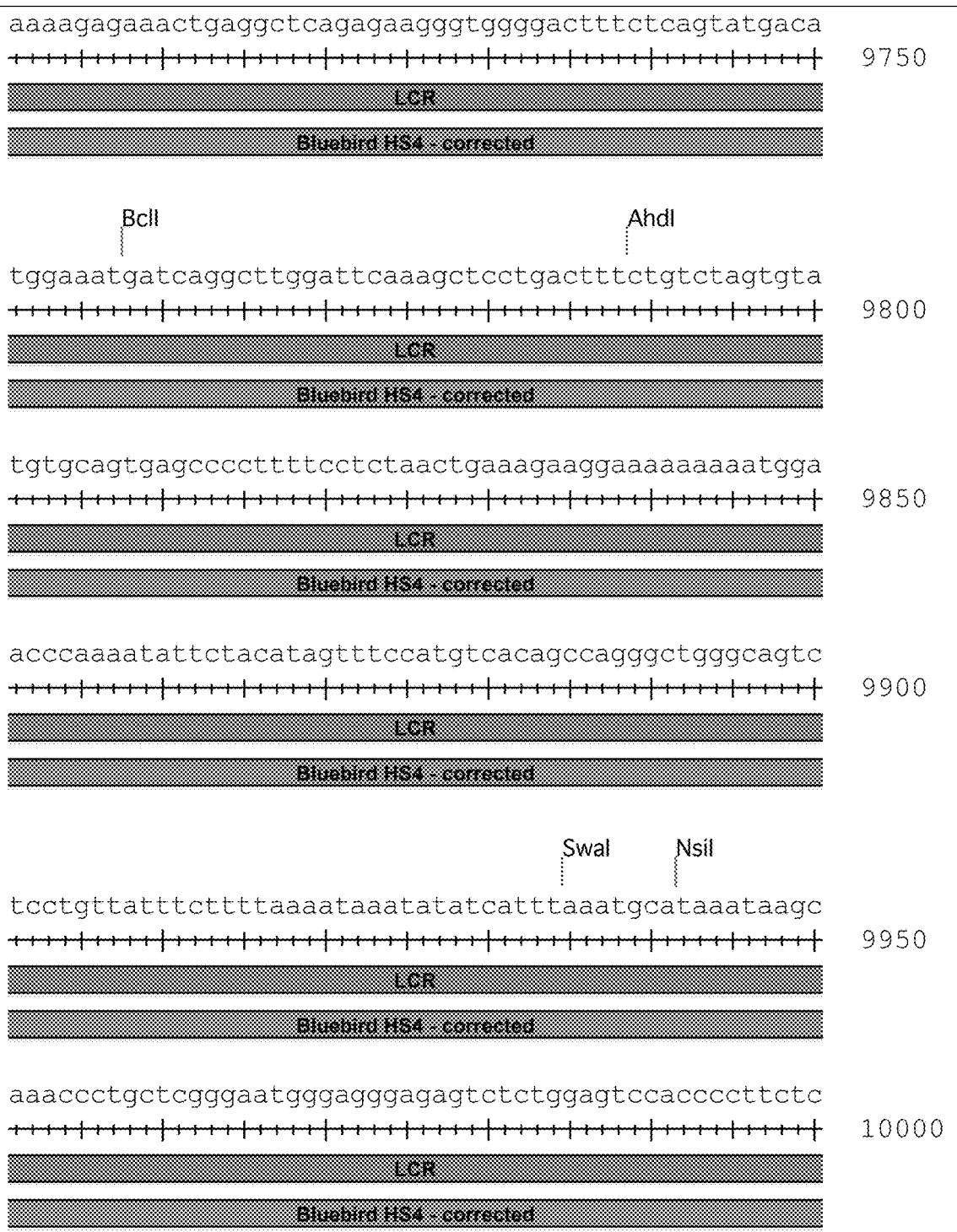

aaaagagaaactgaggctcagagaagggtggggactttctcagtatgaca
9750
LCR
Bluebird HS4 - corrected BclI                                        AhdI
tggaaatgatcaggcttggattcaaagctcctgactttctgtctagtgta
9800
LCR
Bluebird HS4 - corrected tgtgcagtgagccccttttcctctaactgaaagaaggaaaaaaaaatgga
9850
LCR
Bluebird HS4 - corrected acccaaaatattctacatagtttccatgtcacagccagggctgggcagtc
9900
LCR
Bluebird HS4 - corrected Swal          Nsil
tcctgttatttcttttaaaataaatatatcatttaaatgcataaataagc
9950
LCR
Bluebird HS4 - corrected aaaccctgctcgggaatgggagggagagtctctggagtccacccctttctc
10000
LCR
Bluebird HS4 - corrected

FIG. 4B (Cont'd)

acctctggattacaaaatttgtgaaagattgactggtattcttaactatg

11250

WPRE ttgctccttttacgctatgtggatacgctgctttaatgcctttgtatcat

11300

WPRE gctattgcttcccgtatggctttcattttctcctccttgtataaatcctg

11350

WPRE gttgctgtctctttatgaggagttgtggcccgttgtcaggcaacgtggcg

11400

WPRE tggtgtgcactgtgtttgctgacgcaaccccactggttggggcattgcc

11450

WPRE

Pfol accacctgtcagctcctttccgggactttcgctttccccctccctattgc

11500

WPRE cacggcggaactcatcgccgcctgccttgcccgctgctggacaggggctc

11550

WPRE ggctgttgggcactgacaattccgtggtgttgtcggggaagctgacgtcc

11600

WPRE tttccatggctgctcgcctgtgttgccacctggattctgcgcgggacgtc

11650

WPRE

FIG. 4B (Cont'd)

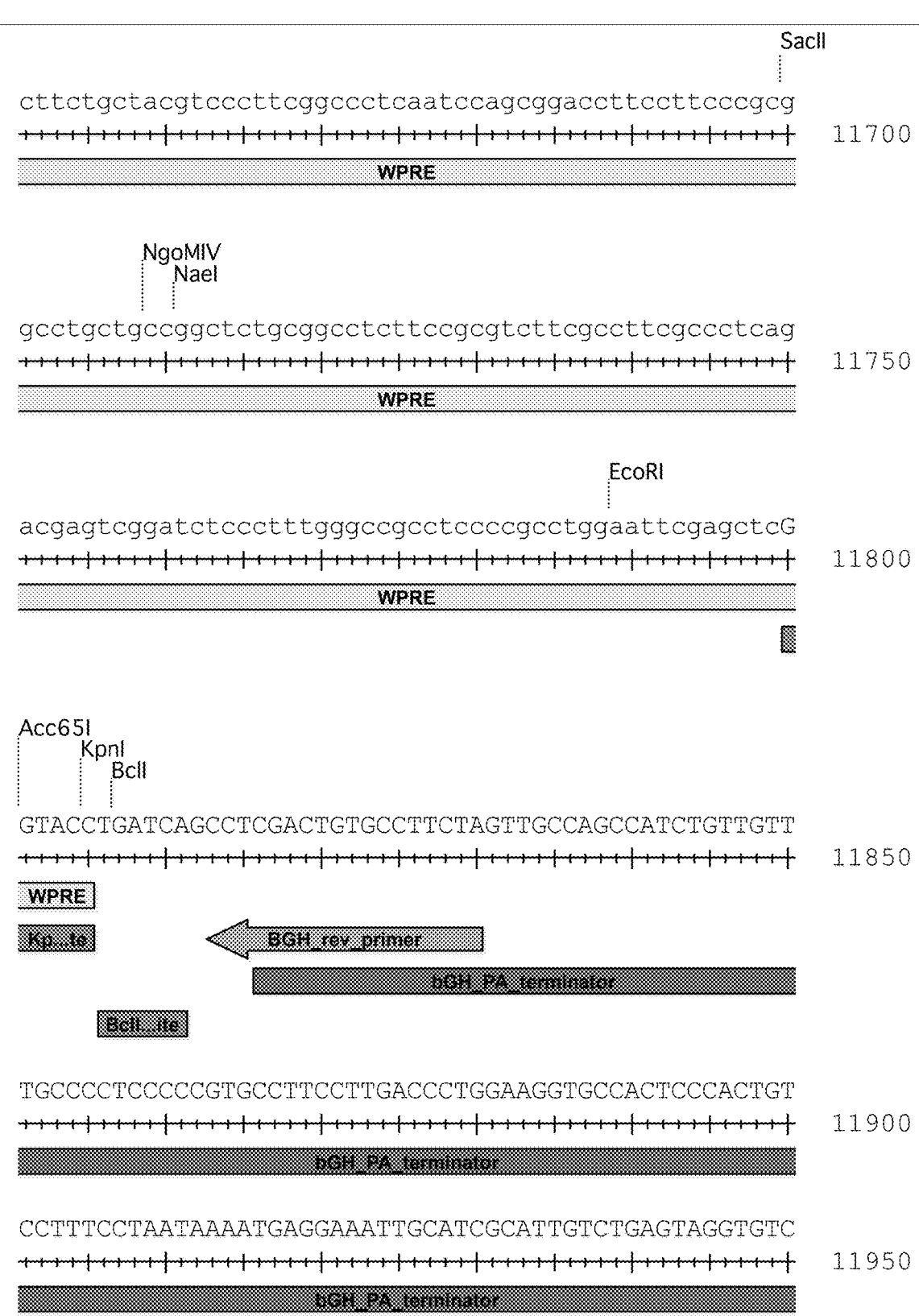

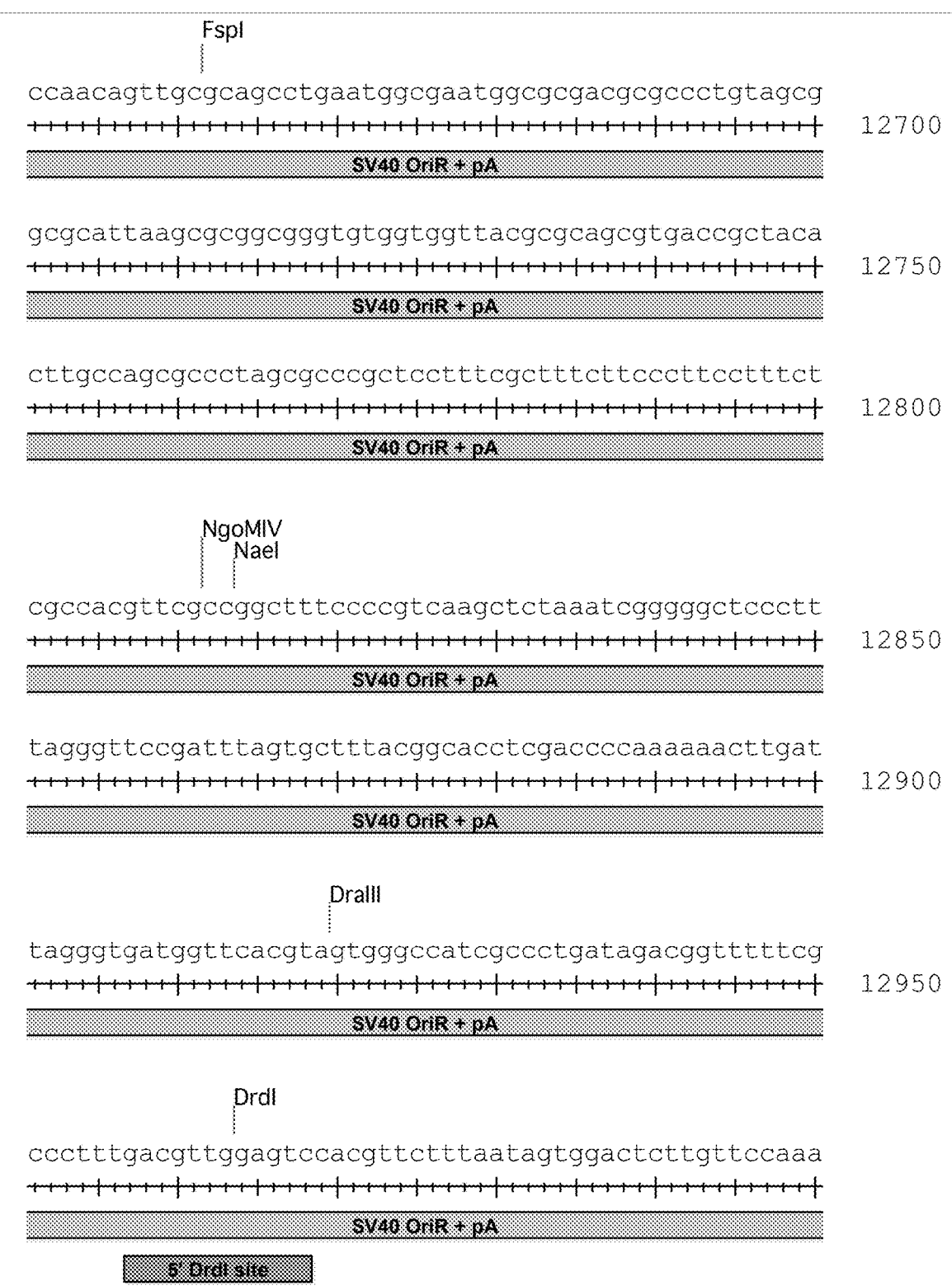

FspI ccaacagttgcgcagcctgaatggcgaatggcgcgacgcgccctgtagcg
                                                    12700
SV40 OriR + pA gcgcattaagcgcggcgggtgtggtggttacgcgcagcgtgaccgctaca
                                                    12750
SV40 OriR + pA cttgccagcgccctagcgcccgctcctttcgctttcttcccttcctttct
                                                    12800
SV40 OriR + pA NgoMIV
  NaeI cgccacgttcgccggctttccccgtcaagctctaaatcggggggctccctt
                                                    12850
SV40 OriR + pA tagggttccgatttagtgctttacggcacctcgaccccaaaaaacttgat
                                                    12900
SV40 OriR + pA DraIII tagggtgatggttcacgtagtgggccatcgccctgatagacggtttttcg
                                                    12950
SV40 OriR + pA DrdI ccctttgacgttggagtccacgttctttaatagtggactcttgttccaaa SV40 OriR + pA 5' DrdI site

FIG. 4B (Cont'd)

VCN 0.73 ± 0.18        VCN 0.68 ± 0.12

Dose/Response in Hudep #13
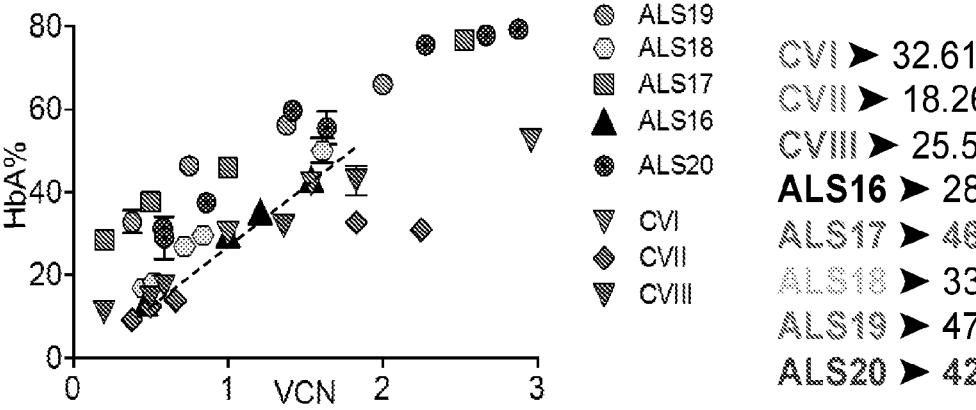
Legend:
- ◎ ALS19
- ◎ ALS18
- ▨ ALS17
- ▲ ALS16
- ● ALS20
- ▽ CVI
- ◆ CVII
- ▽ CVIII
CVI ➤ 32.61 HbA
CVII ➤ 18.26 HbA
CVIII ➤ 25.52 HbA
ALS16 ➤ 28.90 HbA
ALS17 ➤ 46.05 HbA
ALS18 ➤ 33.27 HbA
ALS19 ➤ 47.88 HbA
ALS20 ➤ 42.34 HbA
FIG. 10A
Dose/Response in SCD primary cells
(includ Immortalized SCD13) N=4
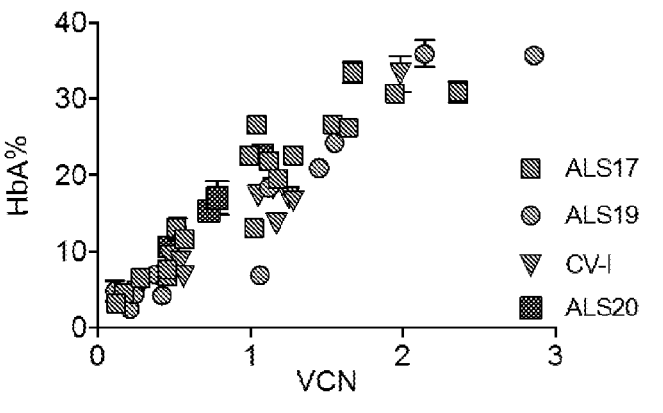
Legend:
- ▨ ALS17
- ◎ ALS19
- ▽ CV-I
- ▨ ALS20
CVI ➤ 15.1 HbA
ALS17 ➤ 17.9 HbA
ALS19 ➤ 15.2 HbA
ALS20 ➤ 21.1 HbA
FIG. 10B
FIG. 10C

Untreated

ATM1.1

VCN 1.9 ± 0.1

COMPOSITIONS AND METHODS FOR HEMOGLOBIN PRODUCTION

This application is a § 371 application of PCT/US2019/029787, filed Apr. 30, 2019, which claims priority under 35 U.S.C. § 119(e) to U.S. Provisional Patent Application No. 62/664,788, filed Apr. 30, 2018. The foregoing applications are incorporated by reference herein.

FIELD OF THE INVENTION

The present invention relates to the field of hematology. More specifically, the invention provides compositions and methods for the production of hemoglobin.

BACKGROUND OF THE INVENTION

Several publications and patent documents are cited throughout the specification in order to describe the state of the art to which this invention pertains. Each of these citations is incorporated herein by reference as though set forth in full.

There are a variety of hemoglobinopathies that affect large portions of the human population. For example, sickle cell anemia, which affects millions throughout the world, is a blood related disorder that affects the structure of the hemoglobin molecules (Steinberg, et al., Disorders of hemoglobin: Genetics, Pathophysiology and Clinical Management, Cambridge University Press, Cambridge, UK, 2001). Additionally, beta-thalassemia is one of the two the most common congenital anemias and is due to partial or complete lack of synthesis of beta-globin chains and hemoglobin due mutations in the beta-globin gene (Musallam, et al. (2013) Haematologica 98:833-844); Rivella, S. (2012) Blood reviews 26 (Suppl 1):S12-15; Ginzburg, et al. (2011) Blood 118:4321-4330). However, hemoglobin levels often decrease over time, splenomegaly appears, and patients suffer from progressive iron overload due to increased gastrointestinal iron absorption. Currently available therapies are limited and have many drawbacks. Thus, there is an ongoing and unmet need for improved compositions and methods for treating hemoglobinopathies.

SUMMARY OF THE INVENTION

In accordance with one aspect of the instant invention, lentiviral vectors are provided, particularly for treating hemoglobinopathies. In a particular embodiment, the lentiviral vector comprises a nucleic acid molecule comprising: i) a 5' long terminal repeat (LTR) and a 3' LTR, wherein one of said LTR is self-inactivating; ii) at least one polyadenylation signal; iii) at least one promoter; iv) a globin gene locus control region (LCR); v) an ankyrin insulator element (Ank); vi) a Woodchuck Post-Regulatory Element (WPRE), particularly wherein the WPRE is 3' of the 3'LTR; and vii) a sequence encoding human beta-globin. In a particular embodiment, the lentiviral vector comprises at least one further modification. In certain embodiment, the beta-globin comprises the complete intron 2 sequence. In certain embodiments, the LCR of the lentiviral vector comprises a complete HS4 region. In certain embodiments, the LCR of the lentiviral vector comprises HS1, HS2, HS3, and HS4. In certain embodiments, the 3'LTR lacks exogenous sequences (e.g., is about 411 nucleotides in length). In certain embodiments, the lentiviral vector further comprising a Rev response element (RRE), particularly located between the LCR and the 3'LTR. In certain embodiments, the lentiviral vector comprises a sequence encoding a BCL11A inhibitory nucleic acid molecule, particularly shRNAmiR—optionally flanked by miR-E sequences. In certain embodiments, the lentiviral vector comprises a sequence encoding an alpha-globin inhibitory nucleic acid molecule. In certain embodiments, the lentiviral vector is selected from the group consisting of ALS16, ALS17, ALS18, ALS19, and ALS20 or is a modified version of these vectors as set forth herein. The instant invention also encompasses erythroid progenitor cells or erythroid cells comprising the lentiviral vector. Composition comprising the lentiviral vector are also encompassed by the instant invention.

In accordance with another aspect of the instant invention, methods of inhibiting, treating, and/or preventing a hemoglobinopathy (e.g., sickle cell disease or thalassemia) in a subject are provided. In a particular embodiment, the method comprises administering a viral vector of the instant invention to a subject in need thereof. In a particular embodiment, the method comprises an ex vivo therapy utilizing a viral vector of the instant invention. The viral vector may be in a composition with a pharmaceutically acceptable carrier. In a particular embodiment, the subject has a f-chain hemoglobinopathy. In a particular embodiment, the subject has sickle cell anemia.

BRIEF DESCRIPTIONS OF THE DRAWINGS

Figure 1B:
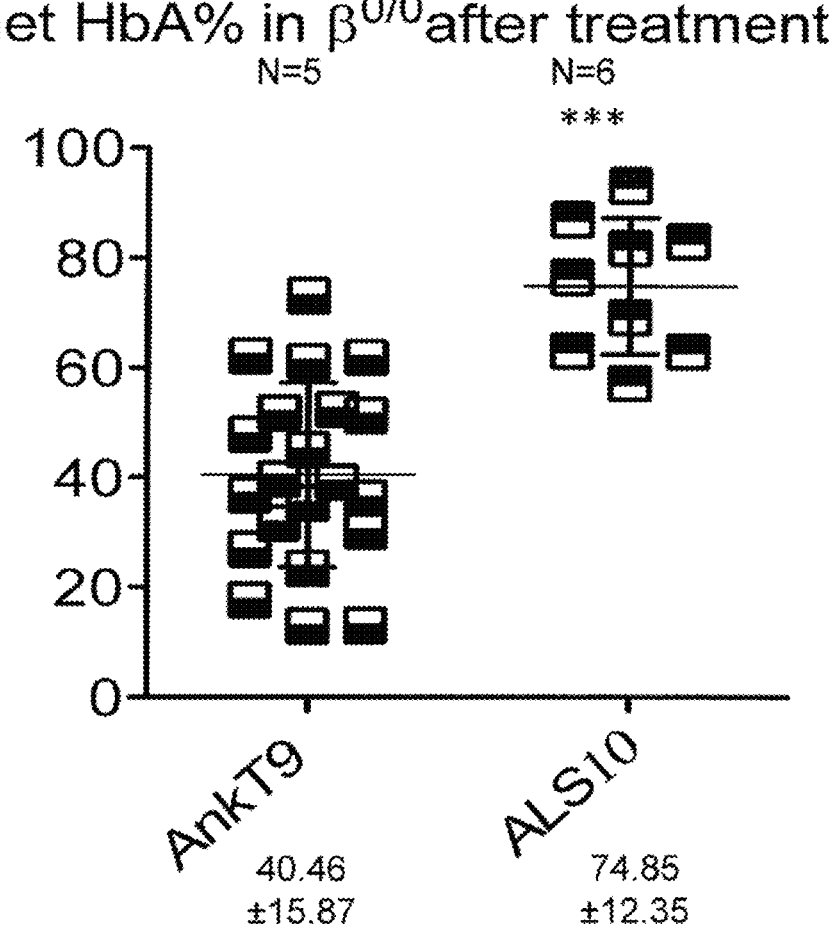

FIG. 1A provides a schematic of a ALS10 vector. FIG. 1B provides a graph of the HbA expression in $\beta^{0/0}$ cells after transduction with AnkT9 or the ALS10 vector.

Figure 2A:
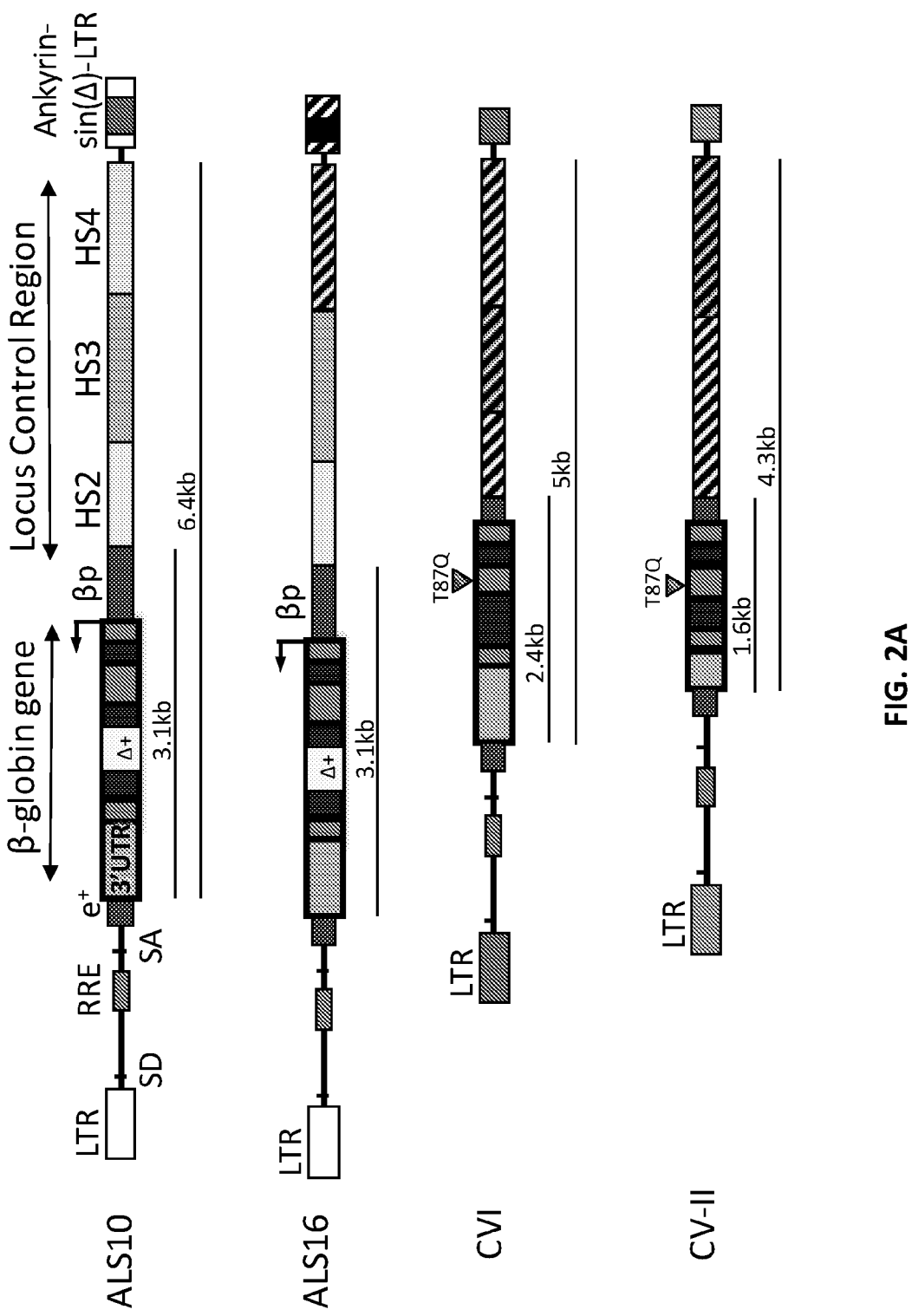
Figure 2B:
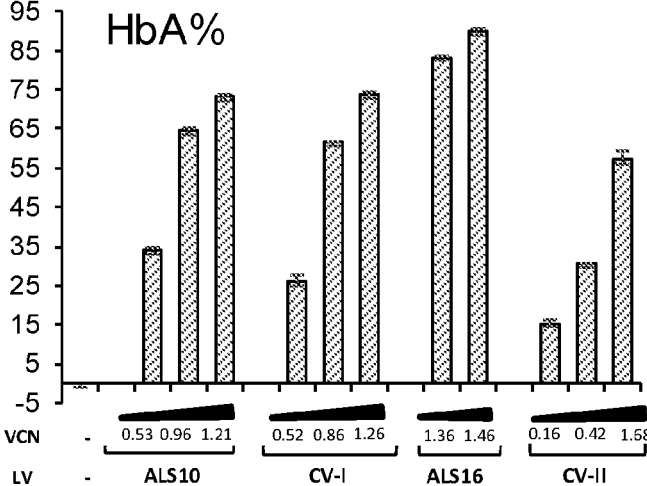
Figure 2B:
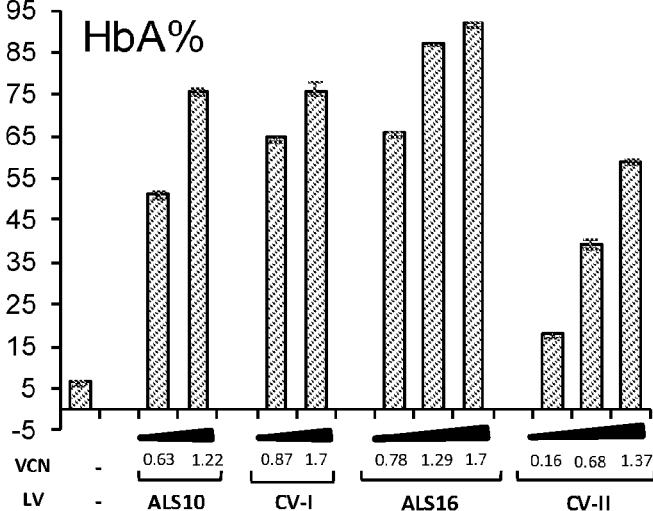
Figure 2C:
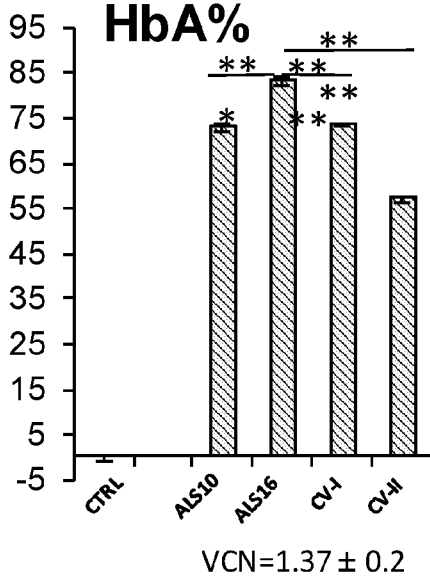
Figure 2C:
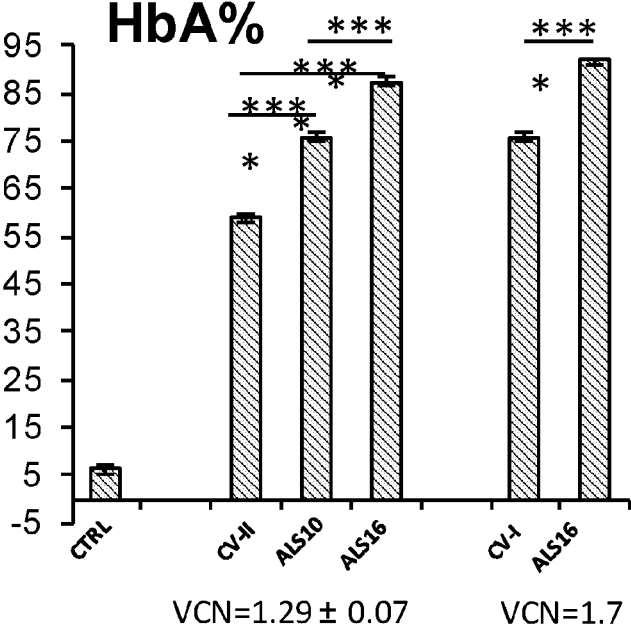

FIG. 2A provides schematic of the ALS10 and ALS16 vectors as well as clinical vector I (CV-I; a vector encoding T87Q beta-globin; LentiGlobin BB305) and CV-II (a vector encoding T87Q beta-globin; Globe vector, TIGET). FIG. 2B provides graphs of the expression of HbA in two different clones of an erythroid progenitor cell line transduced with the indicated viruses at various vector copy numbers (VCN). FIG. 2C provides graphs of the expression of HbA in two different clones of an erythroid progenitor cell line transduced with the indicated viruses with the same vector copy numbers (VCN).

Figure 3A:
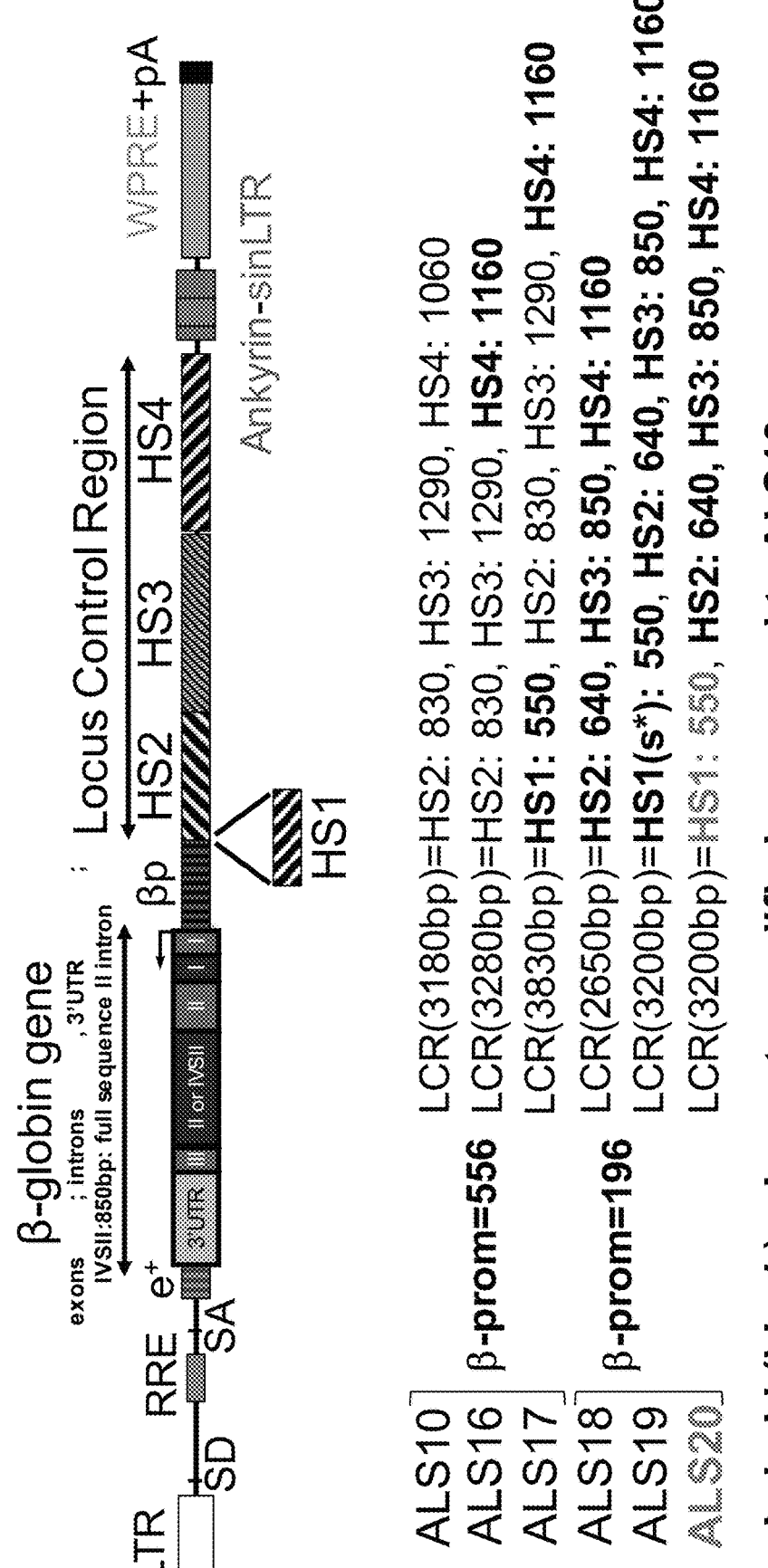
Figure 3B:
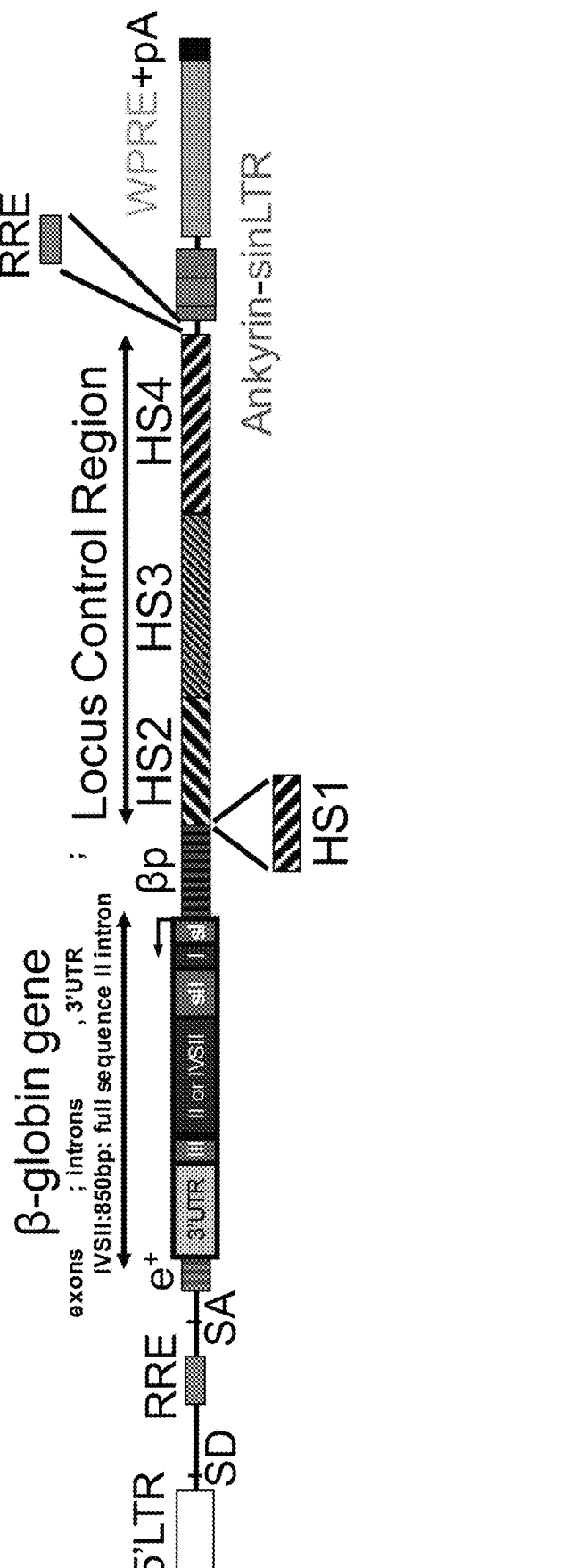

FIG. 3A provides schematics of ALS10, ALS16, ALS17, ALS18, ALS19, and ALS20. FIG. 3B provides a schematic of a further modification wherein the Rev response element (RRE) of HIV is placed between the LCR and the 3'LTR to increase titer.

Figure 4A:
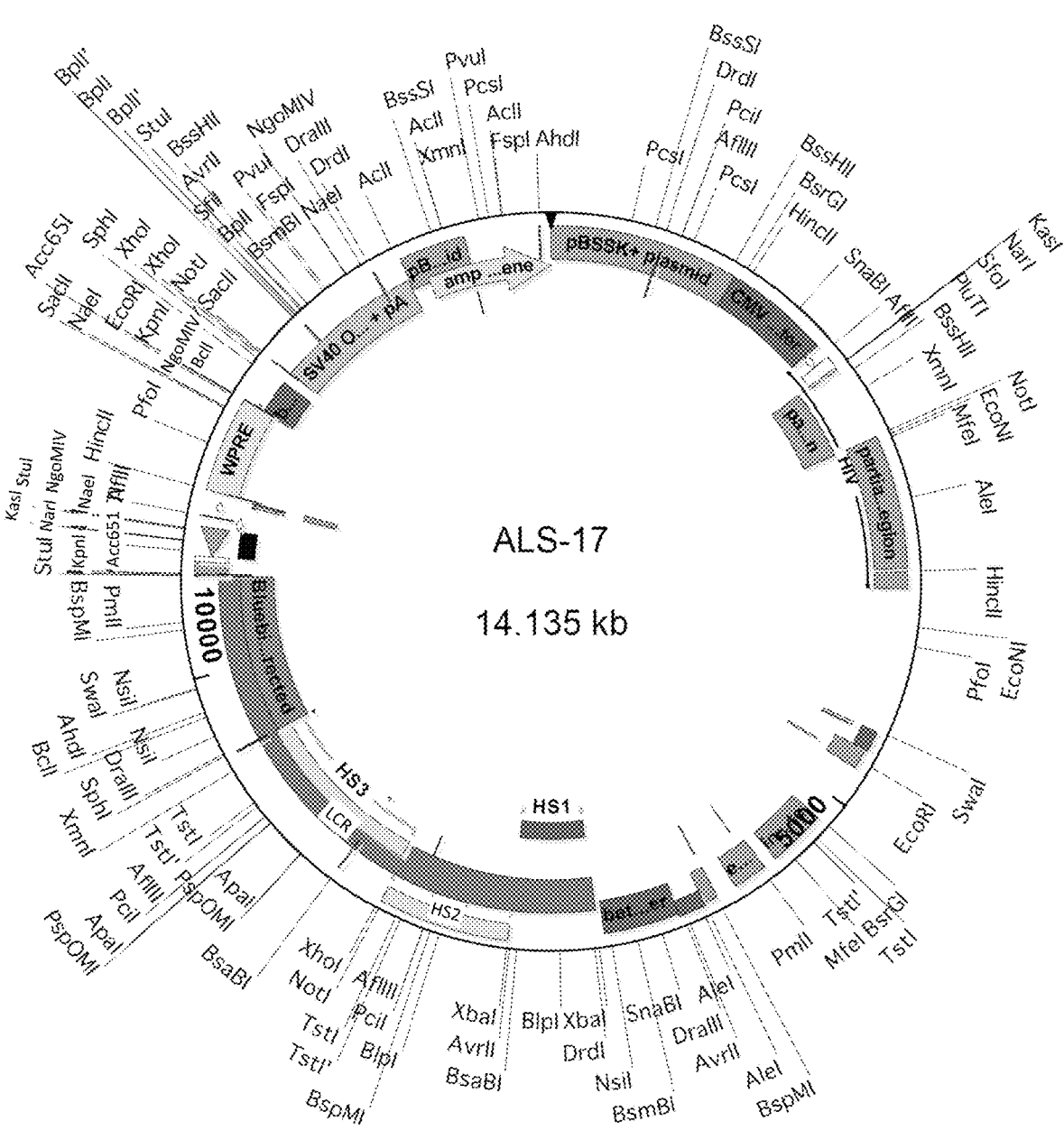
Figure 4B:
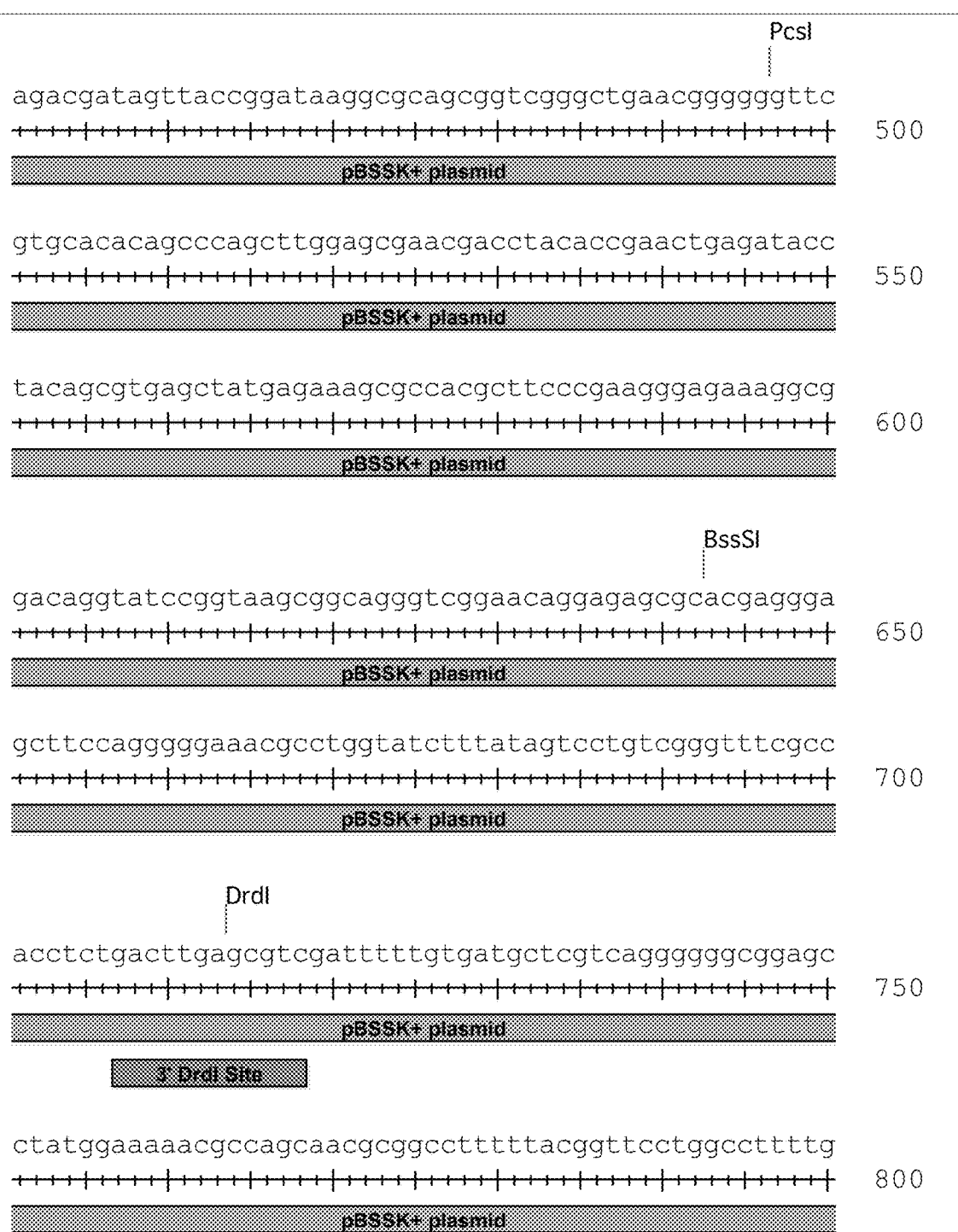
Figure 4B:
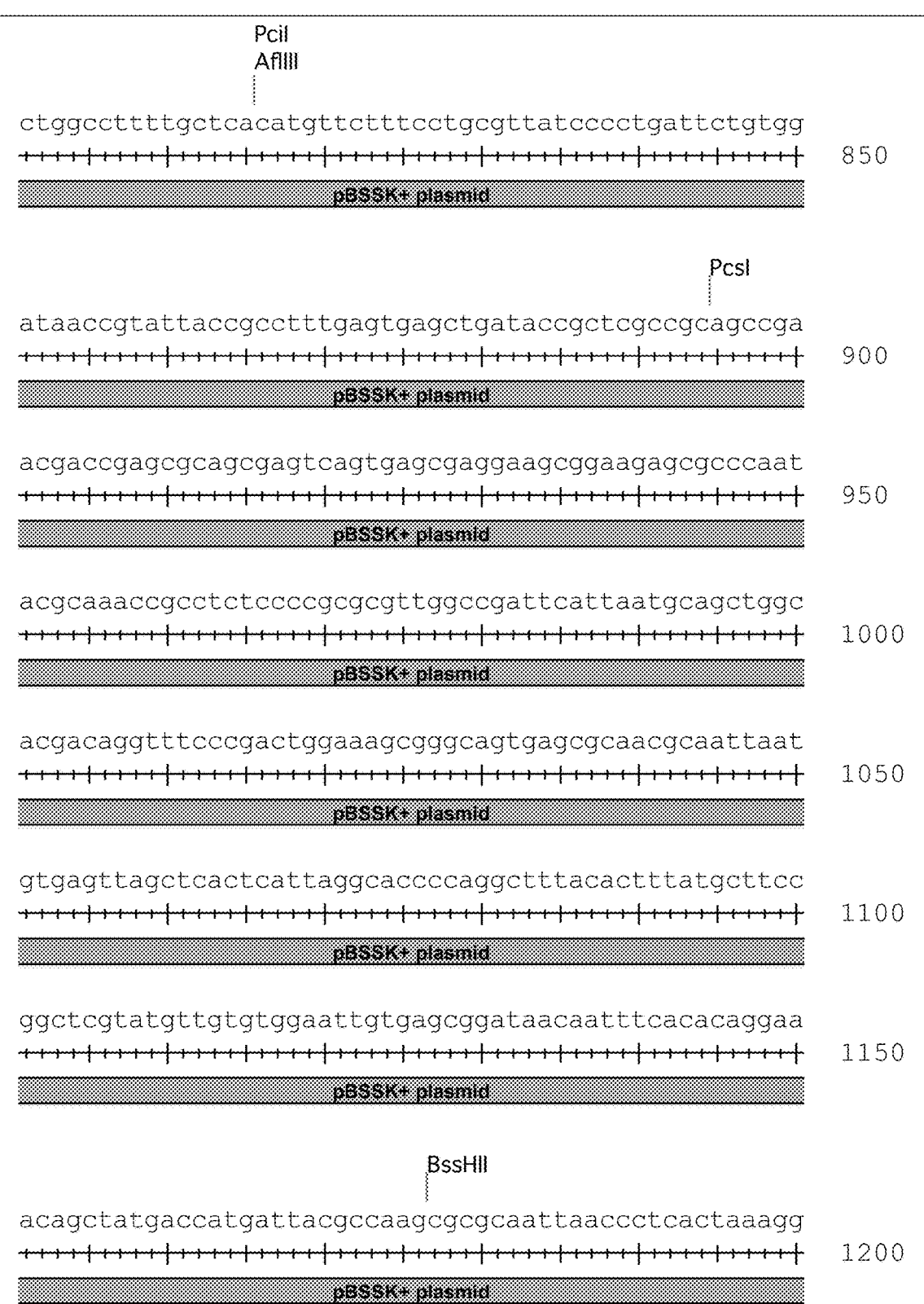
Figure 4B:
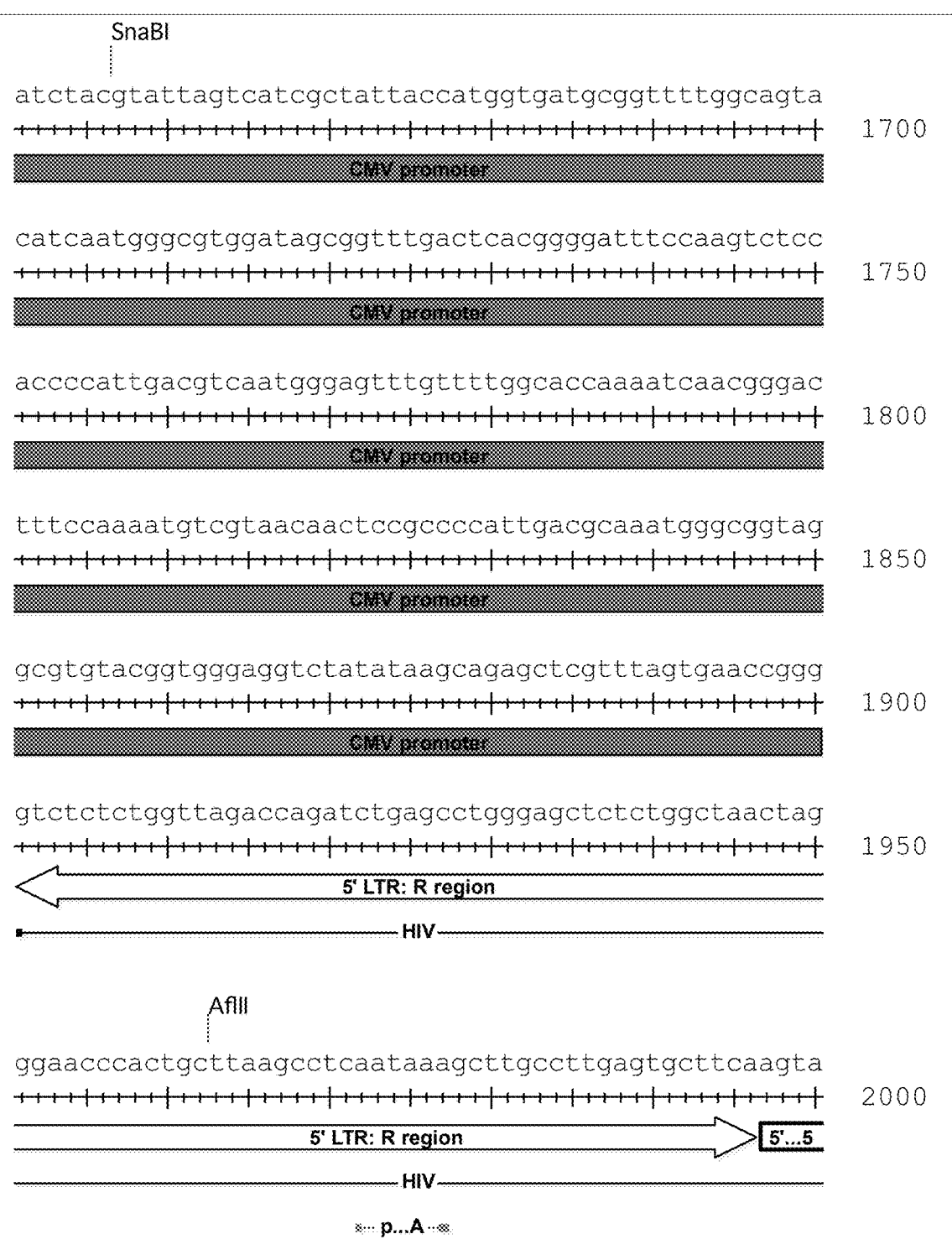
Figure 4B:
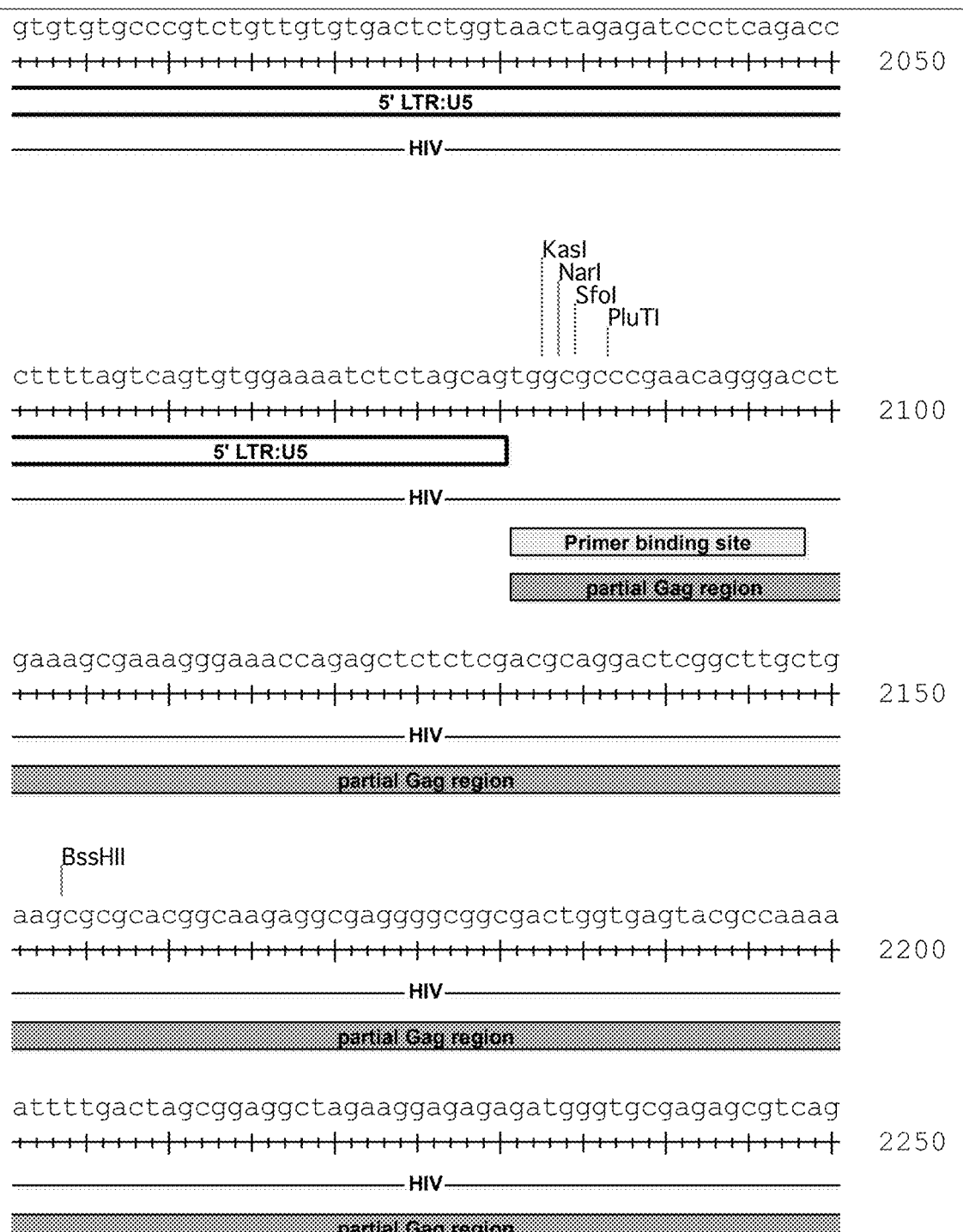
Figure 4B:
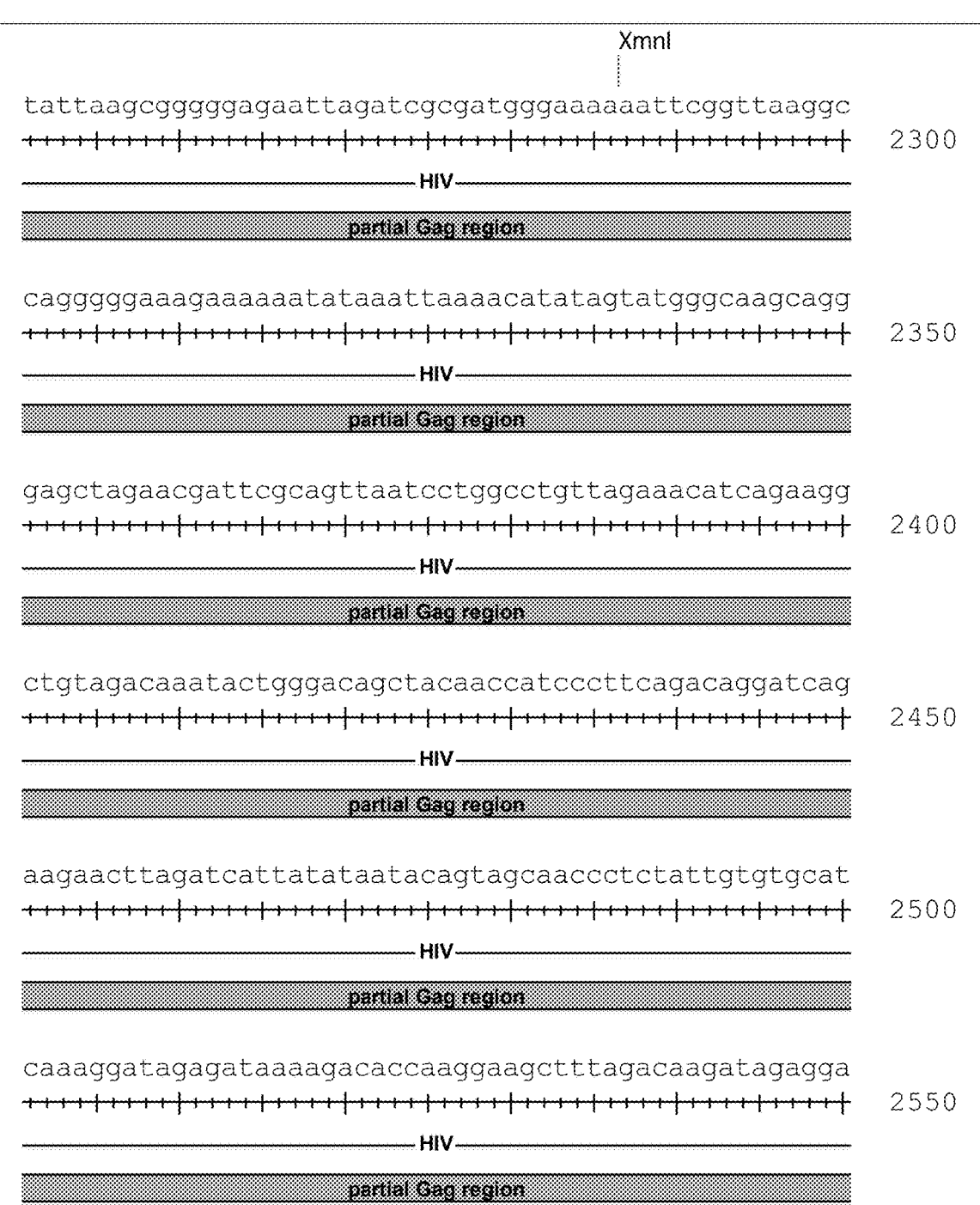
Figure 4B:
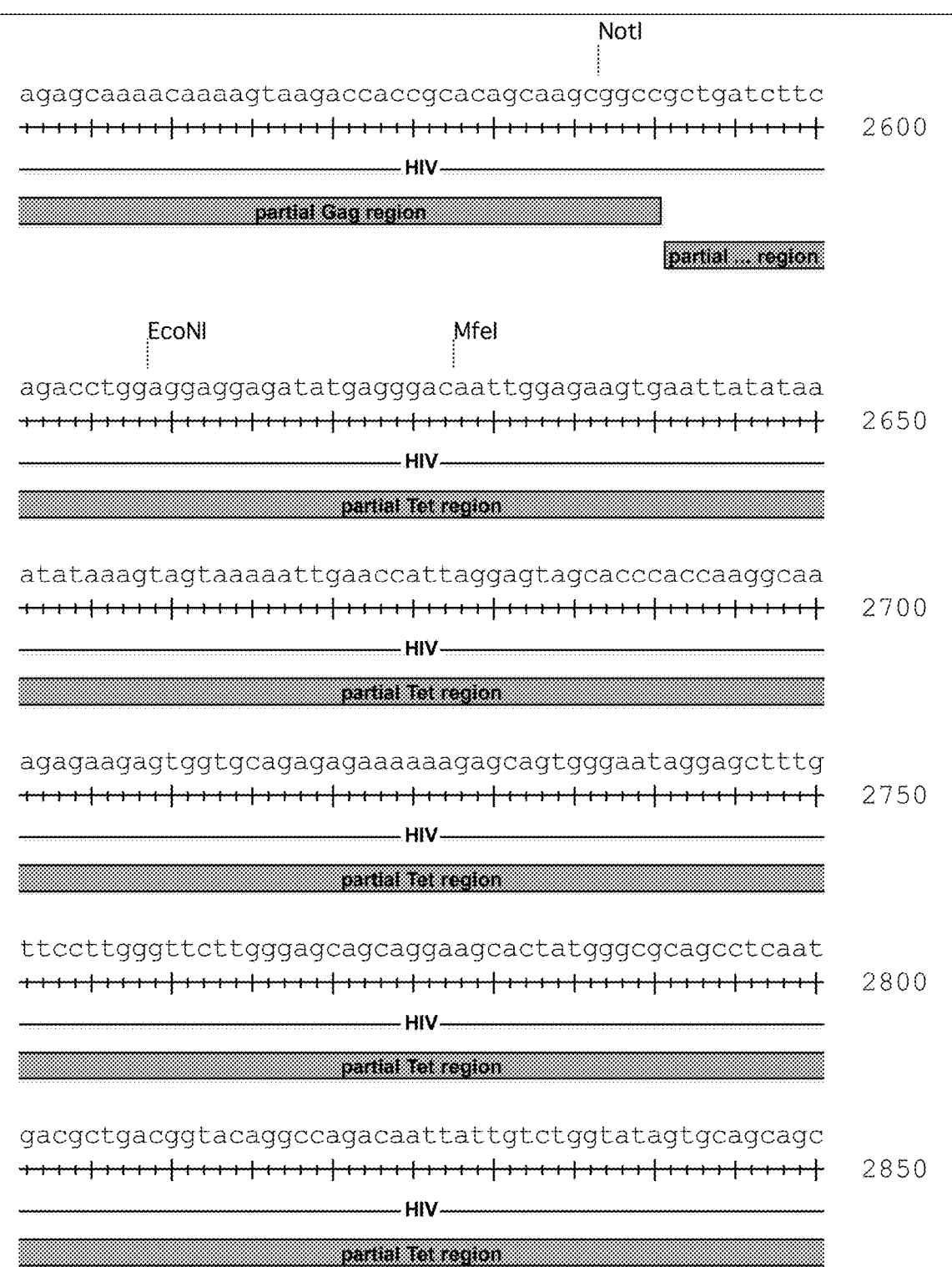
Figure 4B:
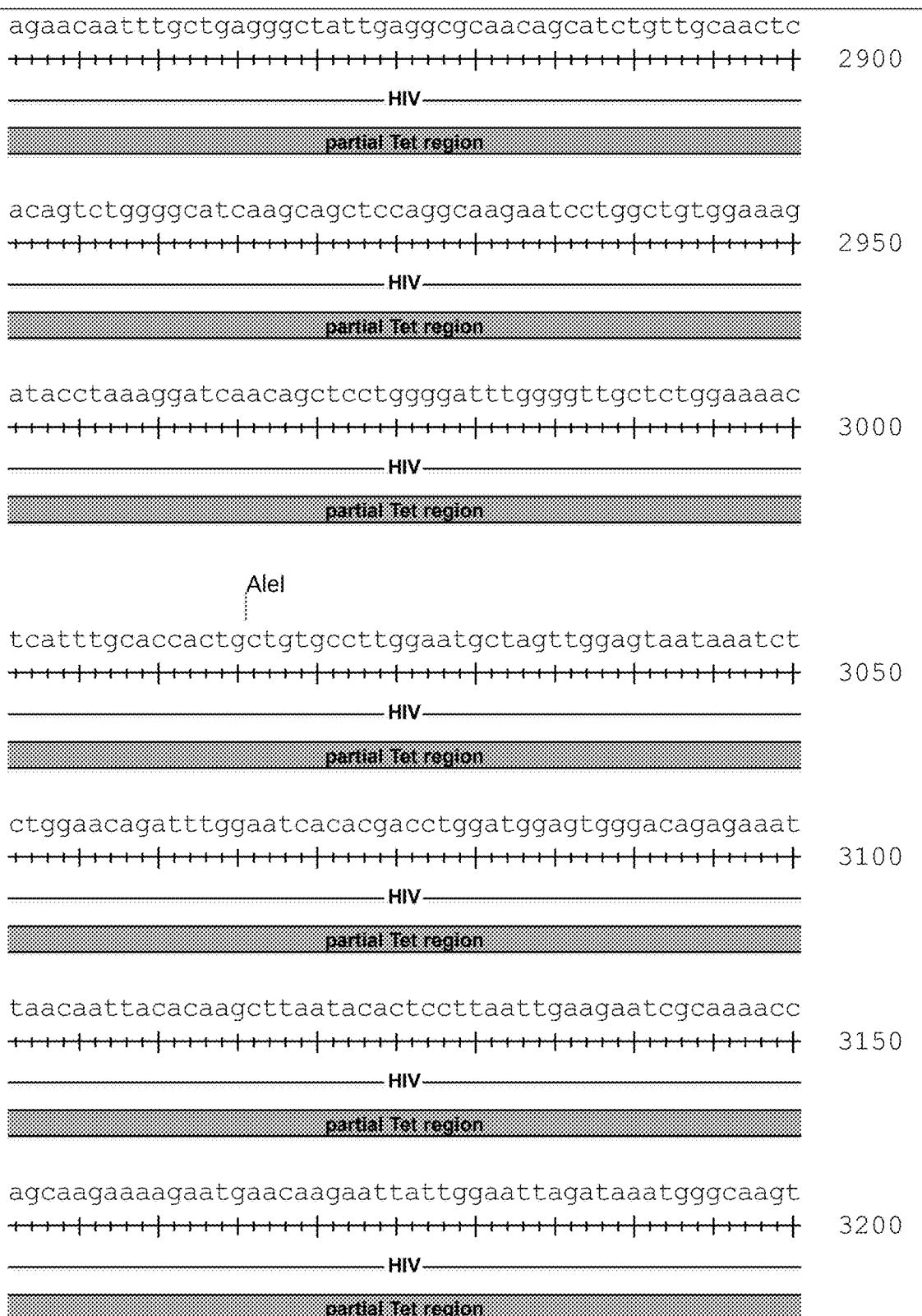
Figure 4B:
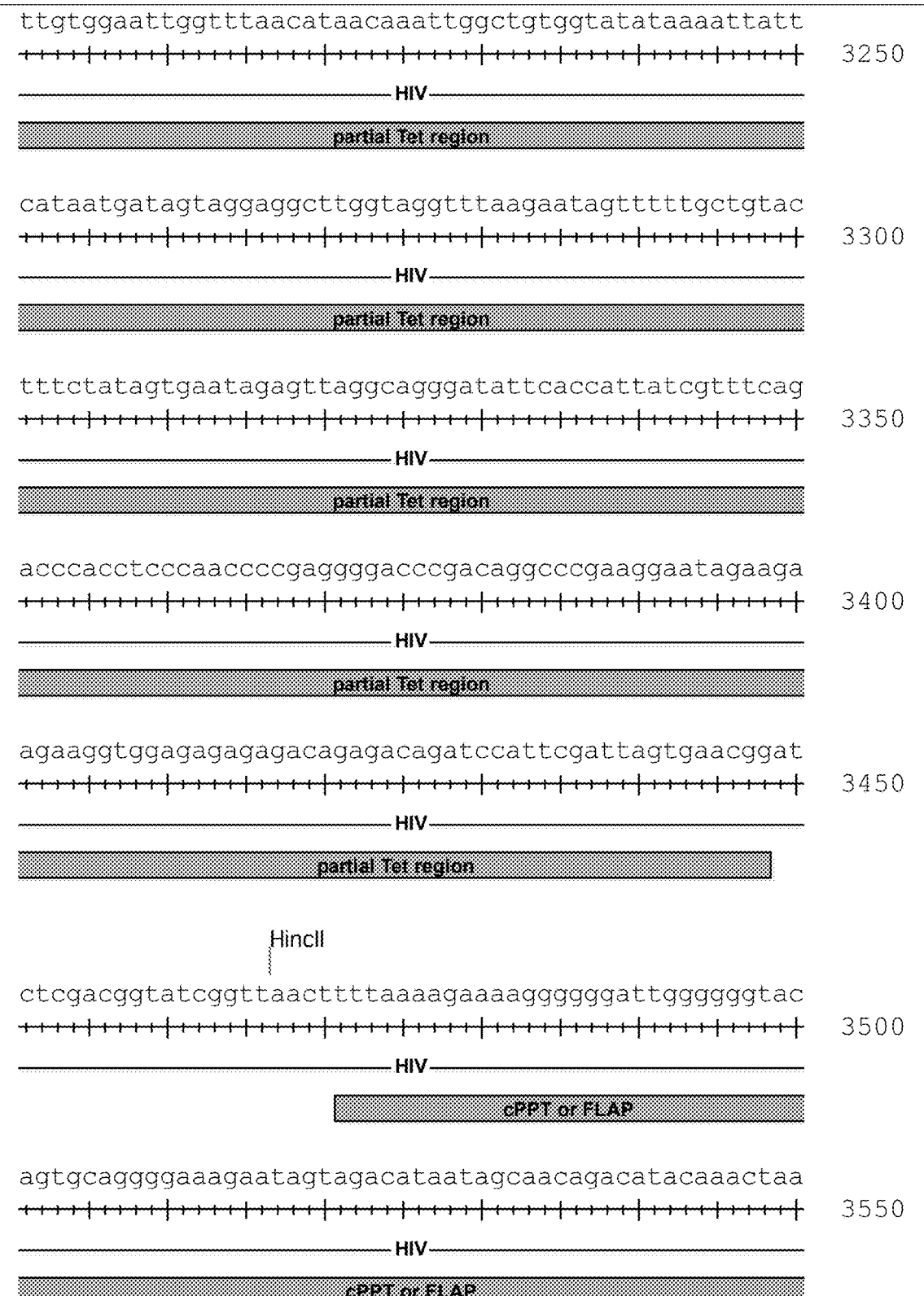
Figure 4B:
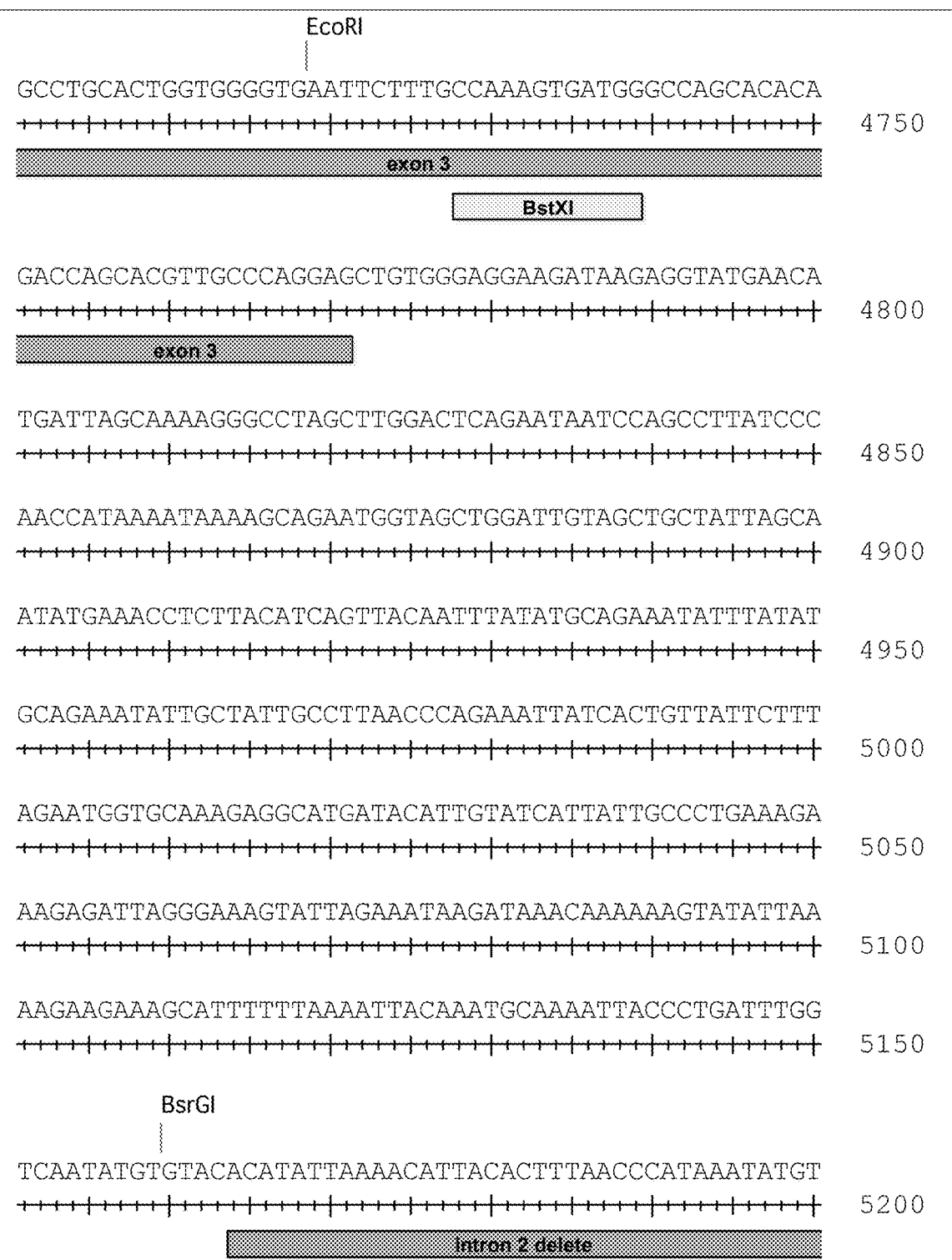
Figure 4B:
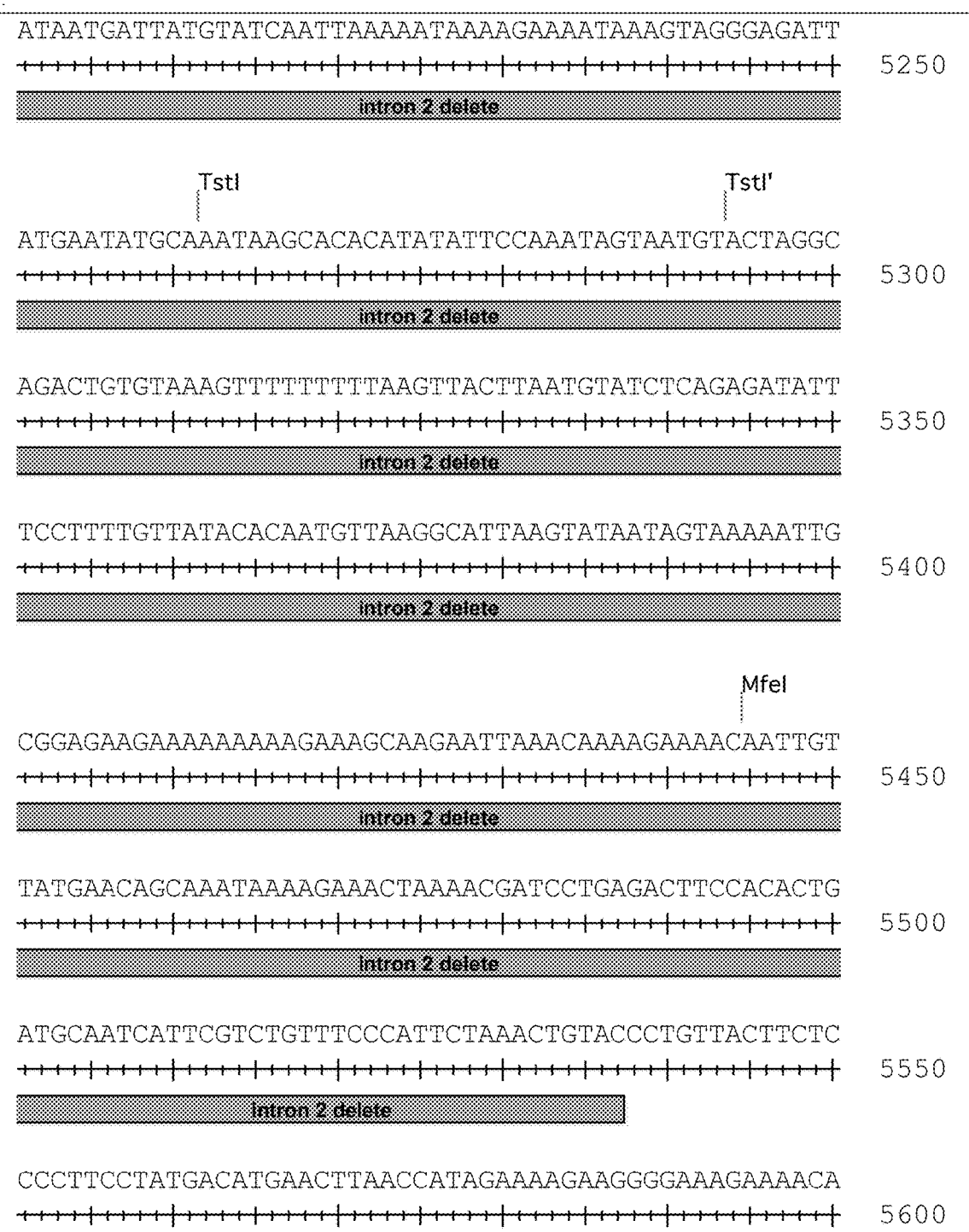
Figure 4B:
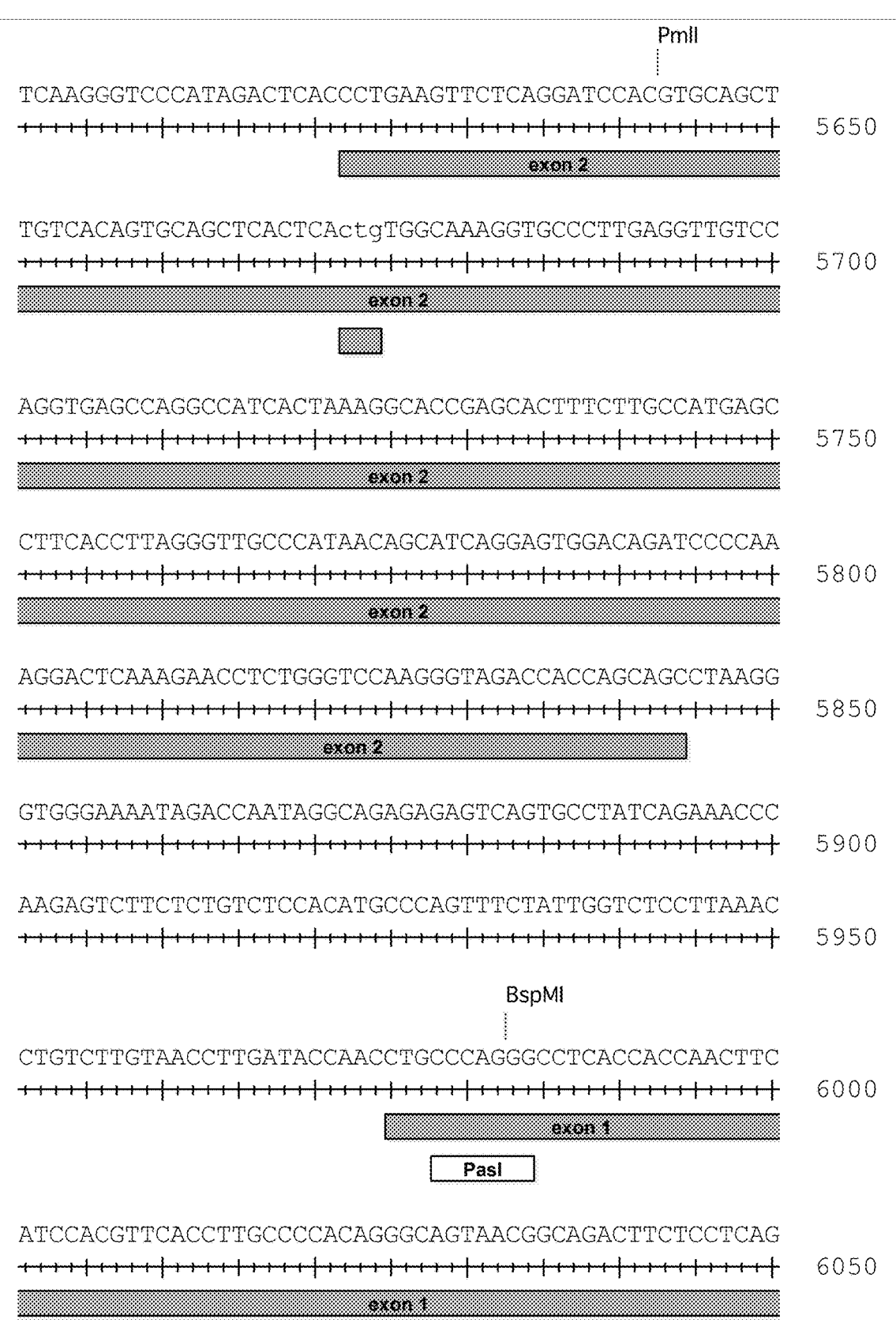
Figure 4B:
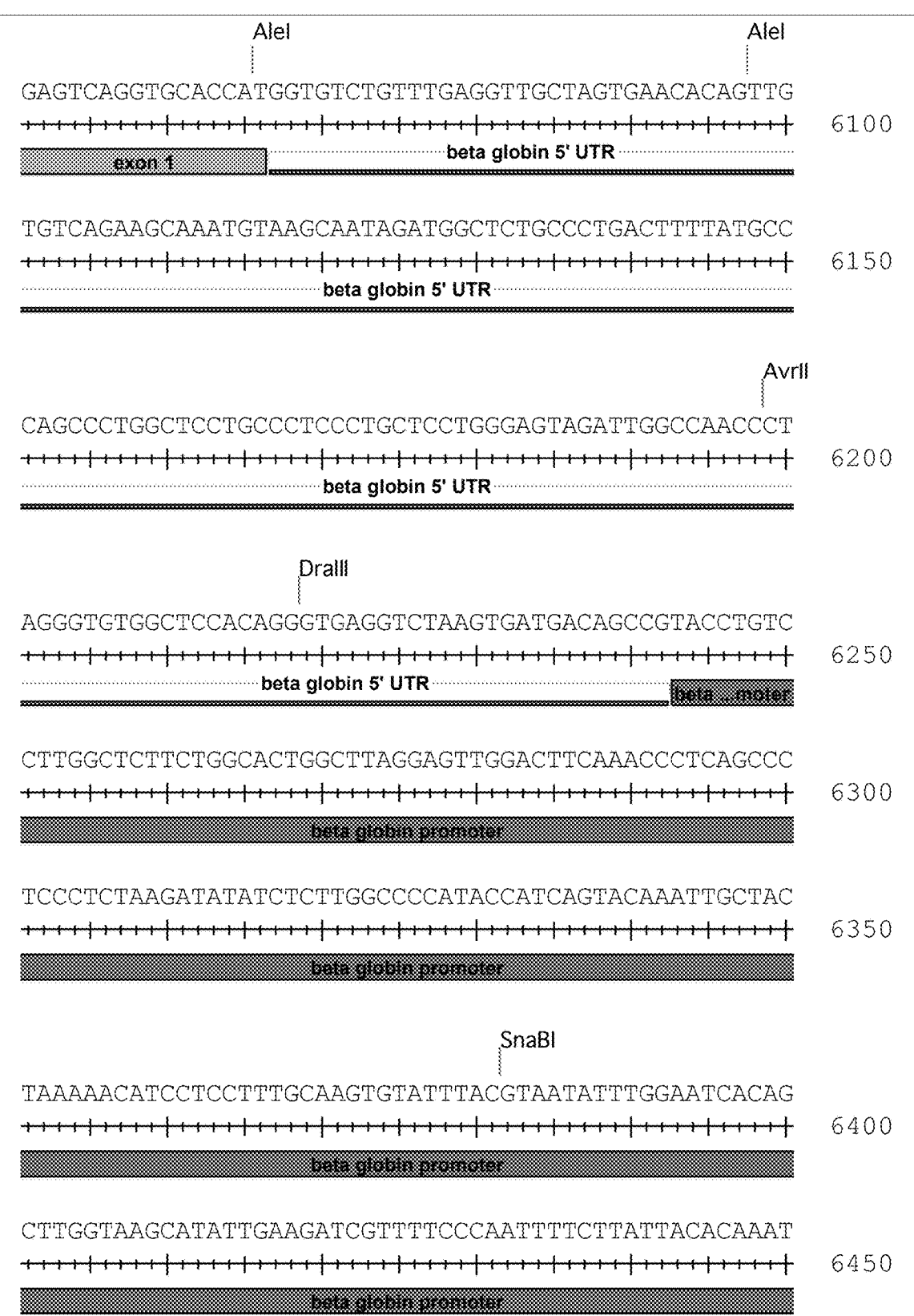
Figure 4B:
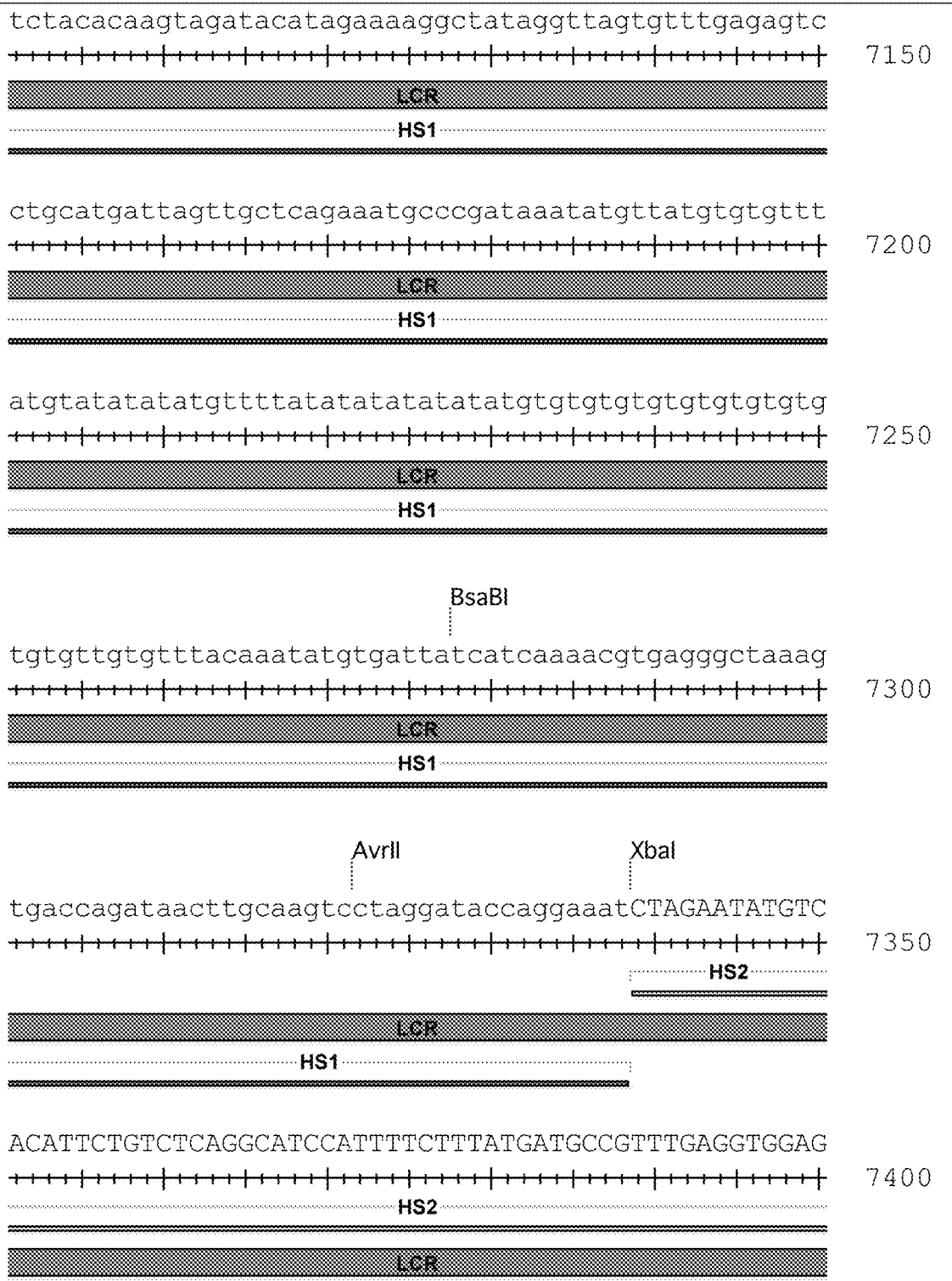
Figure 4B:
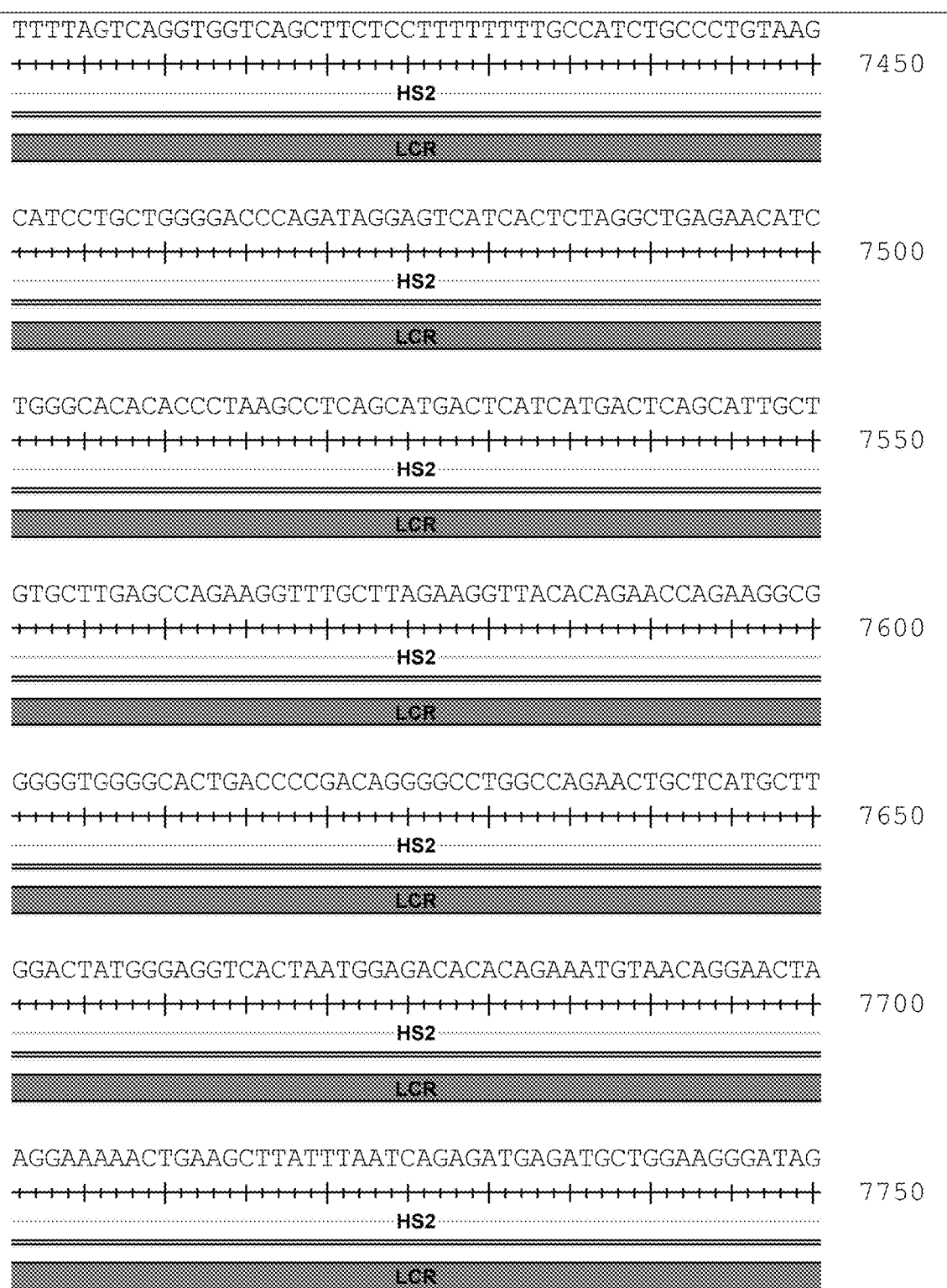
Figure 4B:
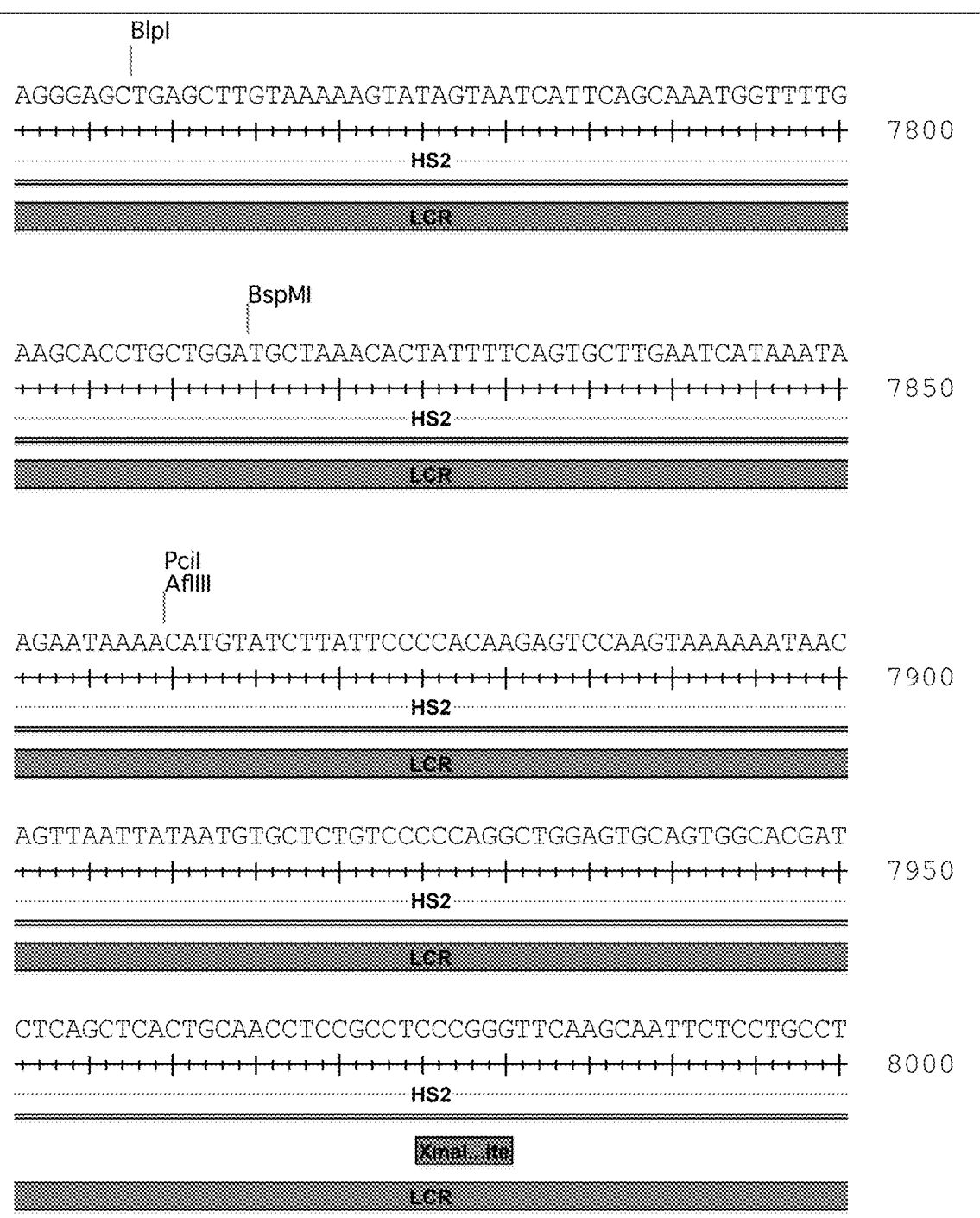
Figure 4B:
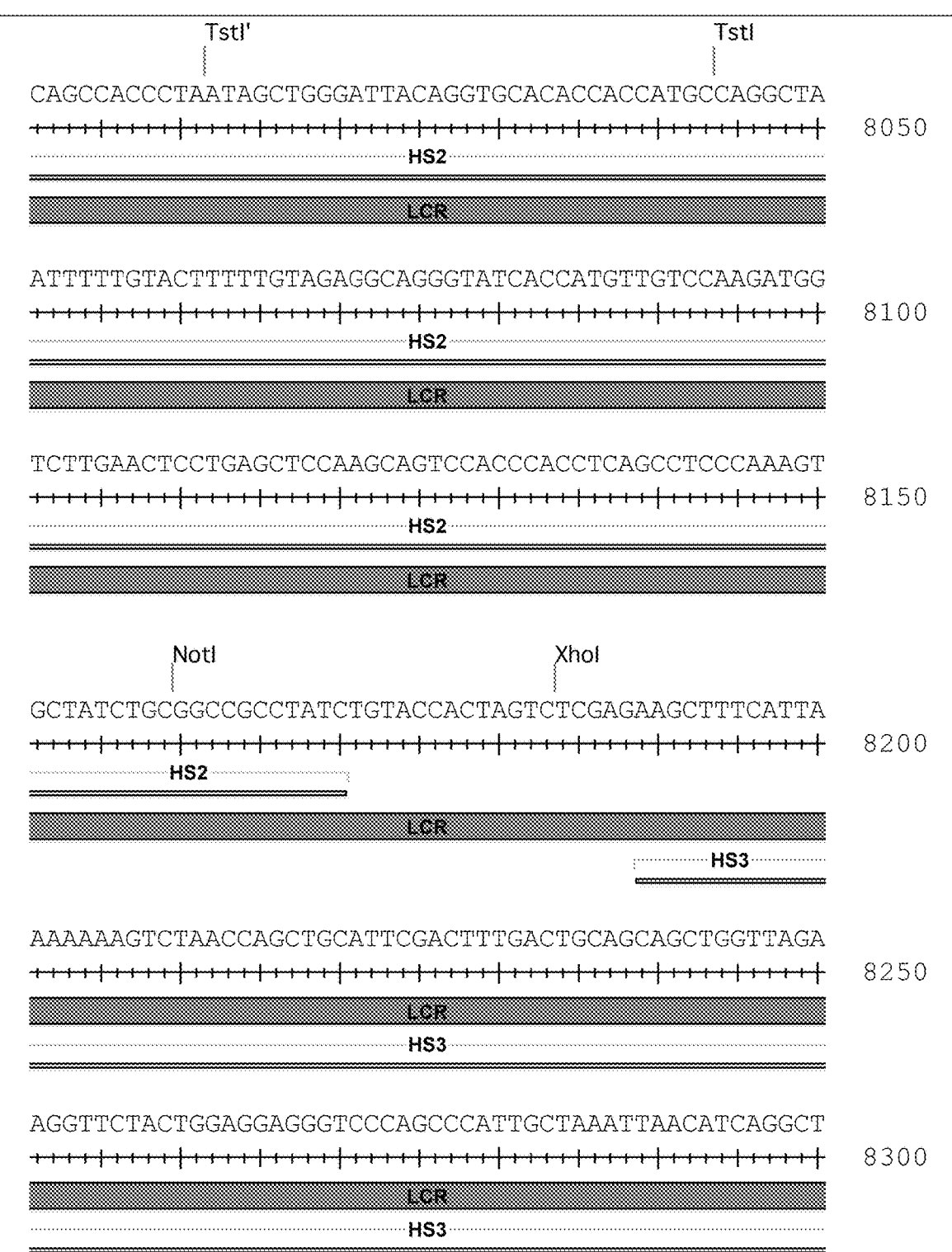
Figure 4B:
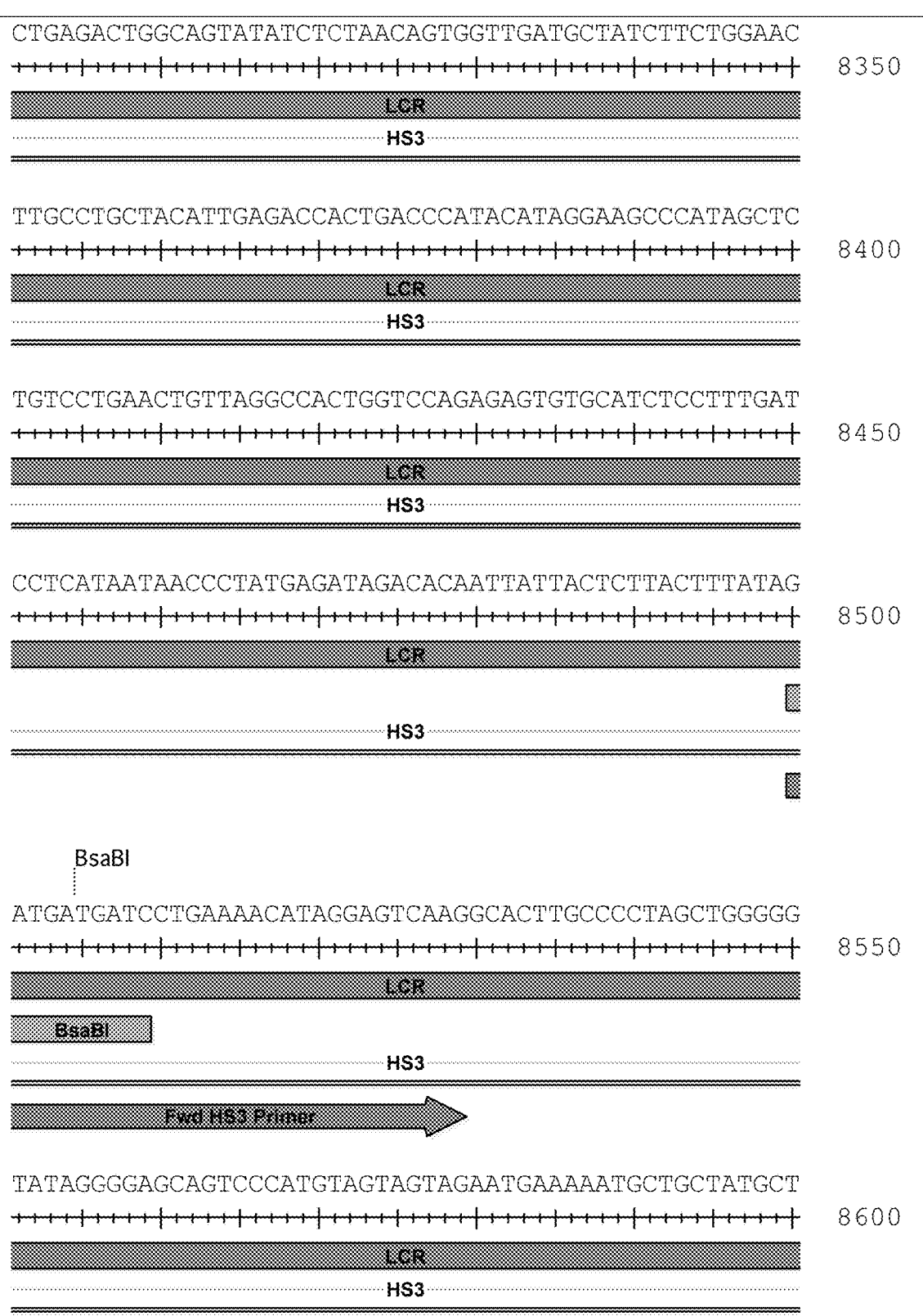
Figure 4B:
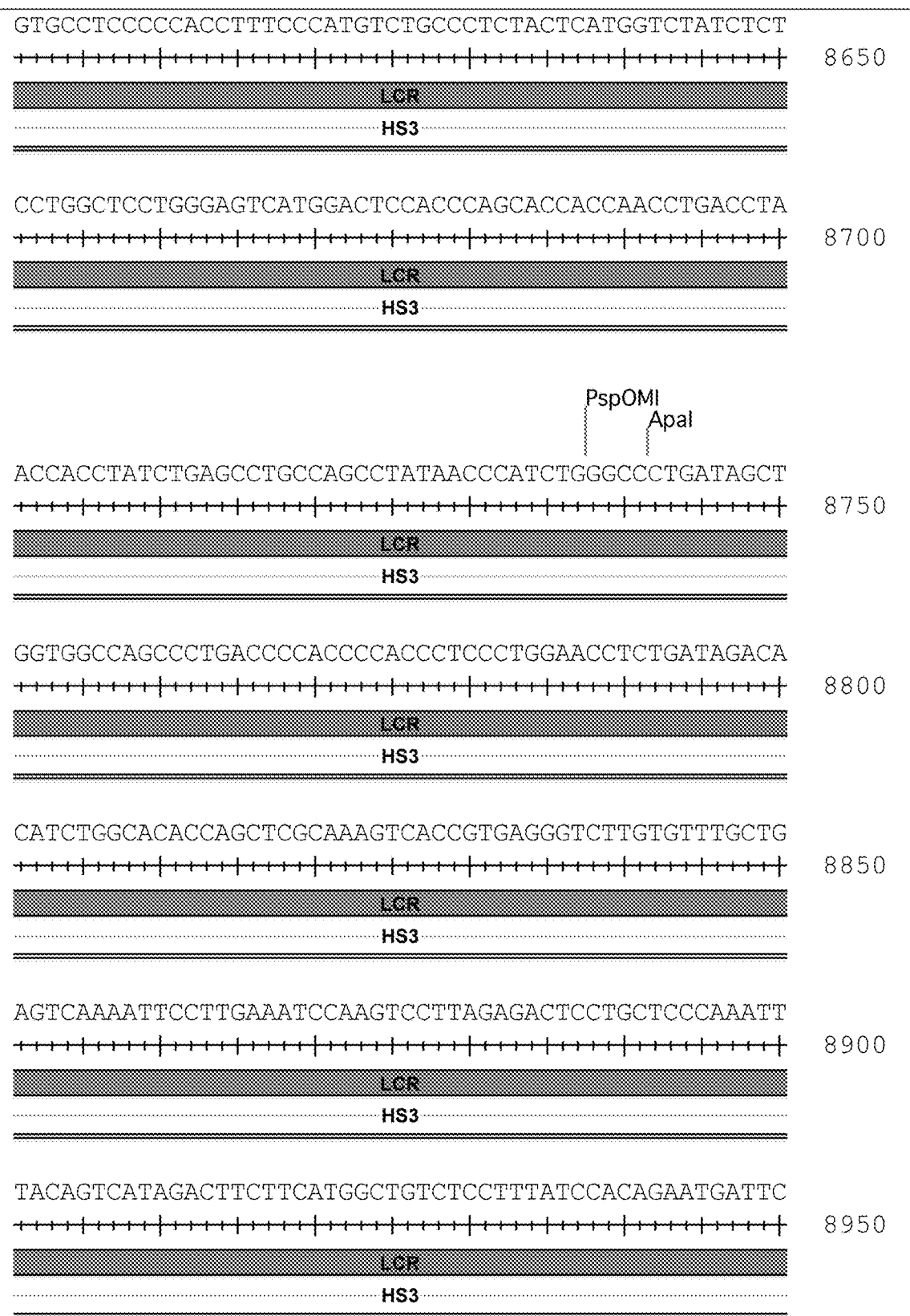
Figure 4B:
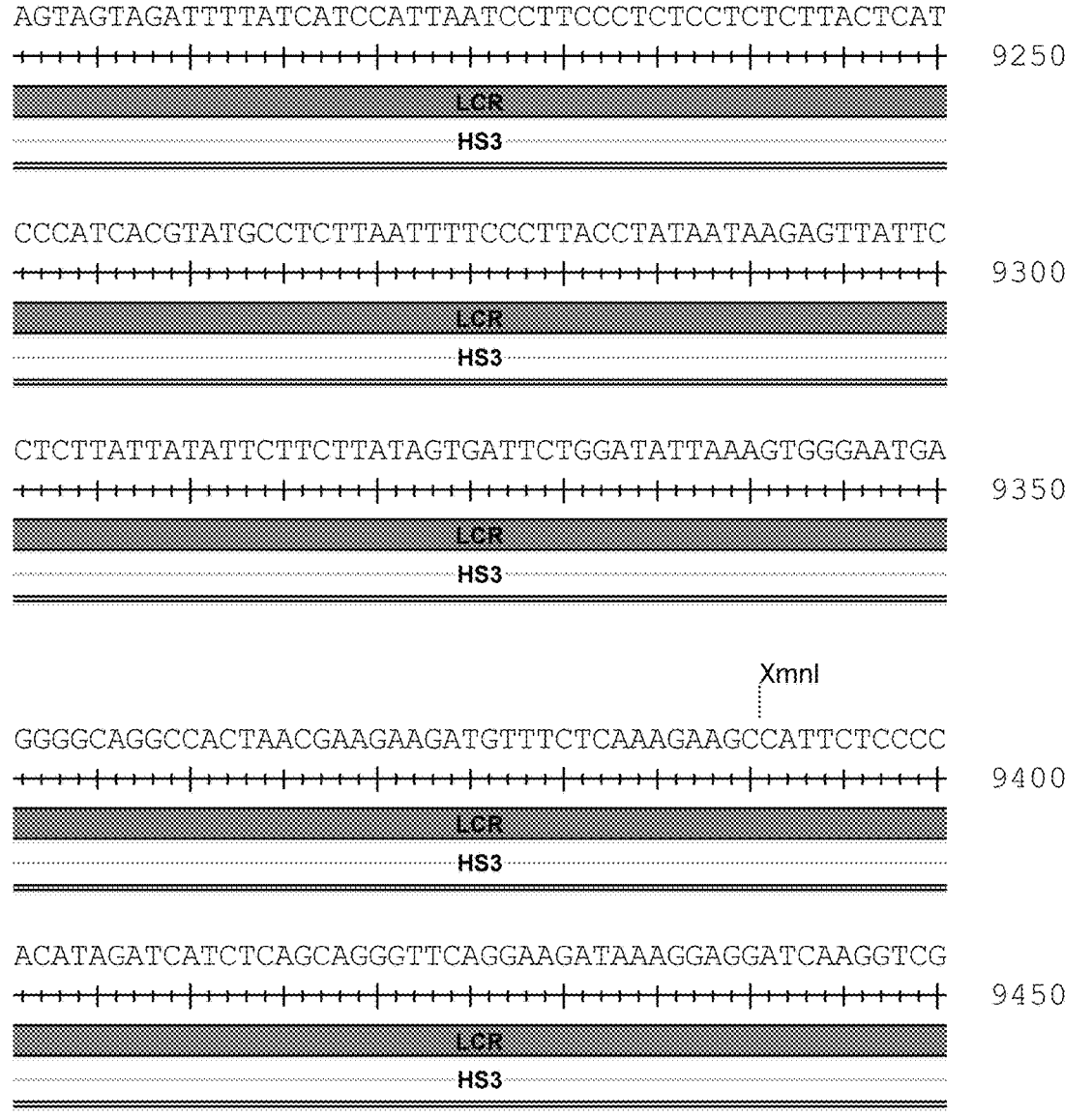
Figure 4B:
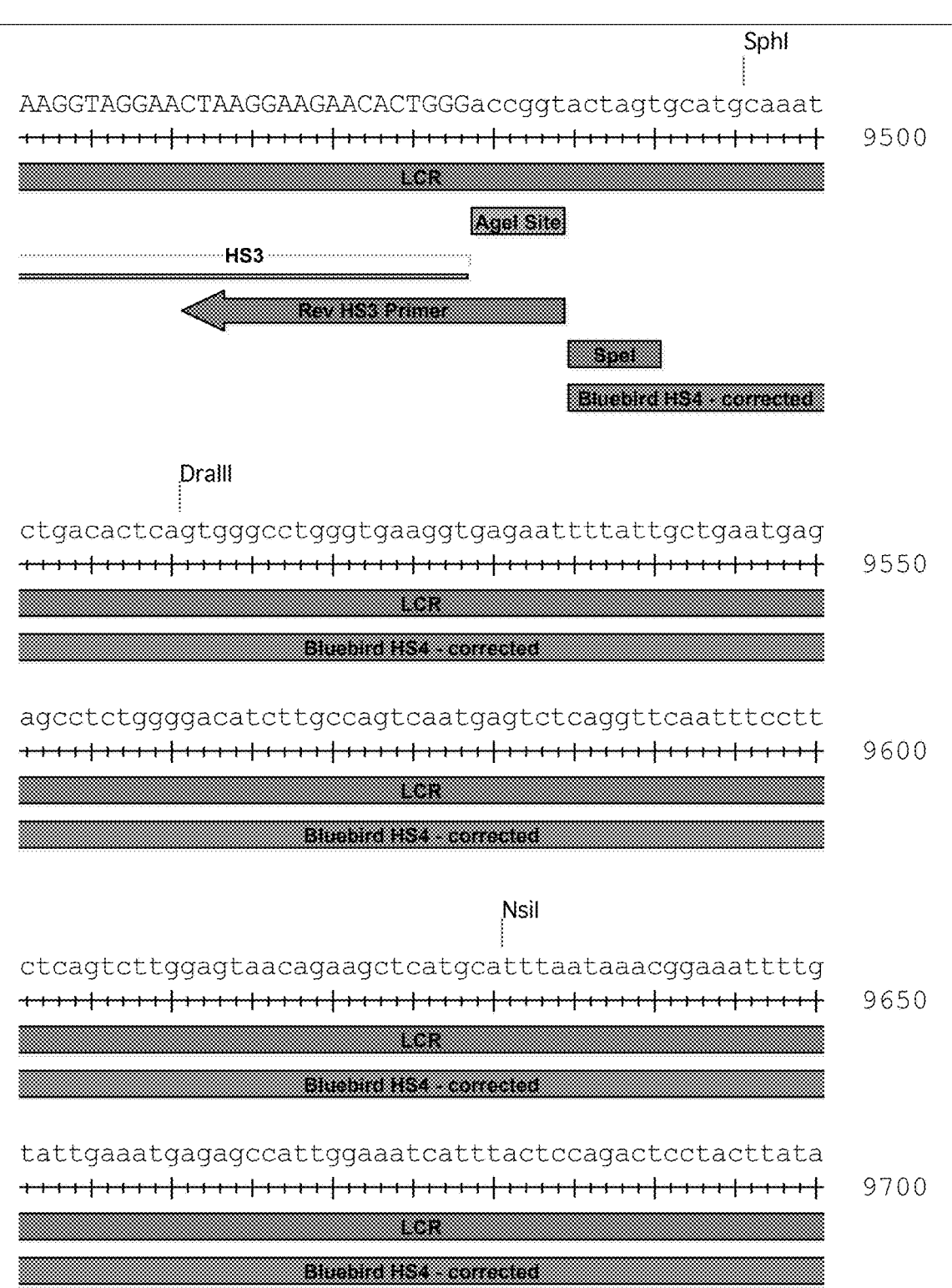
Figure 4B:
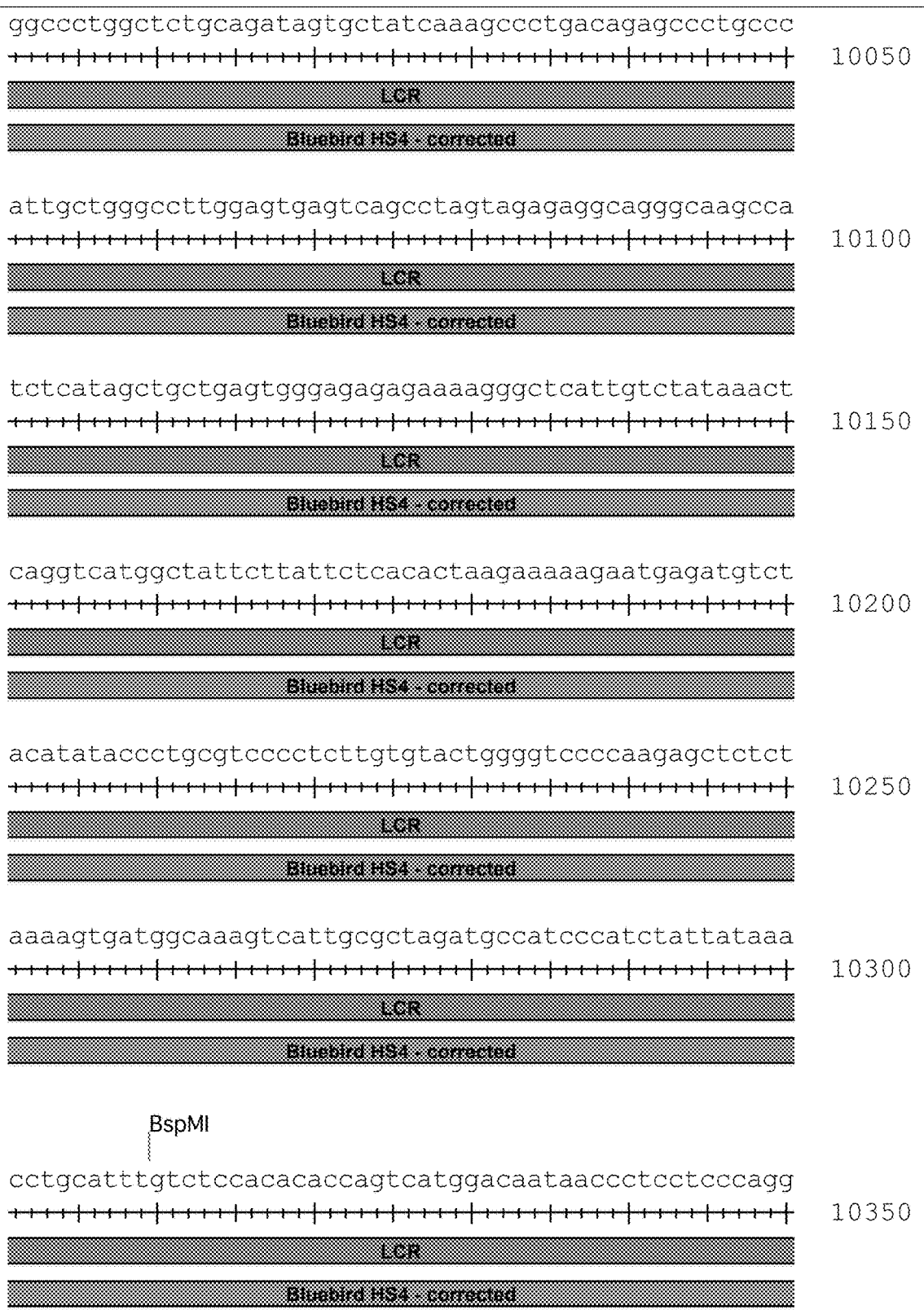
Figure 4B:
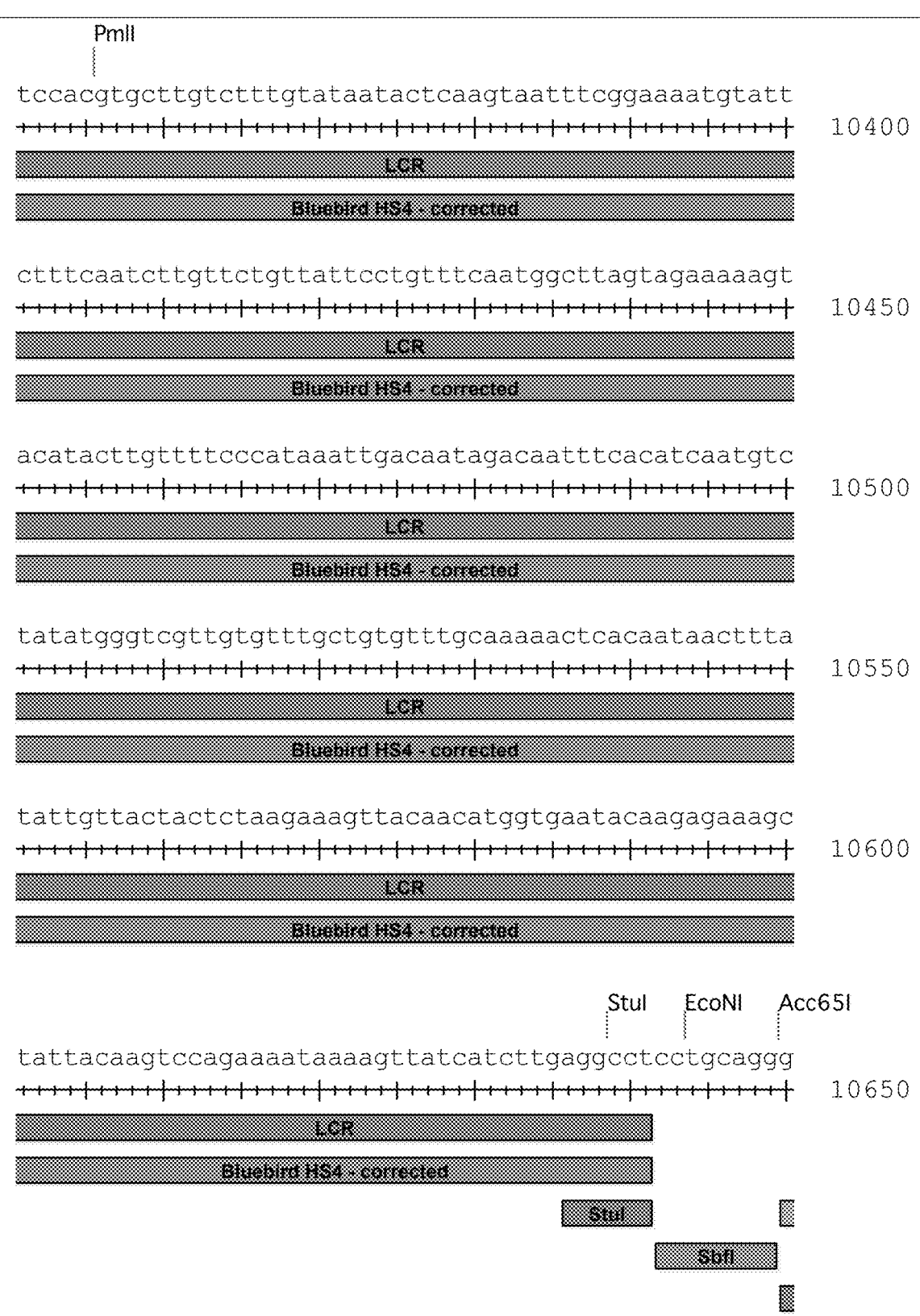
Figure 4B:
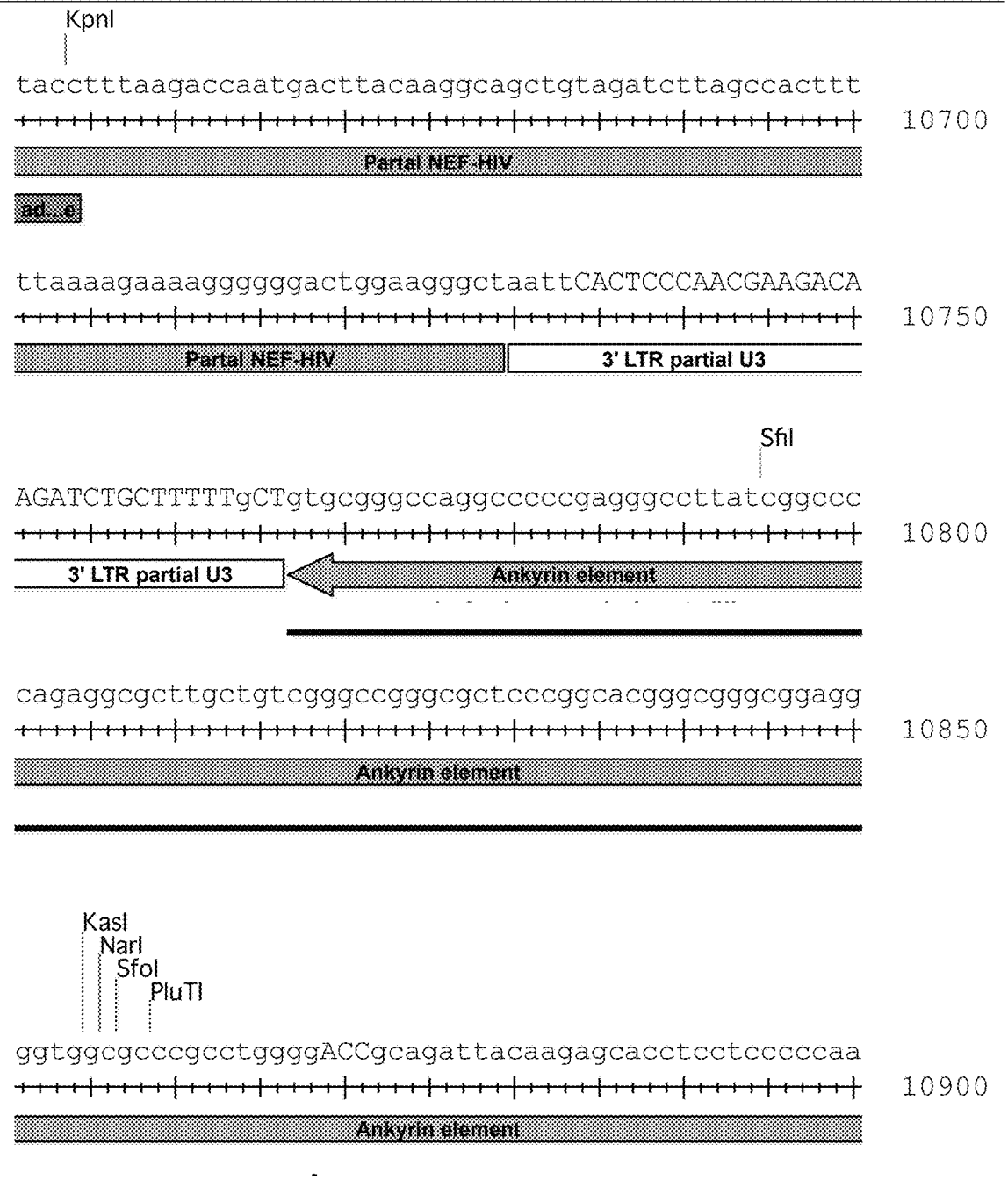
Figure 4B:
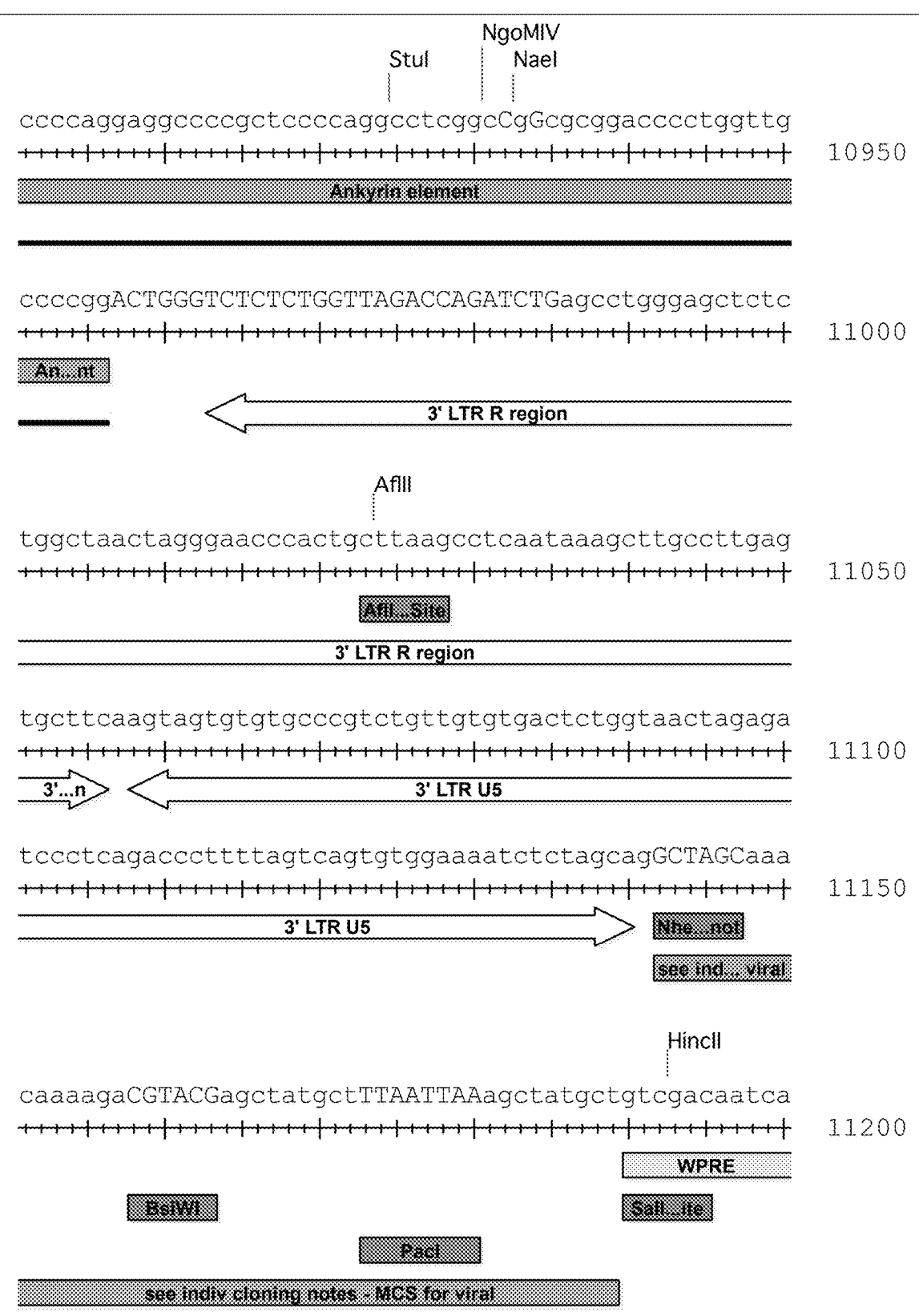
Figure 4B:
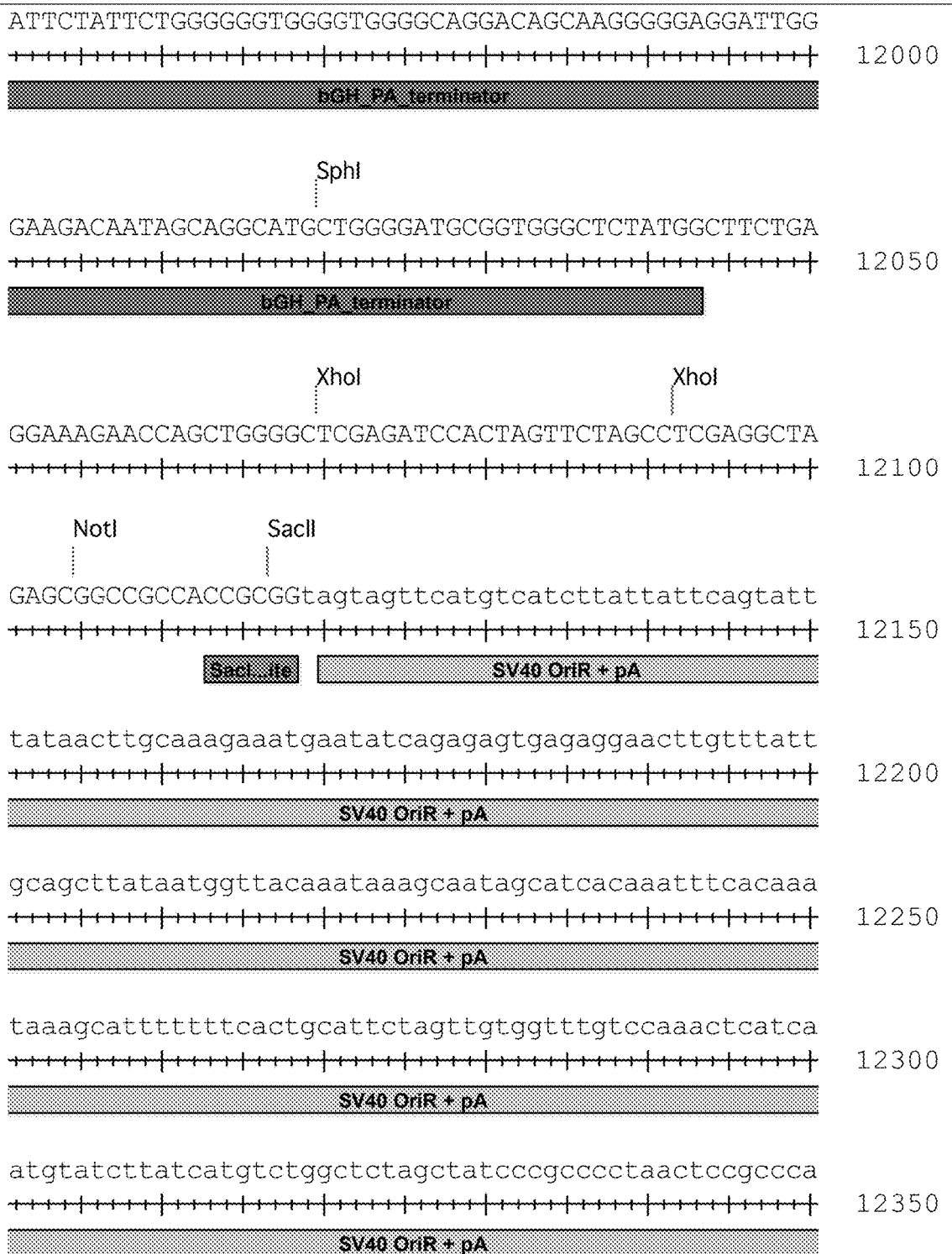
Figure 4B:
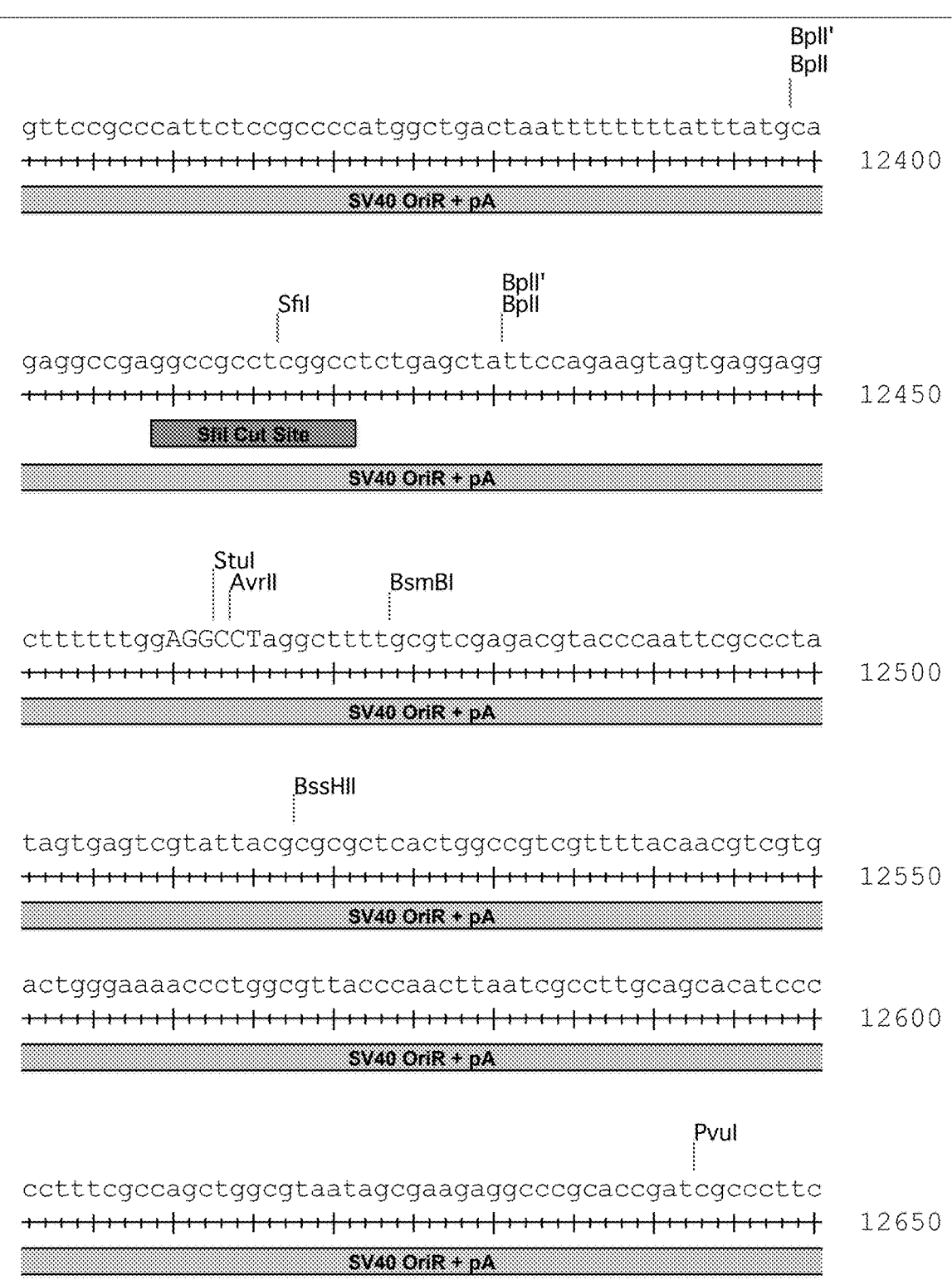
Figure 4B:
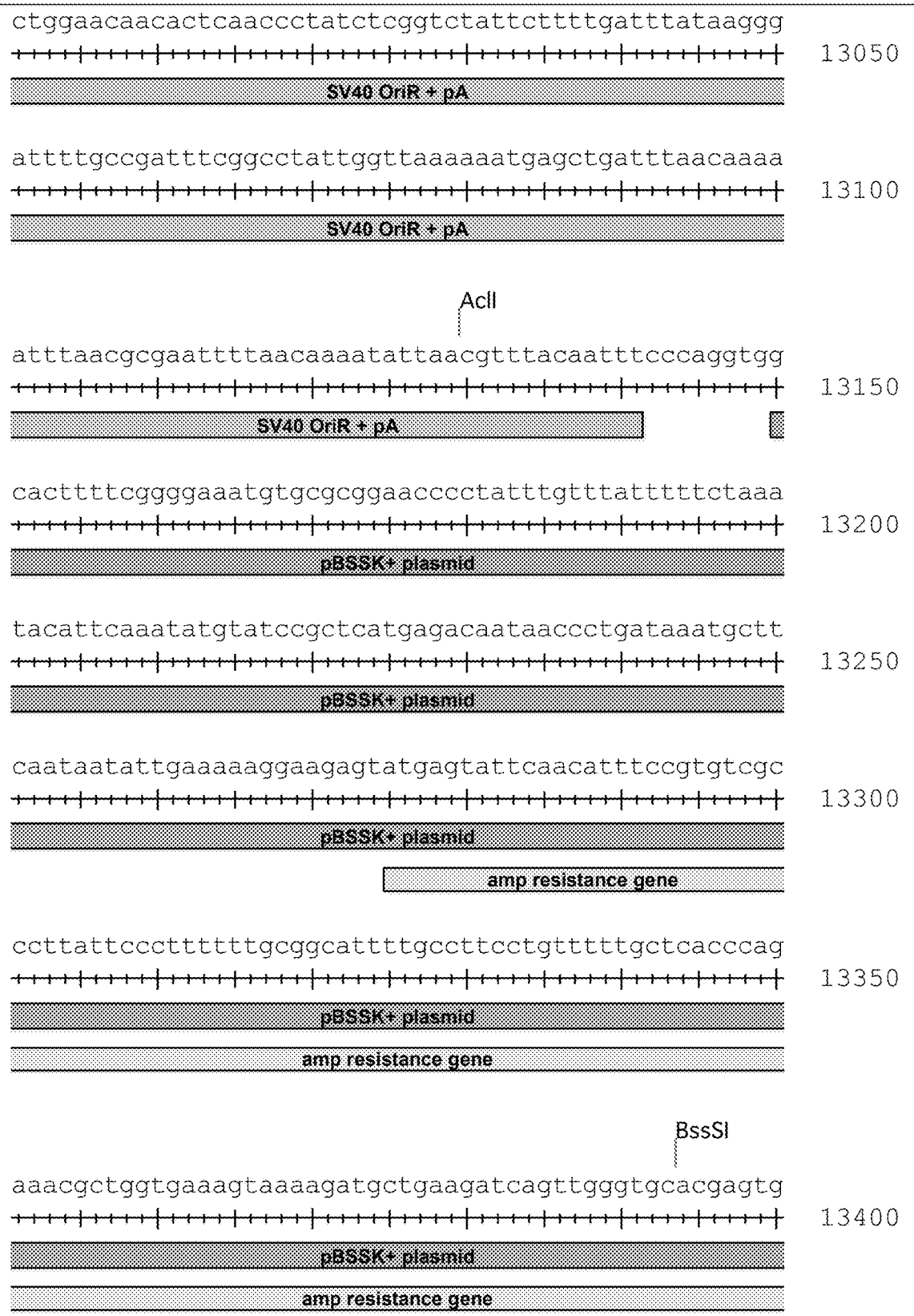
Figure 4B:
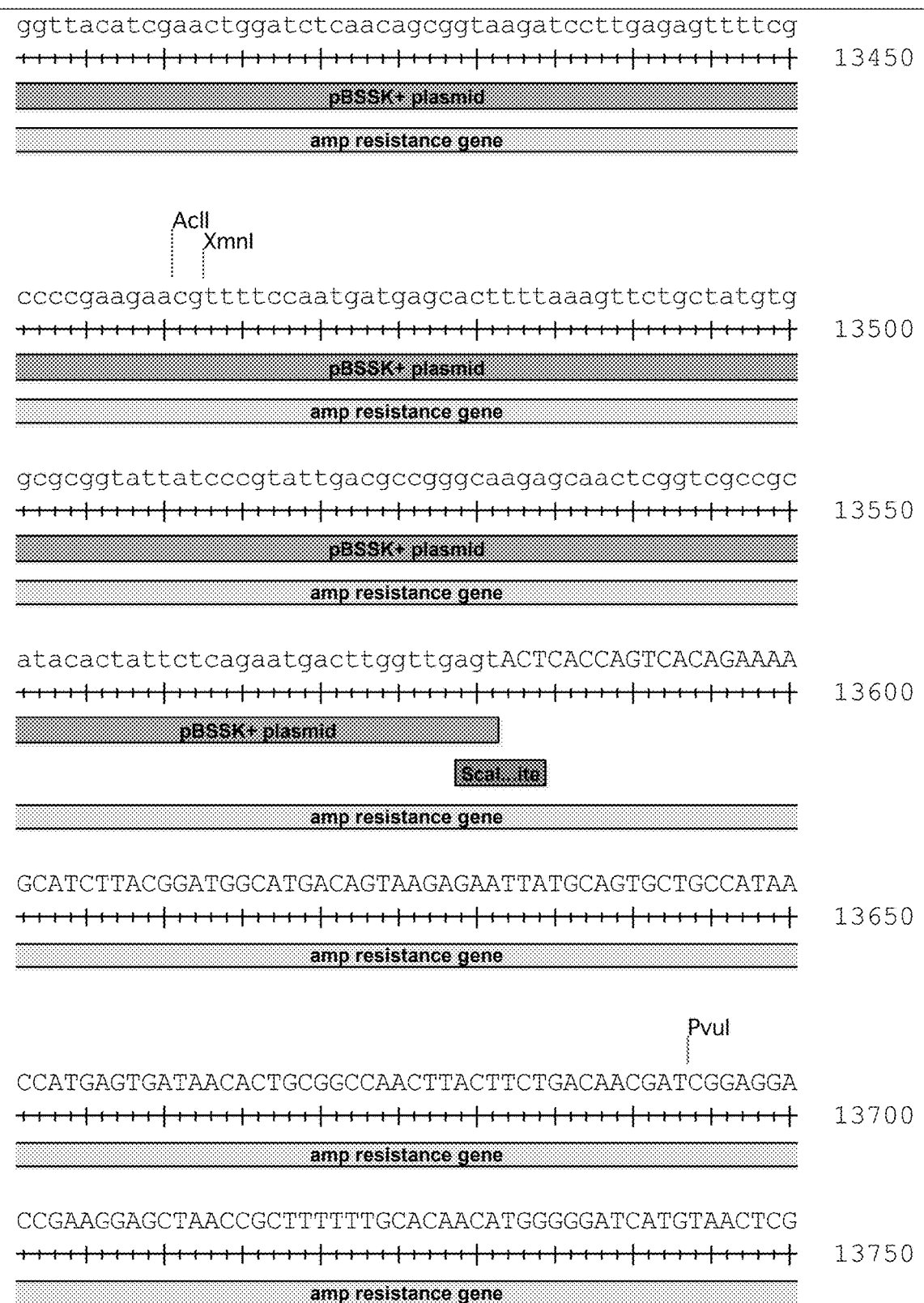
Figure 4B:
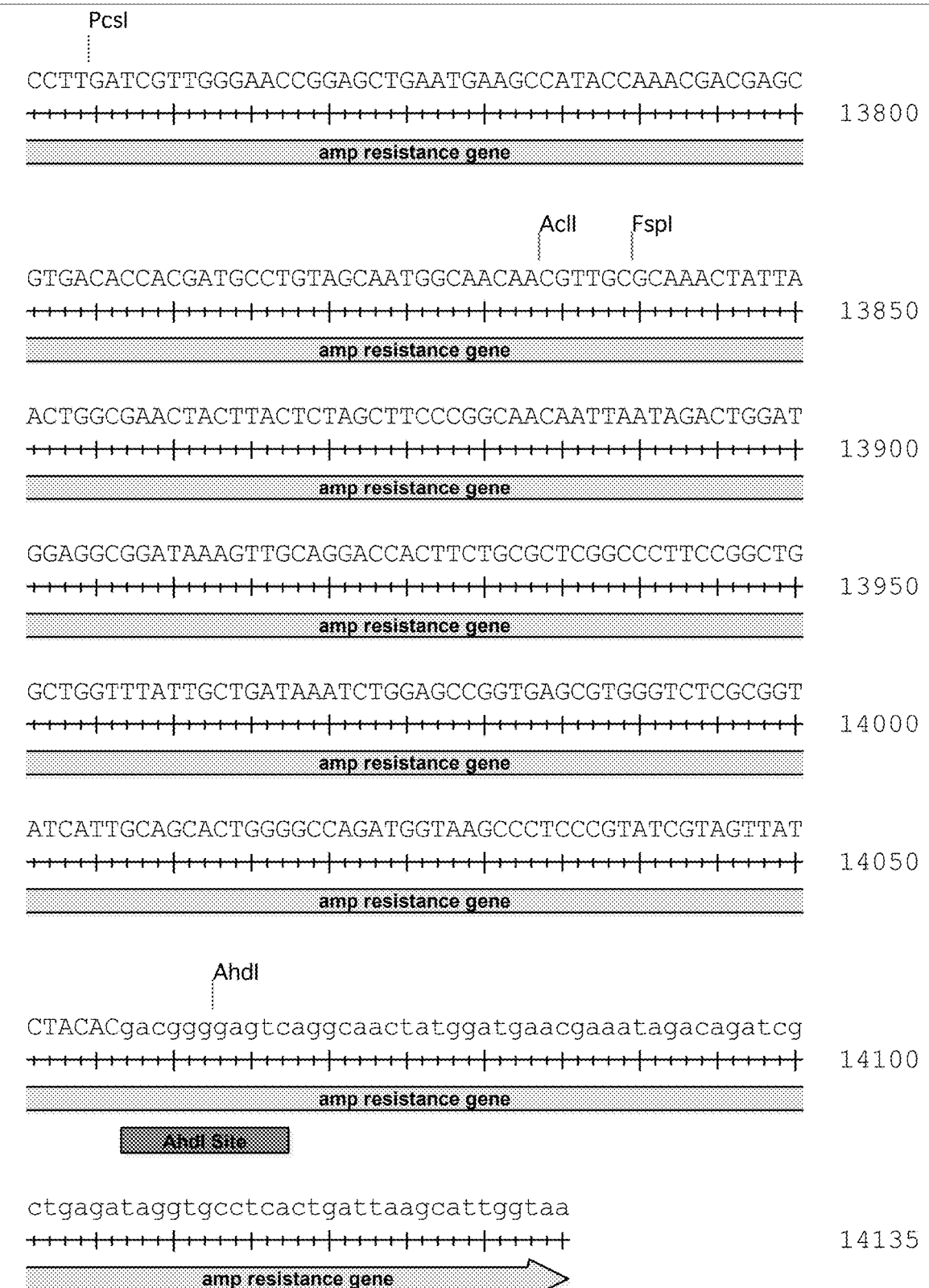

FIG. 4A provides a graphic map of ALS17. FIG. 4B provides an annotated sequence of ALS17 (SEQ ID NO: 1).

Figure 5:
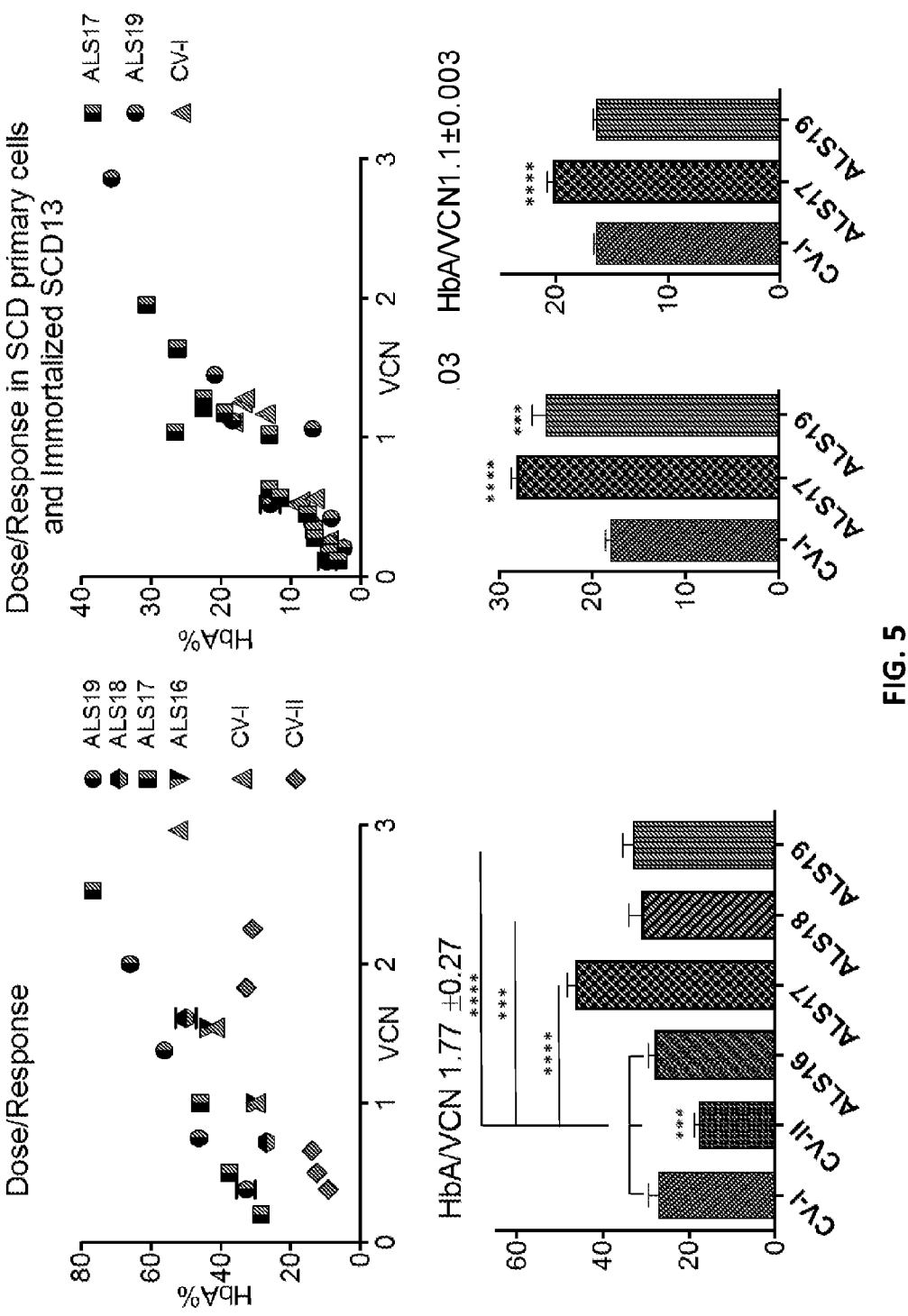

FIG. 5 provides graphs showing the dose/response analyses obtained plotting integration levels (VCN) against HbA % values in cells treated with CV-I, CV-II versus ALS16-17-18-19 within a range of VCN between 0.25 and 3 in an erythroid progenitor cell line (top left) or in primary erythroblasts isolated from patients and differentiated in vitro (top right) as well as comparative levels of HbA at average VCN=1.77 representing the % of curative-HbA over the of number of viral integrations per cell after transduction with ALS-16, -17, -18, -19, CV-I, and CV-II (bottom, left) and comparative levels of HbA at average VCN=0.5 or 1.1 in SCD specimens treated with CV-I, ALS17 and ALS19 (N=3; one way Anova with Dunnet's multiple comparison test).

Figure 6:
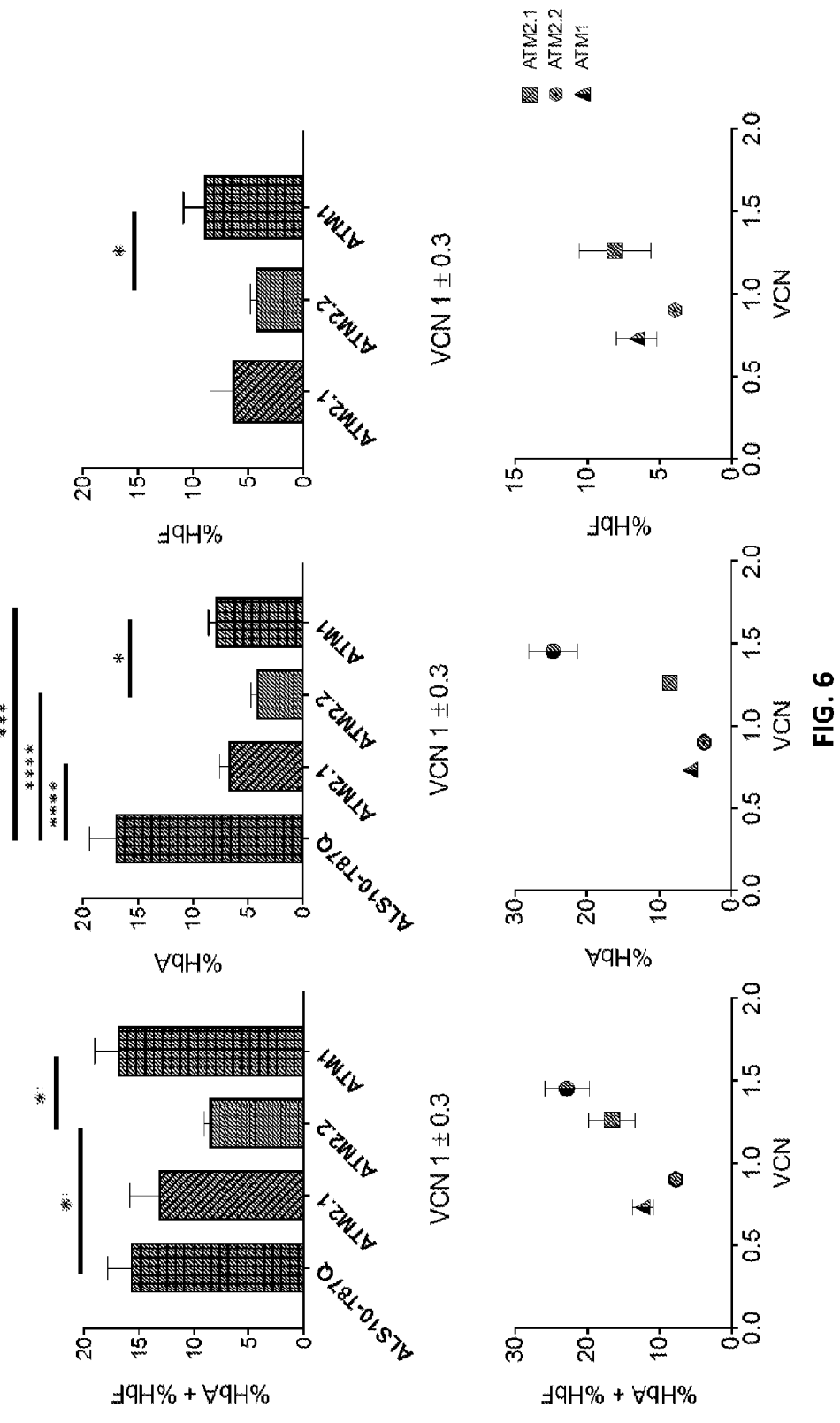

FIG. 6 provides graphs of the expression of HbA+HbF, HbA, and HbF in erythroid progenitor cells transduced with ALS10-T87Q, ATM2.1, ATM2.2, or ATM1 (top row). FIG. 6 also provides graphs of the expression of HbA+HbF, HbA, and HbF in erythroid progenitor cells transduced with ALS10-T87Q, ATM2.1, ATM2.2, or ATM1 as a factor of VCN (bottom row).

Figure 7:
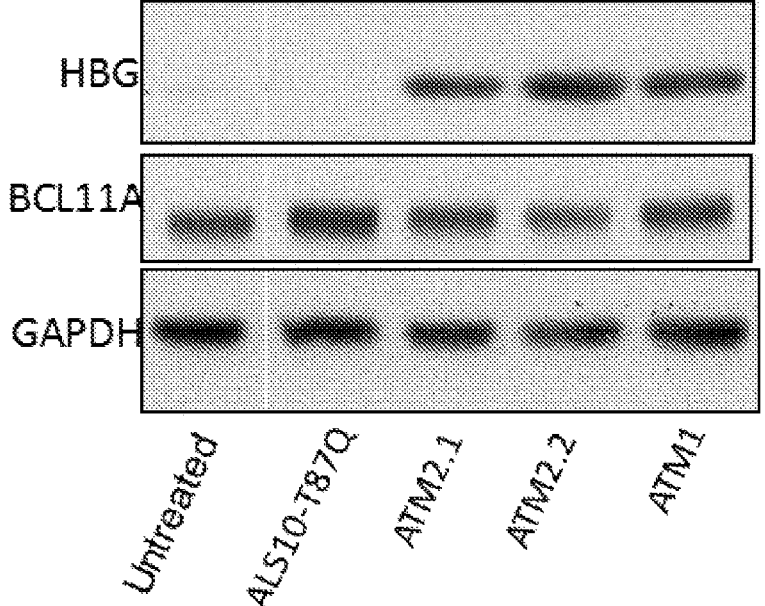

FIG. 7 provides images of Western blot analyses showing expression of BCL11A protein levels and gamma-globin levels (HBG) in erythroid progenitor cells transduced with ALS10-T87Q, ATM2.1, ATM2.2, or ATM1. GADPH is presented as a control.

Figure 8A:
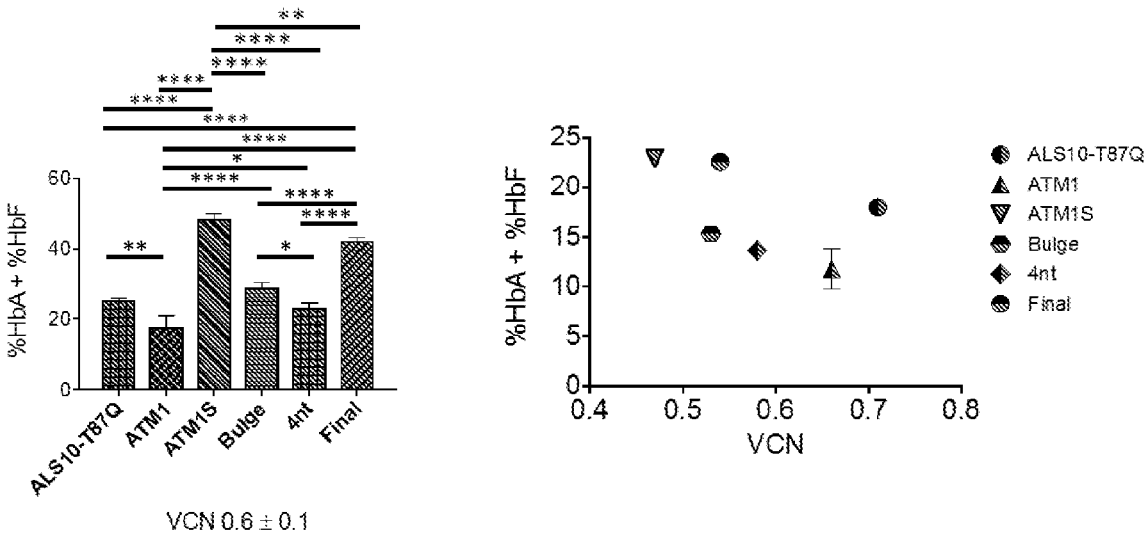
Figure 8B:
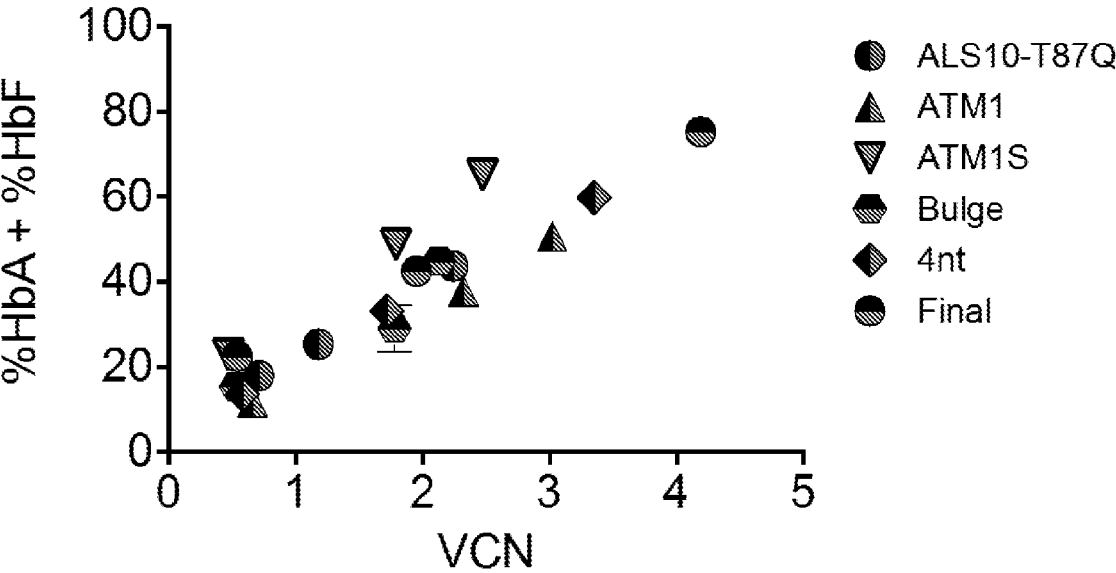
Figure 8C:
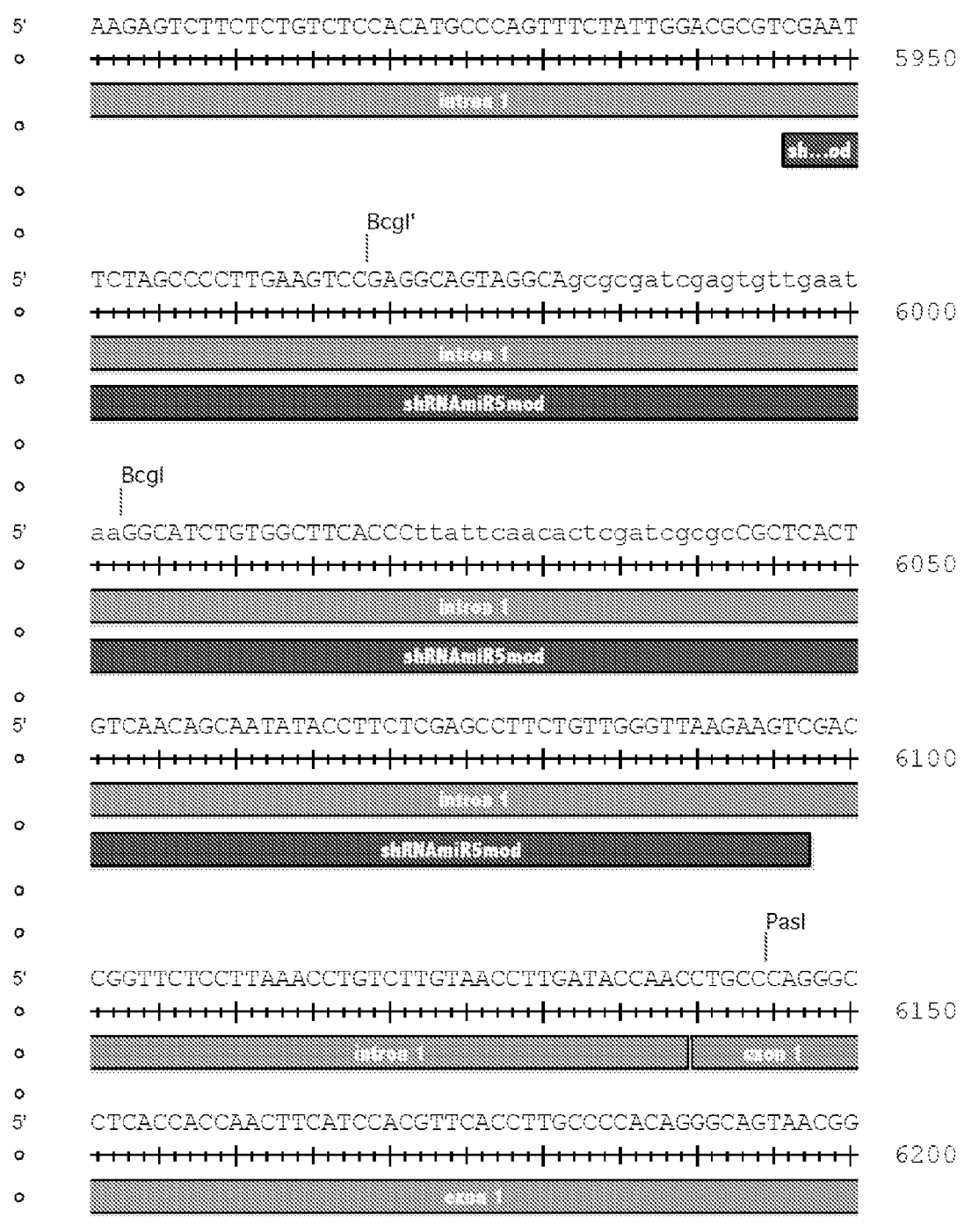

FIG. 8A provides graphs of the expression of HbA+HbF in erythroid progenitor cells transduced with ALS10-T87Q, ATM1, ATM1S, bulge (between stem and basal stem), 4nt (4 nt modification of loop) or Final (AT1S+4nt+Bulge). FIG. 8A also provides a graph of the expression of HbA+HbF in erythroid progenitor cells transduced with ALS10-T87Q, ATM1, ATM1S, bulge, 4nt, or Final at VCN 0.6. FIG. 8B also provides a graph of the expression of HbA+HbF in erythroid progenitor cells transduced with ALS10-T87Q, ATM1, ATM1S, bulge, 4nt, or Final as a factor of VCN. FIG. 8C provides an annotated sequence of shRNAmiR5mod within intron 1 (SEQ ID NO: 2).

Figure 9A:
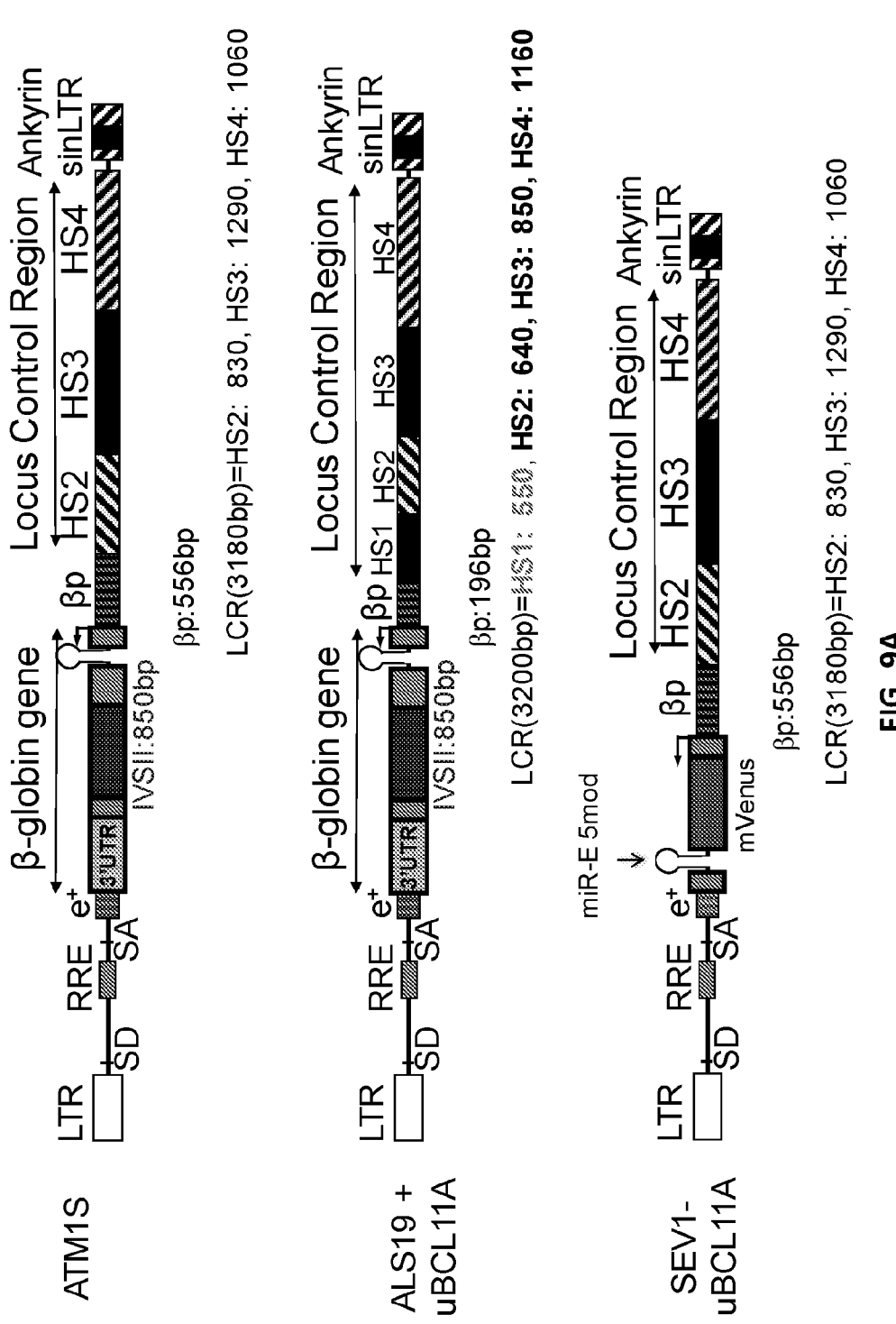
Figure 9B:
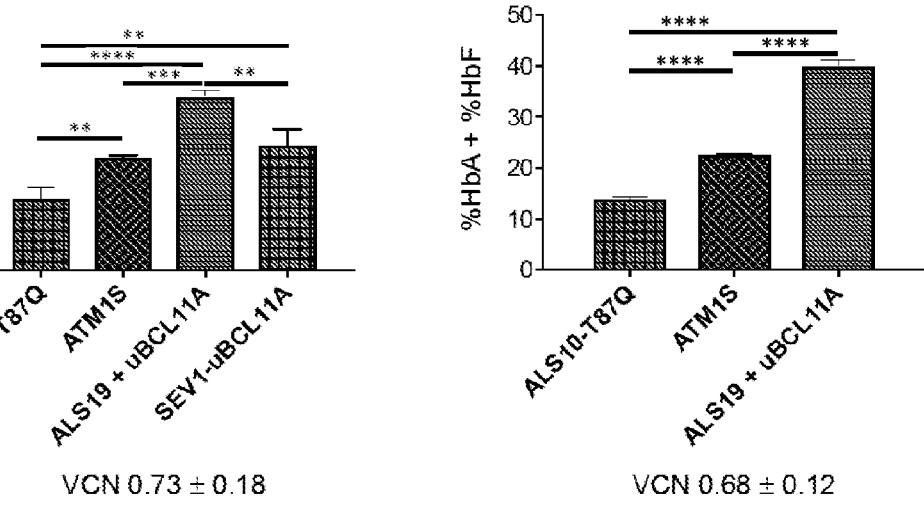
Figure 9C:
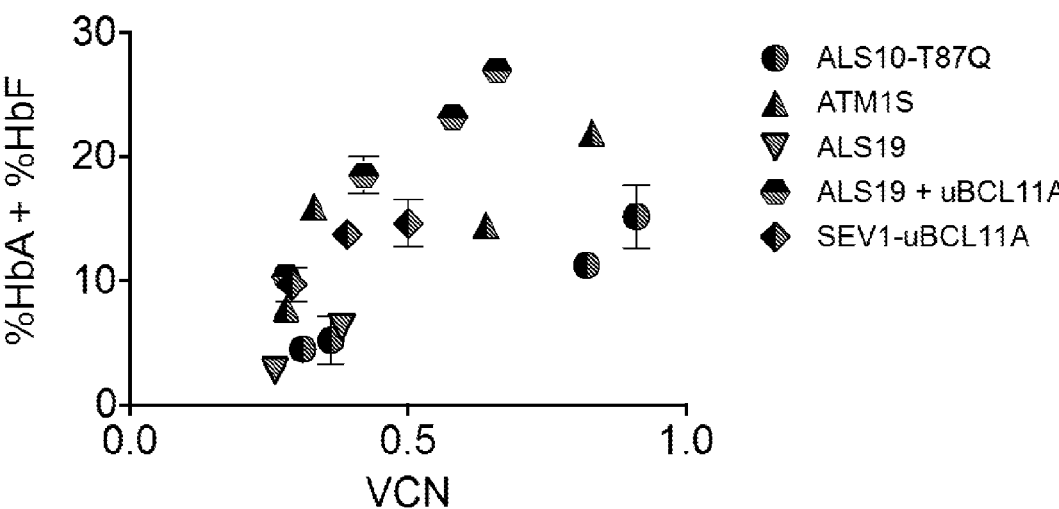

FIG. 9A provides schematics of ATM1S, ALS19+ uBCL11A, and SEV1-uBCL11A. FIG. 9B provides graphs of the expression of HbA+HbF in SCD primary cells transduced with ALS10-T87Q, ATM1S, ALS19+uBCL11A, and SEV1-uBCL11A. FIG. 9C also provides a graph of the expression of HbA+HbF in erythroid progenitor cells transduced with ALS10-T87Q, ATM1S, ALS19+uBCL11A, and SEV1-uBCL11A as a factor of VCN.

Figure 10D:
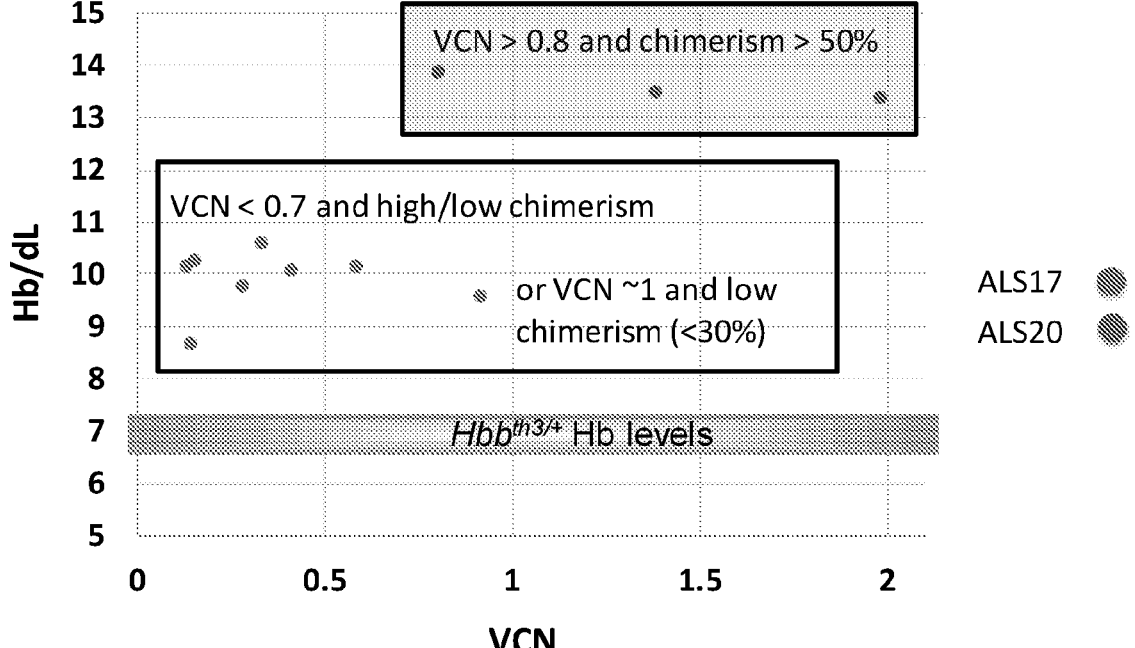

FIG. 10A provides a dose/response analyses obtained plotting integration levels (VCN) against HbA % values in cells treated with CV-I, CV-II, CV-III versus ALS16-17-18-19-20 within a range of VCN between 0.25 and 3 in HUDEPs cells. On right, linear regression analyses for comparison of HbA increase at integration=1 VCN in HUDEPs. FIG. 10B provides a dose/response analyses obtained plotting integration levels (VCN) against HbA % values in cells treated with CV-I versus ALS17-19-20. On right, linear regression analyses for comparison of HbA increase at integration=1 VCN in SCD primary cells. FIG. 10C shows the hemoglobin A synthesis in erythroid cells from patients with β0/0 thalassemia, after transduction with beta-LVs ALS20. FIG. 10D provides a normalization of erythropoiesis in Hbb$^{th3/+}$ mouse chimeras myeloablated with Busulfan and transplanted with Hbb$^{th3/+}$ bone marrow treated with ALS17 or ALS20.

Figure 11A:
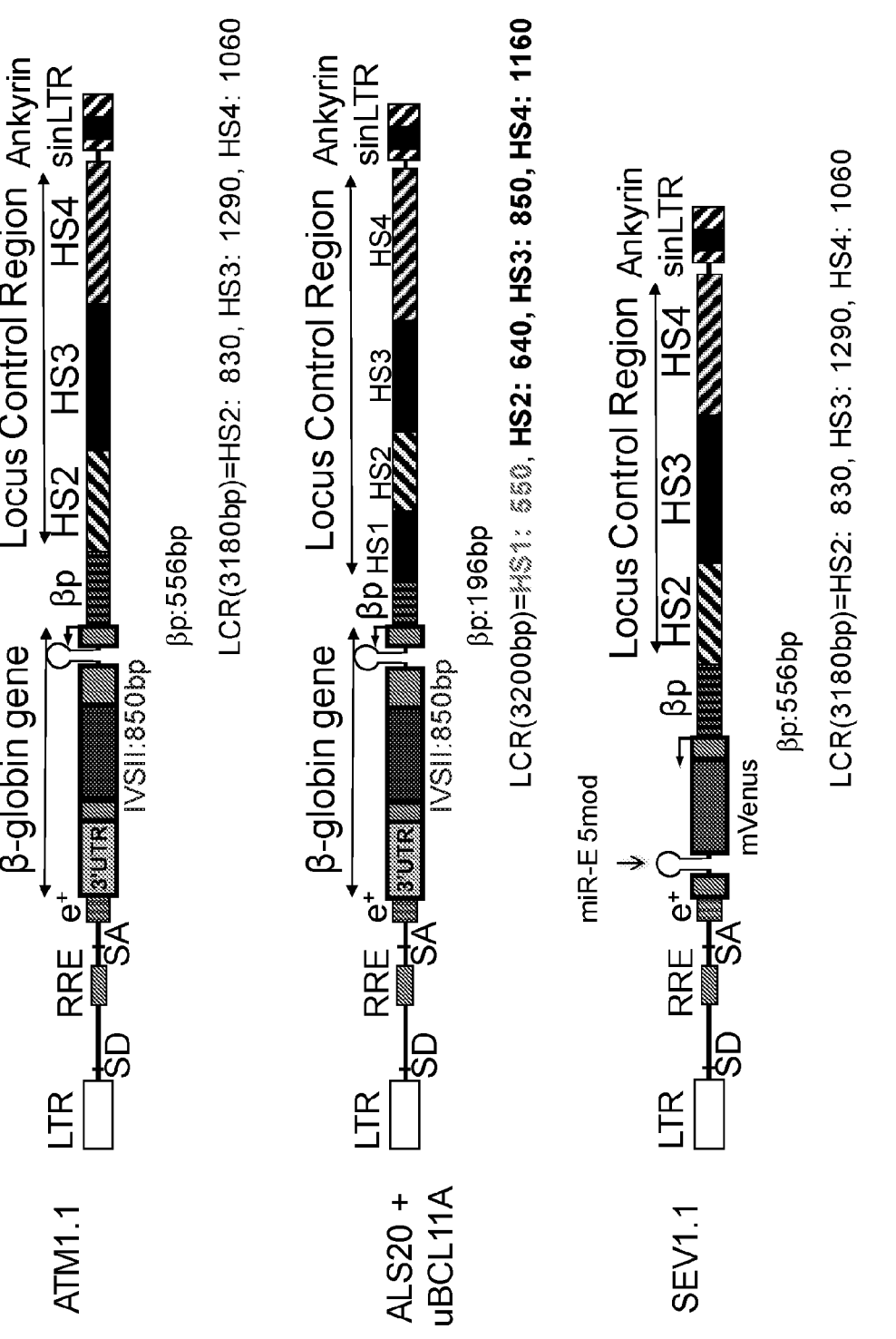
Figures 11B, 11C, 11D:
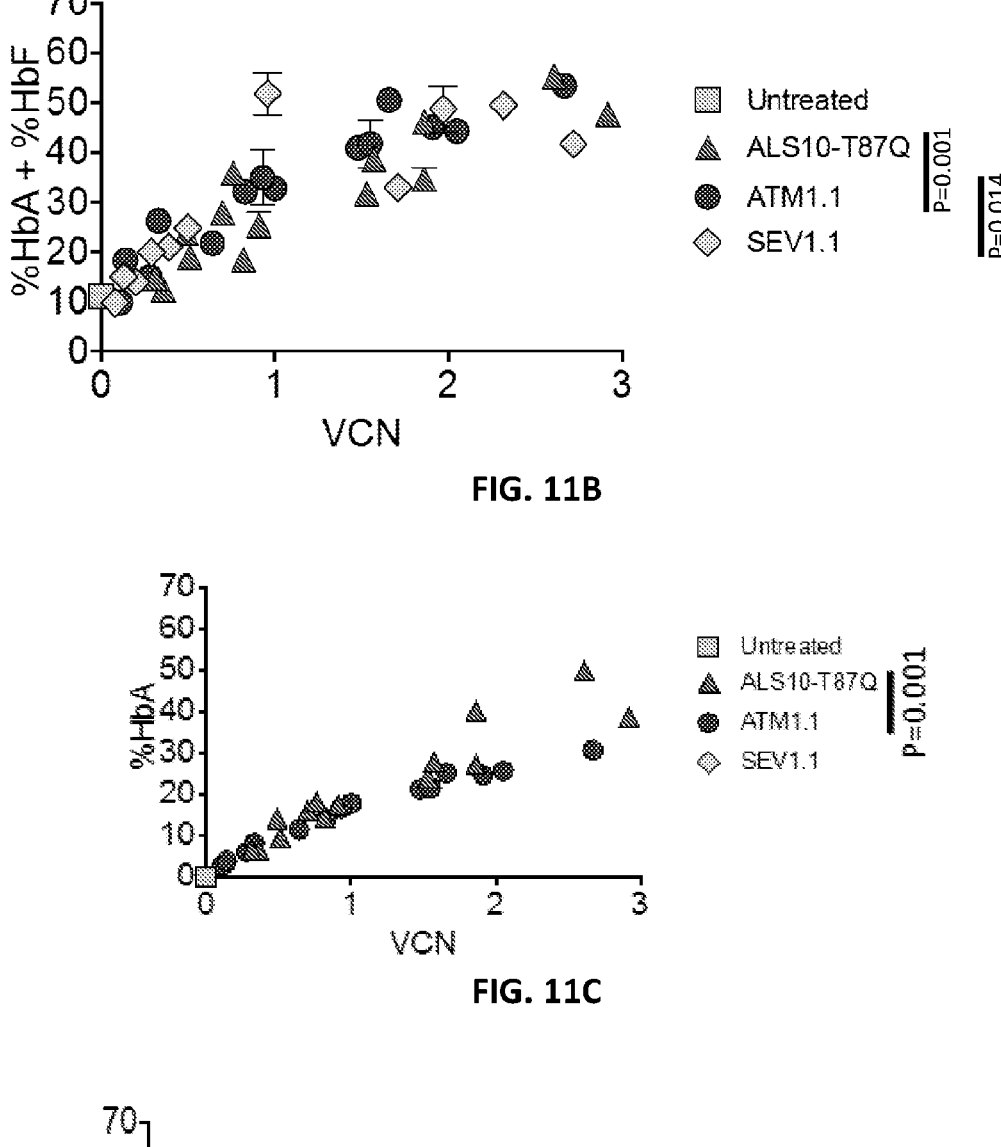

FIG. 11A provides schematics of ATM1.1, ALS20.1, and SEV1.1. FIGS. 11B, 11C, and 11D show HbA+HbF, HbA, and HbF, respectively, for ALS10-T87Q, ATM1.1 and SEV1.1.

Figure 12A:
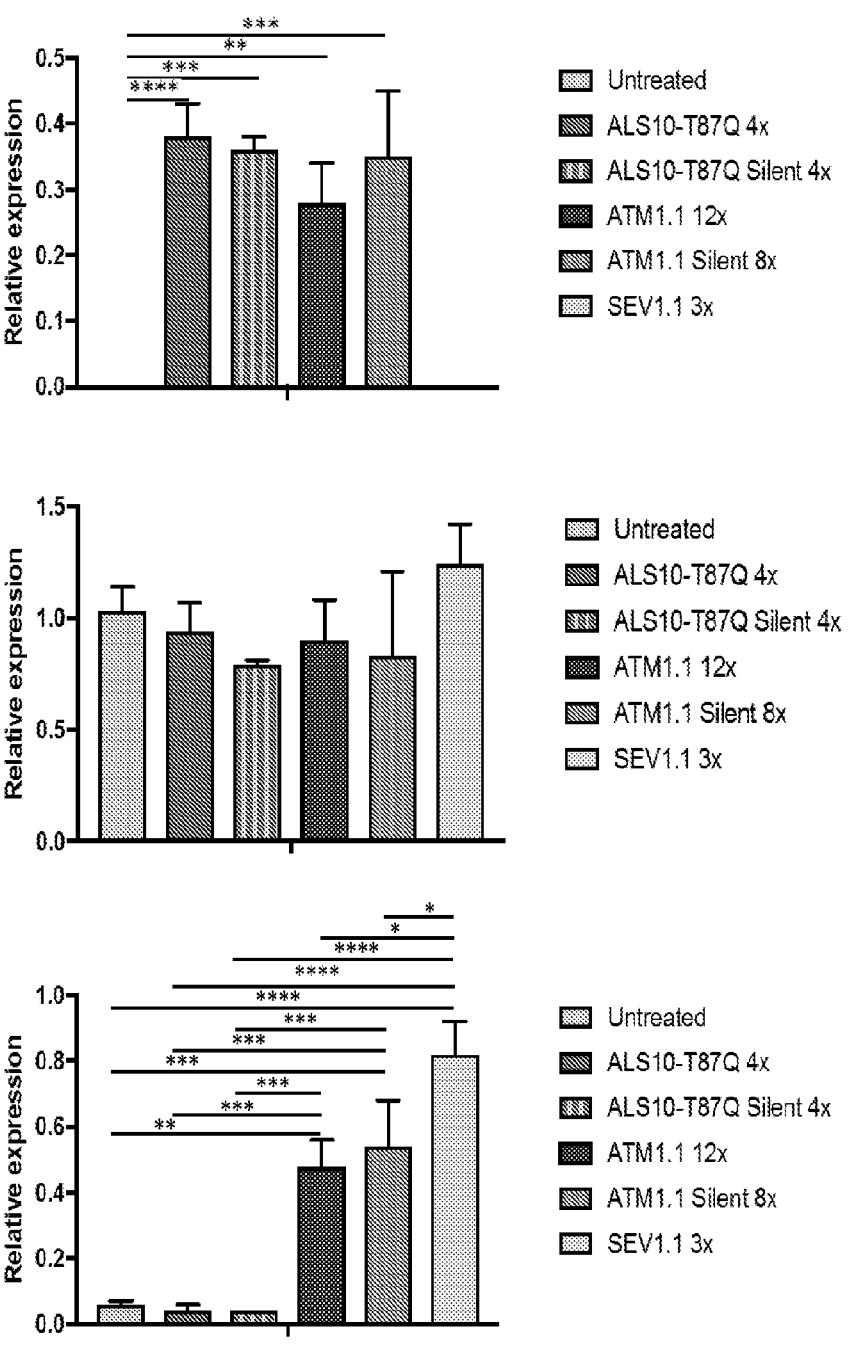
Figure 12B:
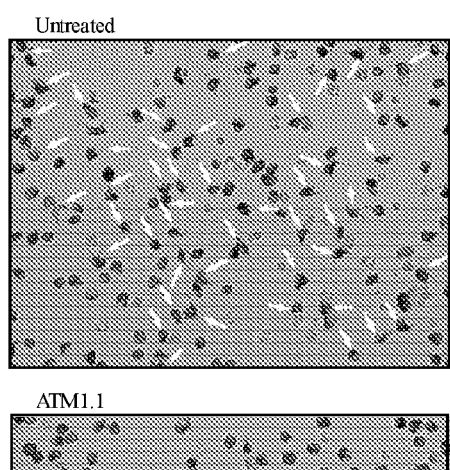
Figure 12B:
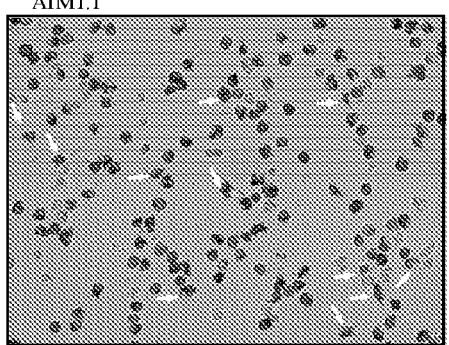
Figure 12C:
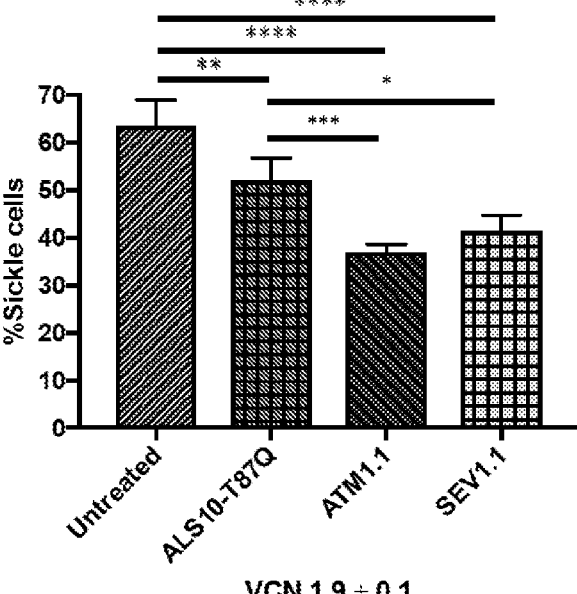

FIG. 12A provides graphs of the relative expression of beta-globin (WT or SCD) and gamma-globin with the indicated vectors. FIG. 12B shows images of untreated cells or cells transduced with ATM1.1. FIG. 12C shows the percentage of sickle-like morphology for cells transduced with the indicated vectors.

Figure 13A:
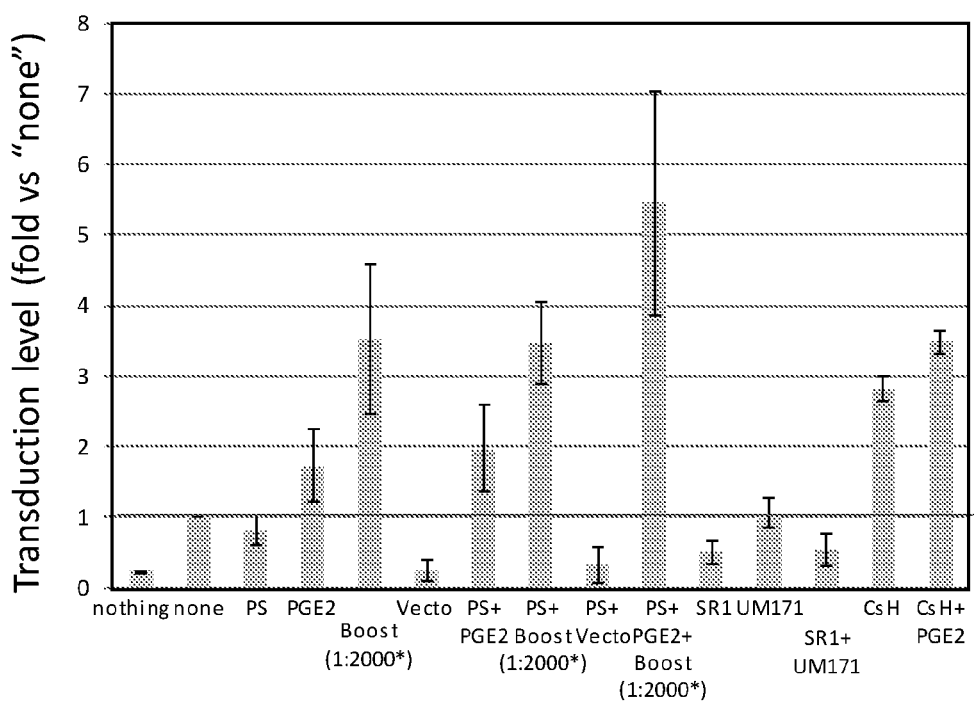
Figure 13B:
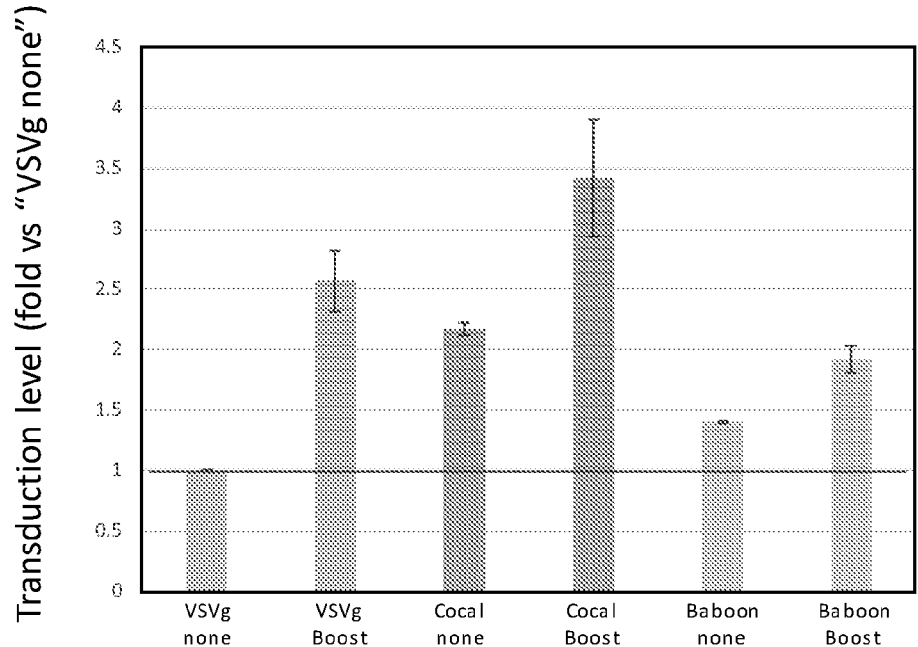
Figure 13C:
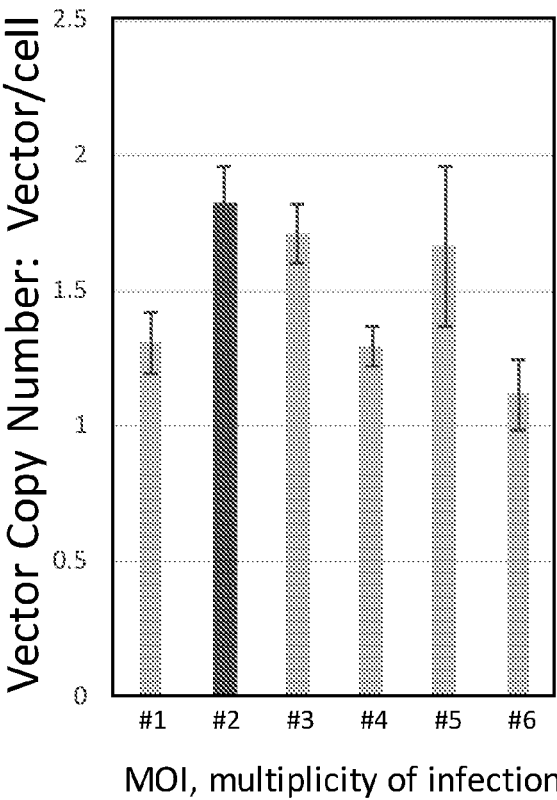

FIG. 13A provides the transduction level with the indicated adjuvants. FIG. 13B provides the transduction level with the indicated envelope proteins. FIG. 13C provides VCN/cell under the indicated conditions.

DETAILED DESCRIPTION OF THE INVENTION

Beta-thalassemia is an inherited blood disorder characterized by mutations in the beta-globin gene, one of the two proteins responsible for making adult hemoglobin, the oxygen carrier molecule. The second molecule is the alpha-globin protein. As a consequence, in progenitor cells responsible for making red blood cells, there is an excess of alpha globin proteins or chains. This excess of alpha globin chains complexes with heme molecules and forms toxic complexes that leads to limited synthesis or production of abnormal red cells and anemia. In nature, there are individuals with more or less alpha globin genes (normally there are 2 alpha-globin genes on each chromosome 16). Individuals with mutations in the beta-globin gene who inherit more or less alpha globin genes show, respectively, a worsening or amelioration of the beta-thalassemia phenotype. Therefore, there is a strong rationale to increase the synthesis of the beta globin gene in beta-thalassemia. In addition, other forms of hemoglobinopathies, such as sickle cell anemia or Hemoglobin E, are often inherited with a beta-globin gene mutation. For instance, some patients may carry one sickle cell mutation on one globin gene and one beta-globin mutation on the second beta-globin gene (compound heterozygotes). Therefore, these patients would benefit from increased synthesis of normal beta-globin chains.

U.S. Patent Application Publication 2018/0008725, incorporated by reference herein, provides viral vectors for the inhibition or treatment of hemoglobinopathies. In a particular embodiment, the viral vector comprises: i) a 5' long terminal repeat (LTR) and a self-inactivating 3' LTR (self-inactivating meaning the 3' LTR comprises a deletion relative to its native sequence, and thus results is replication incompetent); ii) at least one polyadenylation signal; iii) at least one promoter; iv) a globin gene locus control region (LCR); v) an ankyrin insulator element (Ank); vi) a Woodchuck Post-Regulatory Element (WPRE) configured such that the WPRE does not integrate into a target genome; and vii) a sequence that is a reverse complement to a sequence encoding beta-globin, particularly a modified human beta-globin comprising a βT87Q mutation (B-globinM). In a particular embodiment, the vector is ALS-10. ALS-10 is depicted schematically in FIG. 11 of U.S. Patent Application Publication 2018/0008725 and FIG. 14 of U.S. Patent Application Publication 2018/0008725 provides SEQ ID NO: 3 which is the polynucleotide sequence of the ALS-10 vector (incorporated by reference herein).

The present disclosure provides compositions and methods for the inhibition, prevention, and/or treatment of hemoglobinopathies. In particular, the present disclosure provides novel viral vectors for the inhibition, prevention, and/or treatment of hemoglobinopathies. Viral vectors include, for example, retroviruses and lentiviruses. In a particular embodiment, the viral vector is a lentivral vector. The viral vector may comprise one or more (or all) of the modifications listed below. In a particular embodiment, one of ALS10, ALS16, ALS17, ALS18, ALS19, and ALS20 comprises one or more (or all) of the modifications listed below.

First, in certain embodiments of the instant invention, a vector is modified to increase expression and safety. First, to more closely mimic the endogenous beta-globin sequence and preserve its regulation by endogenous elements, the instant vector contains a complete intron 2. Previous vectors have used a truncated version of intron 2 (−374 bp) since this element was shown to decrease titer in other oncoretroviral vectors. However, with the instant vectors, no negative effect was observed on complete intron-2 containing vector titers. Second, the Woodchuck Post-Regulatory Element, or WPRE was eliminated from the integrating sequence to increase the safety of the vector. The WPRE was originally part of the integrated portion of the vector since it was placed between the LCR and the 3' LTR. The WPRE increases the titer of the lentivirus, but it can undergoes chromosomal rearrangement upon integration. In order to preserve the ability of WPRE to increase viral titers without having this viral element in the integrating sequence, the WPRE was removed from the integrating portion and added after the 3'LTR. In addition, a strong bovine growth hormone polyA tail was inserted after the WPRE region to increase lentiviral titers (Zaiss, et al. (2002) J. Virol., 76(14):7209-19). Third, the vector comprises the ankyrin element. The ankyrin element increases the expression of the beta-globin gene (Breda, et al. (2012) PloS One, 7(3):e32345). However, the combination of the full second intron and the ankyrin element yields a vector that is superior to a vector comprising the ankyrin and a much smaller version of the second intron.

Second, in certain embodiments of the instant invention, the vector may comprise insulators to maximize beta-globin expression at a random site of integration and to protect the host genome from possible genotoxicity. Insulators can shelter the transgenic cassette from the silencing effect of non-permissive chromatin sites and, at the same time, protect the genomic environment from the enhancer effect mediated by active regulatory elements (like the LCR) introduced with the vector. The 1.2 Kb cHS4 insulator has been used to rescue the phenotype of thalassemic CD34+ BM-derived cells (Puthenveetil, et al. (2004) Blood, 104 (12):3445-53). Further, fetal hemoglobin can be synthesized in human CD34*-derived cells after treatment with a lenti-viral vector encoding the gamma-globin gene, either in association with the 400 bp core of the cHS4 insulator or with a lentiviral vector carrying an shRNA targeting the gamma-globin gene repressor protein BCL 11A (Wilber, et al. (2011) Blood, 117(10):2817-26). The HS2 enhancer of the GATA1 gene has also been used to achieve high beta-globin gene expression in human cells from patients with beta-thalassemia (Miccio, et al. (2011) PLoS One, 6(12): e27955). The use of a 200 bp insulator, derived from the promoter of the ankyrin gene, resulted in a significant amelioration of the thalassemic phenotype in mice and high level of expression was reached in both human thalassemic and SCD cells (Breda, et al. (2012) PloS one 7(3):e32345).

Third, in certain embodiments of the instant invention, the ankyrin element and the regulatory enhancer of ALS10 were modified. First, the original ankyrin element in the 3'LTR of the ALS10 vector of U.S. Patent Application Publication 2018/0008725 was cloned from a bacterial plasmid and contained additional plasmid DNA. Herein, the vector has been modified to remove the bacterial plasmid DNA, thereby reducing the size of the 3' LTR from 528 basepairs to 411 basepairs. Second, the regulatory enhancer that allows expression of the beta-globin gene in ALS10 was generated using DNA fragments from the human locus control region—HS2, HS3, and HS4. However, the HS4 in ALS10 was truncated and did not contain a complete core element. Herein, the vector has been modified to comprise an HS4 with a complete core element. The vector comprising these modifications is referred to herein as ALS16. Further variants of the LCR are provided in FIG. 3A and are referred to as ALS17, ALS18, ALS19, and ALS20.

Fourth, in certain embodiments of the instant invention, the vector comprises the Rev response element (RRE) from HIV located near the 3'LTR. The Rev response element (RRE) of HIV facilitates nucleo-cytoplasmic export of viral mRNAs (Sherpa et al. (2015) Nucleic Acids Res., 43(9): 4676-86; incorporated by reference herein). In a particular embodiment, the RRE is located between the LCR and the 3'LTR or between the LCR and Ankyrin-sinLTR.

Fifth, in certain embodiments of the instant invention, the vectors of the instant invention may also comprise silent mutations within the coding region of the beta-globin gene (e.g., in exon 1 and/or 2). The presence of silent mutations allows for the discrimination of exogenous and endogenous mRNA while maintaining the coding sequence. For example, the following sequence in exon 1:

```
                                        (SEQ ID NO: 3)
CTGCCCAGGGCCTCaCCaCCaACTTCATCCACGTTCACCTTGCCCCACA

GGGCAGTAACGGCAGACTTCTCCTCAGGAGTCAGaTGCACCAT
``` can be changed to

```
                                        (SEQ ID NO: 4)
CTGCCCAGGGCCTCgCCgCCgACTTCATCCACGTTCACCTTGCCCCACA

GGGCAGTAACGGCAGACTTCTCCTCAGGAGTCAGaTGCACCAT
```

As another example, the following sequence in exon 2:

```
                                        (SEQ ID NO: 5)
ACTCAGTGTGGCAAAGGTGCCCTTGAGGTTGTCCAGGTGAGCCAGGCCA

TCactaAAGGCACCGAGCACTTTCTTGCCATGAGCCTTCACCTTAGGGT

TG
``` can be changed to

```
                                        (SEQ ID NO: 6)
ACTCAGTGTGGCAAAGGTGCCCTTGAGGTTGTCCAGGTGAGCCAGGCCA

TCggagAAGGCACCGAGCACTTTCTTGCCATGAGCCTTCACCTTAGGGT

TG
```

Sixth, in certain embodiments of the instant invention, the vectors comprise inhibitory nucleic acid molecules targeting BCL11A (e.g., shRNA, siRNA, antisense, etc). In a particular embodiment, the vector comprises shRNAmiR targeting BCL11A. In a particular embodiment, the shRNAmiR sequence is cloned in the non-coding regions of the beta-globin gene of ALS10, such as in introns 1 and 2, and the 3'UTR. In a particular embodiment, the shRNAmiR sequence targeting BCL11A is provided in Guda S. et. al. (Mol. Ther. (2015) 23:1465-1474), incorporated by reference herein. The shRNAmiR coding sequence may further be flanked by an optimized backbone termed "miR-E" (Fellmann et. al. (2013) Cell Reports 5:1704-1713; incorporated by reference herein). Thus, one single lentiviral vector will lead to 1) production of transgenic HbA, 2) reactivation of endogenous HbF, and 3) decreased production of endogenous mutant protein, maximizing the rate of Hb correction in patients with β-globinopathies. The cumulative effect of HbA and HbF simultaneous production in the double-pronged approach will achieve curative levels of Hb in patients independently of their genotype. Moreover, by decreasing the production of endogenous mutant protein it allows for longer red blood cell lifespan and more effective erythropoiesis.

Seventh, in certain embodiments of the instant invention, the vector further comprises an inhibitory nucleic acid molecule (e.g., siRNA, shRNA, antisense, etc.) against alpha-globin. The normal human genome carries 4 copies of the alpha-globin gene and one copy of the beta-globin gene. The severity of β-thalassemia symptoms is associated with alpha and non α-globin chain ratio imbalance. It has been observed that α-globin gene triplication/quadruplication in the alpha-globin locus can aggravate the clinical phenotype of a defective β-globin gene. On the other hand, deletion of α-globin genes in combination with beta-thalassemia ame- liorates the clinical condition. Thus, patients affected by beta-thalassemia show a better phenotype if the mutation in the beta-globin gene is associated with deletion of a certain number of alpha-globin genes (but no complete absence of alpha-globin expression). For this reason, ALS vectors can be modified to include an inhibitory nucleic acid molecule (e.g., a shRNA) that will decrease the expression of the alpha-globin gene and facilitate normalization of the alpha/ non α-globin chain ratio imbalance (i.e. normalization of the alpha-globin/beta-globin chains balance). This would be particularly important in those patients with no or very low expression of the beta-globin gene (beta0/beta0 genotypes).

In certain embodiment, the viral vector has a nucleotide sequence identical to those presented herein or they can have least 80, 81, 82, 83, 84, 85, 86, 87, 88, 89, 90, 91, 92, 93, 94, 95, 96, 97, 98, or 99% identity to the nucleotide sequence of a viral vector disclosed herein or to an element of a nucleo- tide sequence of a viral vector disclosed herein (e.g., all or part of SEQ ID NO: 1). The beta-globin gene of the viral vectors of the instant invention may be wild-type or a therapeutic variant of the beta-globin gene. For example, the βT87Q form of beta-globin has been used to improve hematological parameters of the SAD and BERK mouse models of SCA (Pawliuk, et al. (2001) Science 294:2368-2371) and was also used in the first successful clinical trial to correct a patient with β0/βE thalassemia (Cavazzana-Calvo, et al. (2010) Nature 467:318-322).

In accordance with another aspect of the instant invention, methods of transducing cells with a viral vector (e.g., ALS20) of the instant are provided. In a particular embodi- ment, the transduction is performed with the adjuvant/ enhancer LentiBoost™ or cyclosporine H. In a particular embodiment, the viral vector is pseudotyped with Cocal envelope. In a particular embodiment, the transduction is performed by prestimulating for 24 hours and using a 2-hit transduction (e.g., a MOI 10/10 at 16 and 8 hours).

In accordance with the instant invention, compositions and methods are provided for increasing hemoglobin pro- duction in a cell or subject. In a particular embodiment, the method increases adult hemoglobin and/or fetal globin expression. The method comprises administering a viral vector of the instant invention to the cell, particularly an erythroid precursor cell or erythroid cell (e.g., CD34+ cell), or subject. In a particular embodiment, the subject has a hemoglobinopathy such as sickle cell disease or thalassemia. In a particular embodiment, the subject has sickle cell anemia. The viral vector may be administered in a compo- sition further comprising at least one pharmaceutically acceptable carrier.

In accordance with another aspect of the instant invention, compositions and methods for inhibiting (e.g., reducing or slowing), treating, and/or preventing a hemoglobinopathy or thalassemia in a subject are provided. In a particular embodi- ment, the hemoglobinopathy is β-thalassemia or sickle cell anemia. In a particular embodiment, the subject has sickle cell anemia. In a particular embodiment, the methods com- prise administering to a subject in need thereof a viral vector of the instant invention. The viral vector may be adminis- tered in a composition further comprising at least one pharmaceutically acceptable carrier. The viral vector may be administered via an ex vivo methods wherein the viral vector is delivered to an erythroid precursor cell or erythroid cell (e.g., CD34+ cell), particularly autologous ones, and then the cells are administered to the subject. In a particular embodiment, the method comprises isolating hematopoietic cells (e.g., erythroid precursor cells) or erythroid cells from a subject, delivering a viral vector of the instant invention to the cells, and administering the treated cells to the subject. The methods of the instant invention may further comprise monitoring the disease or disorder in the subject after administration of the composition(s) of the instant invention to monitor the efficacy of the method. For example, the subject may be monitored for characteristics of low hemo- globin or a hemoglobinopathy.

As explained hereinabove, the compositions of the instant invention are useful for increasing hemoglobin production and for treating hemoglobinopathies and thalassemias. A therapeutically effective amount of the composition may be administered to a subject in need thereof. The dosages, methods, and times of administration are readily determin- able by persons skilled in the art, given the teachings provided herein.

The components as described herein will generally be administered to a patient as a pharmaceutical preparation. The term "patient" or "subject" as used herein refers to human or animal subjects. The components of the instant invention may be employed therapeutically, under the guid- ance of a physician for the treatment of the indicated disease or disorder.

The pharmaceutical preparation comprising the compo- nents of the invention may be conveniently formulated for administration with an acceptable medium (e.g., pharma- ceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conven- tional media or agent is incompatible with the agents to be administered, its use in the pharmaceutical preparation is contemplated.

The compositions of the present invention can be admin- istered by any suitable route, for example, by injection (e.g., for local (direct) or systemic administration), oral, pulmo- nary, topical, nasal or other modes of administration. The composition may be administered by any suitable means, including parenteral, intramuscular, intravenous, intraarte- rial, intraperitoneal, subcutaneous, topical, inhalatory, trans- dermal, intrapulmonary, intraareterial, intrarectal, intramus- cular, and intranasal administration. In a particular embodiment, the composition is administered directly to the blood stream (e.g., intravenously). In general, the pharma- ceutically acceptable carrier of the composition is selected from the group of diluents, preservatives, solubilizers, emul- sifiers, adjuvants and/or carriers. The compositions can include diluents of various buffer content (e.g., Tris HCl, acetate, phosphate), pH and ionic strength; and additives such as detergents and solubilizing agents (e.g., polysorbate 80), anti oxidants (e.g., ascorbic acid, sodium metabisulfite), preservatives (e.g., Thimersol, benzyl alcohol) and bulking substances (e.g., lactose, mannitol). The compositions can also be incorporated into particulate preparations of poly- meric compounds such as polyesters, polyamino acids, hydrogels, polylactide/glycolide copolymers, ethyleneviny- lacetate copolymers, polylactic acid, polyglycolic acid, etc., or into liposomes. Such compositions may influence the physical state, stability, rate of in vivo release, and rate of in vivo clearance of components of a pharmaceutical composition of the present invention. See, e.g., Remington: The Science and Practice of Pharmacy, 21st edition, Philadelphia, PA. Lippincott Williams & Wilkins. The pharmaceutical composition of the present invention can be prepared, for example, in liquid form, or can be in dried powder form (e.g., lyophilized for later reconstitution).

As used herein, "pharmaceutically acceptable carrier" includes any and all solvents, dispersion media and the like which may be appropriate for the desired route of administration of the pharmaceutical preparation, as exemplified in the preceding paragraph. The use of such media for pharmaceutically active substances is known in the art. Except insofar as any conventional media or agent is incompatible with the molecules to be administered, its use in the pharmaceutical preparation is contemplated.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous. Injectable suspensions may be prepared, in which case appropriate liquid carriers, suspending agents and the like may be employed. Pharmaceutical preparations for injection are known in the art. If injection is selected as a method for administering the therapy, steps should be taken to ensure that sufficient amounts of the molecules reach their target cells to exert a biological effect.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art. The appropriate dosage unit for the administration of the molecules of the instant invention may be determined by evaluating the toxicity of the molecules in animal models. Various concentrations of pharmaceutical preparations may be administered to mice with transplanted human tumors, and the minimal and maximal dosages may be determined based on the results of significant reduction of tumor size and side effects as a result of the treatment. Appropriate dosage unit may also be determined by assessing the efficacy of the treatment in combination with other standard therapies.

The pharmaceutical preparation comprising the molecules of the instant invention may be administered at appropriate intervals, for example, at least twice a day or more until the pathological symptoms are reduced or alleviated, after which the dosage may be reduced to a maintenance level. The appropriate interval in a particular case would normally depend on the condition of the patient.

Definitions

The singular forms "a," "an," and "the" include plural referents unless the context clearly dictates otherwise.

The terms "isolated" is not meant to exclude artificial or synthetic mixtures with other compounds or materials, or the presence of impurities that do not interfere with the fundamental activity, and that may be present, for example, due to incomplete purification, or the addition of stabilizers. "Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., polysorbate 80), emulsifier, buffer (e.g., Tris HCl, acetate, phosphate), antimicrobial, bulking substance (e.g., lactose, mannitol), excipient, auxilliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient suffering from a disease or disorder, including improvement in the condition of the patient (e.g., in one or more symptoms), delay in the progression of the condition, etc.

As used herein, the term "prevent" refers to the prophylactic treatment of a subject who is at risk of developing a condition and/or sustaining a disease or disorder, resulting in a decrease in the probability that the subject will develop conditions associated with the hemoglobinopathy or thalassemia.

A "therapeutically effective amount" of a compound or a pharmaceutical composition refers to an amount effective to prevent, inhibit, or treat a particular injury and/or the symptoms thereof. For example, "therapeutically effective amount" may refer to an amount sufficient to modulate the pathology associated with a hemoglobinopathy or thalassemia.

As used herein, the term "subject" refers to an animal, particularly a mammal, particularly a human.

A "vector" is a genetic element, such as a plasmid, cosmid, bacmid, phage or virus, to which another genetic sequence or element (either DNA or RNA) may be attached so as to bring about the replication and/or expression of the attached sequence or element. A vector may be either RNA or DNA and may be single or double stranded. A vector may comprise expression operons or elements such as, without limitation, transcriptional and translational control sequences, such as promoters, enhancers, translational start signals, polyadenylation signals, terminators, and the like, and which facilitate the expression of a polynucleotide or a polypeptide coding sequence in a host cell or organism.

The following examples are provided to illustrate various embodiments of the present invention. They are not intended to limit the invention in any way.

Example 1

FIG. 1A provides a schematic of a ALS10 vector. First, the vector comprises a beta-globin sequence with a complete intron 2. Second, the Woodchuck Post-Regulatory Element (WPRE) was added after the 3'LTR with a strong bovine growth hormone polyA tail after the WPRE region and an ankyrin element after the 3'LTR. As seen in FIG. 1B, the combination of the full second intron and ankyrin element is superior to the vector in which the ankyrin is present with a much smaller version of the second intron (AnkT9 (Breda, et al. (2012) PLoS One, 7(3):e32345)). Briefly, CD34+ cells isolated from thalassemic patients that do not make any adult hemoglobin (indicated as $\beta^{o/o}$) were infected with AnkT9 or ALS10 after differentiation to erythrocytes. The total hemoglobin was analyzed by HPLC. FIG. 1B shows that ASL10 reaches significant higher levels of curative hemoglobin in po/o cells compared to AnkT9.

Example 2

The ankyrin element and the regulatory enhancer of ALS10 were also modified. First, the original ankyrin element in the 3'LTR of the ALS10 vector of U.S. Patent Application Publication 2018/0008725 was cloned from a bacterial plasmid and contained additional plasmid DNA. Herein, the vector has been modified to remove the bacterial plasmid DNA, thereby reducing the size of the 3' LTR from 528 basepairs to 411 basepairs. Second, the regulatory enhancer that allows expression of the beta-globin gene in ALS10 was generated using DNA fragments from the human locus control region—HS2, HS3, and HS4. However, the HS4 in ALS10 was truncated and did not contain a complete core element. Herein, the vector has been modified to comprise an HS4 with a complete core element. The vector comprising these modifications is referred to herein as ALS16.

FIG. 2A provides a schematic of the ALS10 and ALS16 vectors along with two clinical vectors (CV-1 and CV-2). FIG. 2B demonstrates that increasing the vector copy number increases the expression of HbA in two different clones of an erythroid progenitor cell line. The clones were transduced with ALS10, ALS16, CV-II (a vector encoding T87Q beta-globin; Globe vector, TIGET), or CV-I (a vector encoding T87Q beta-globin; LentiGlobin BB305). ALS16 yielded the greatest synthesis of HbA.

FIG. 3A provides schematics of ALS10, ALS16, ALS17, ALS18, ALS19, and ALS20. The HS1 core element was added to ALS17, ALS19, and ALS20. ALS18 and ALS19 contained shorter LCR regions. FIG. 3B provides a schematic of a further modification. The Rev response element (RRE) of HIV facilitates nucleo-cytoplasmic export of viral mRNAs (Sherpa et al. (2015) Nucleic Acids Res., 43(9): 4676-86). The RRE element of HIV was moved from between the 5'LTR and the end of the beta-globin gene to increase viral titer. The RRE will increase vector production when presented closer to the 3'LTR (e.g., between the LCR and the 3'LTR).

FIG. 4A provides a schematic map of ALS17 and FIG. 4B provides an annotated nucleic acid sequence of ALS17.

FIG. 5 shows the dose/response analyses obtained plotting integration levels (VCN) against HbA % values in cells treated with CV-I, CV-II versus ALS16-17-18-19 within a range of VCN between 0.25 and 3 in an erythroid progenitor cell line (top left) or in primary erythroblasts isolated from patients and differentiated in vitro (top right). FIG. 5 also shows comparative levels of HbA at average VCN=1.77 representing the % of curative-HbA over the of number of viral integrations per cell after transduction with ALS-16, -17, -18, -19, CV-I, and CV-II (bottom, left). FIG. 5 also shows comparative levels of HbA at average VCN=0.5 or 1.1 in SCD specimens treated with CV-I, ALS17 and ALS19 (N=3; one way Anova with Dunnet's multiple comparison test). As seen in FIG. 5, ALS17 yields a significantly higher production of HbA than any of the other vectors.

Example 3

Gene addition of a functional copy of $\beta$-globin and reactivation of fetal hemoglobin (HbF) are promising therapeutic approaches for $\beta$-globinopathies such as Sickle Cell Disease (SCD) and $\beta$-thalassemia ($\beta$-thal).

Hydroxyurea (HU) is an approved pharmacological therapy for patients with SCD based on the reactivation of HbF. However, since only a low percentage of patients respond positively to HU, additional therapies are needed. An alternative approach is the use of shRNAs targeting BCL11A, a known transcription factor involved in the repression of $\gamma$-globin. shRNA miR have been shown not only to knockdown BCL11A but also to increase the levels of HbF (Guda et al. (2015) Mol. Ther. 23(9):1465-74).

Moreover, results from the ongoing clinical trials for $\beta$-hemoglobinopathies, based on lentiviral delivery of the $\beta$-globin gene, indicate that a successful outcome is genotype-dependent. So far, the vectors used in the trials have failed to produce curative Hb levels in most of the patients whose genotype leads to null adult hemoglobin (HbA) synthesis, like the $\beta 0/\beta 0$. Therefore, to achieve HbA synthesis at therapeutic levels in the most severe of genotypes, and with minimal vector copy number (VCN) per cell, more powerful and versatile vectors are required.

New lentiviral vectors provided herein are indicated as ALS (ALS10, ALS16, ALS17, ALS18, ALS19, and ALS20). In particular, ALS10 carries the $\beta$-globin gene, including the non-coding regions. In erythroblasts from patients with SCD and 3-thal ALS10 induces HbA synthesis of 26.8% and 68.6%, respectively, with an average VCN=1.

Here, shRNAmiR targeting the transcription factor BCL11A, a known repressor of beta-globin, was incorporated into ALS10. Guda et. al. (Mol. Ther. (2015) 23:9:1465-1474) provide sequences which were flanked by a miRNA scaffold to mimic the structure of endogenous miRNAs and termed shRNAmiR (see FIG. 4A of Guda et al.; incorporated by reference herein). The shRNAmiR sequences targeting BCL11A (Guda et. al. (2015) Mol. Ther., 23:9:1465-1474) were flanked by an optimized backbone for miR-30 termed "miR-E" (Fellmann et. al. (2013) Cell Reports 5:1704-1713; see FIG. 1 and S1; incorporated by reference herein) to increase mature shRNA levels and knockdown efficiency. The presence of the shRNAmiR knock down BCL11A and increase HbF levels. This approach will overcome limitations of the vectors presently on clinical trials by simultaneous 1) production of transgenic HbA, 2) reactivation of endogenous HbF, and 3) decreased production of endogenous mutant protein.

First, an erythroid precursor cell line which produces a hemoglobin variant (Hb-mutant) was established. As Hb-mutant is distinguishable from HbA and HbF by high-performance liquid chromatography (HPLC), one can easily compare the production of HbA+HbF to Hb-mutant and correlate these values to VCN. Upon transduction in the cell line, ALS10 induced 18%, 23% and 44% of HbA for VCN=0.6, VCN=1 and VCN 2.0, respectively.

The miR-E-BCL11A sequence (the BCL11A sequence was #5 from FIG. 4A of Guda et al.) was cloned either in the $\beta$-globin intron 1 (ATM1; position c.79+36 (count starts at the first nucleotide of intron 1)) or in two different regions of the intron 2 (ATM2.1 (c.303-163 (reverse count starts at last nucleotide of intron 2)) and ATM2.2 (c.303-172)). Upon transduction of the above cell line, ALS10 expressed higher levels of HbA when compared to the ATM vectors (ALS10-T87Q/miR-E-BCL11A5 vectors) (FIG. 6). ATM1, the best of the ATM vectors, showed production of HbA by HPLC equivalent to ~70% of the total HbA produced by ALS10 (for VCN=1) (FIG. 6). Western blot analyses confirmed a reduction of BCL11A protein levels and concurrent increase of gamma-globin levels upon integration of the dual vectors (FIG. 7). This data indicated that inclusion of the miRNA was not optimal, and interfered with production of HbA.

To overcome this limitation, the miRE-BCL11A was further modified in intron 1, generating the vector ATM1S. The sequence of the modified sequence—within intron 1—is seen in FIG. 8C. This time, production of therapeutic Hb (HbA+HbF) generated by ATM1S was ~20% superior compared to the total HbA produced by ALS10 (FIG. 8A). Additionally, the HbF and HbA levels increased proportionately to vector copy number per cell (FIG. 8B). Western blot analyses confirmed a reduction of BCL11A and increase of 7-globin protein levels. In conclusion, the results show that both HbA and HbF can be elevated using a single lentiviral construct where the total production of HbF and HbA surpasses the production of HbA by a single ε-globin expressing vector.

The miR-E-BCL11A was also added within intron 1 of the beta-globin gene of ALS19 (FIG. 9A). Moreover, ALS10-T87Q was also modified to express the miR-E-BCL11A with mVenus as a marker protein (SEV1-uBCL11A) (FIG. 9A). The combined vectors ATM1S and ALS19+uBCL11A outperformed ALS10-T87Q in transduced SCD primary cells, with ATM1S and ALS19+uBCL11A showing, respectively, ~10% and ~25% net increase of therapeutic Hb (HbA+HbF) when compared the total amount of HbA produced by ALS10-T87Q (FIG. 9B). HbF and HbA levels increase proportionally to vector copy number (VCN) per cell (FIG. 9C).

Example 4

Hemoglobin A synthesis in human umbilical cord blood-derived erythroid progenitor (HUDEP) clone M #13 and in erythroid cells from patients with SCD was measured after transduction with beta-LVs. In Hudep #M13, linear regression analysis of the ratio of HbA to vector copy number (VCN) for each treatment, indicates that ALS17 and ALS20 yield roughly 40, 157 and 84% more HbA per copy than CV-1, CV-2 and CV-3, respectively (FIG. 10A). FIG. 10A provides a dose/response analyses obtained plotting integration levels (VCN) against HbA % values in cells treated with CV-I, CV-II, CV-III versus ALS16-17-18-19-20 within a range of VCN between 0.25 and 3 in M #13 cells. On right, linear regression analyses for comparison of HbA increase at integration=1 VCN in HUDEPs. FIG. 10B provides a dose/response analyses obtained plotting integration levels (VCN) against HbA % values in cells treated with CV-I versus ALS17-19-20. On right, linear regression analyses for comparison of HbA increase at integration=1 VCN in SCD primary cells. Linear regression analysis of the ratio of HbA to vector copy number (VCN) for each treatment, indicates that ALS20 yield ~40% more HbA per copy than CV-1 (BB305). FIG. 10C shows the hemoglobin A synthesis in erythroid cells from patients with β0/0 thalassemia, after transduction with beta-LVs ALS20. Dose/response analyses obtained plotting integration levels (VCN) against HbA % values in primary erythroblasts isolated from 3 different patients with β0/0 genotype and differentiated in vitro.

Hbb$^{th3/+}$ chimeras were generated using transplantation of BM (w/ or w/o ALS17 or ALS20) into Hbb$^{th3/+}$ mice conditioned with Busulfan. Briefly, recipient thalassemic Hbb$^{th3/+}$ mice are injected at 24 hour intervals for 4 consecutive days (17.5 mg/Kg dose/day) and injected 24 after the last injection with lineage negative (immuno-selected) hematopoietic stem cells, treated or not with a lentiviral vector that carries the human beta globin gene. All the animals treated with ALS17 or ALS20 show high levels of hemoglobin, superior to baseline levels of thalassemic mice non-treated with any vector (Hbb$^{th3/+}$, showing hemoglobin levels in the range of 7 g/dl). Of note, hemoglobin levels 9 g/dl or higher are considered curative. In particular, it was observed that mice that show VCN of 0.8 or higher associated with level of chimerism equal or superior to 50% (donor engrafted cells/(donor+endogenous cell)) showed the highest hemoglobin levels (FIG. 10D). These levels are similar to those observed in WT animals (in the range of 12-14 g/dL). In summary, high levels of VCN and chimerism can completely normalize hemoglobin levels, but already low levels of the vector (VCN) and chimeras can be curative (the patient would be transfusion independent).

Example 5

FIG. 11A provides schematics of ATM1.1, ALS20.1, and SEV1.1. Consistent with the results obtained in M #9 cells, a dose-dependent induction of HbA+HbF was observed for ALS10-T87Q, ATM1.1 and SEV1.1 (FIGS. 11B-11D). Linear regression analyses predicted a % HbF+HbA induction of 27.7%, 31.6% and 29.7% for ALS10-T87Q, ATM1.1 and SEV1.1, respectively for VCN=1. The presence of miR-E-BCL11A does not affect the splicing nor lessen the production of the β-globin mRNA while increasing the levels of 7-globin mRNA and 7-globin expression. Cells treated with ALS10-T87Q and ATM1.1 showed identical results by RT-PCR and qPCR indicating that the presence of the miR-E-BCL11A in ATM1.1 does not affect the splicing nor lessen the production of the 0-globin mRNA (FIG. 12). When exposed to low oxygen tension, cells transduced with ATM1.1 were less prone to sickle than control cells (FIG. 12B). ATM1.1 treated cells showed the lowest percentage of sickle-like morphology (58.1%) when compared to cells transduced with ALS10-T87Q (81.9%) and SEV1.1 (65.1%) (FIG. 12C).

Example 6

Lentiviral vectors (LV) have been demonstrated as a safety gene transfer tool and a variety of clinical trials are ongoing to cure patients affected by hemoglobinopathies. However, these studies suggest that current vectors require high number of integrations (~4) in a pancellular fashion. This could increase the risk of genome toxicity, limiting the application of these vectors and preventing their use in a reduced myeloablative regimen. Here, a transduction protocol is provided.

Methods

LV constructs were prepared carrying the GFP reporter gene or the β-globin gene under the control of phosphoglycerate kinase (PGK) promoter (LV-GFP) or internal β-globin promoter (ALS17), respectively. Frozen human hematopoietic stem and progenitor cells (HSPC) derived from bone marrow (BM) were used as target cells to study the transduction efficiency. The cells were exposed to LVs at a multiplicity of infection (MOI) of 10 and 100, respectively. HSPC were transduced with eight different enhancers (polybrene (Manning et al. (1971) Appl. Microbiol. 22(6): 1162-1163), Prostaglandin E2 (PGE2) (Heffner et al., Mol Ther. (2018) 26(1):320-328), protamine sulfate (Cornetta, et al. (1989) J. Virol. Methods 23(2):187-94), LentiBoost™ (Deveille et al. (2018) Mol. Ther. Methods Clin. Dev., 10:341-347), Vectofusin-1 (Piovan, et al. (2017) Mol. Ther. Methods Clin. Dev., 5:22-30), StemRegenin1 (SR1) (Ngom et al. (2018) Mol. Ther. Methods Clin. Dev., 10:156-164), UM171 (Ngom et al. (2018) Mol. Ther. Methods Clin. Dev., 10:156-164), and Cyclosprine H (CsH) (Petrillo, et al. (2018) Cell Stem Cell 23, 820-832)). The exposed LV was psuedotyped with different envelopes (VSVg (Kuate et al. (2006) Virology 351(1):133-44), Cocal (Trobridge et al. (2010) Mol. Ther., 18(4):725-33) and Baboon (Bernadin et al. (2019) Blood Advances 3:461-475)). Transduction efficiency was calculated by GFP positivity using flow cytometry (7 days post-transduction) and vector copy number (VCN) using droplet digital polymerase chain reaction (ddPCR; 14 days post-transduction). For toxicology studies, an in vitro immortalization assay (IVIM), an analysis of the clonal dynamics in NSG-mice transplanted BM cells, and vector integration sites analysis were performed.

Results

LentiBoost™ promoted highest LV-GFP transduction, up to 3.5-fold compared to the transduction without enhancers (FIG. 13A). CsH also promoted high LV-GFP (FIG. 13A). The addition of PGE2 to LentiBoost or CsH enhanced transduction efficiency, but were toxic (FIG. 13A). Higher doses of LentiBoost™ further increased transduction, but were toxic to the cells. Cocal-pseudotyped LV-GFP transduced at highest efficiencies (1.3-fold) compared to VSVg-pseudotyped (FIG. 13B). Interestingly, Baboon-pseudotyped LV-GFP did not respond to LentiBoost™. Long-length VSVg-pseudotyped ALS17 vector (total-length; 14.1 kb) reached VCN up to 4.2 copies/cell. Of note, these levels were close to those achieved with a vector similar to BB305 (total-length; 11.9 kb), which is currently used in the clinical trials (NCT01745120 and NCT02151526).

Additionally, various transduction protocols for ALS20 mixed with LentiBoost™ were tested: #1: pre-stimulation (X-VIVO+SCF, TPO and Flt3L (50 ng/mL)) for 16 hours and 8 hours with 1-hit (MOI: 100); #2: pre-stimulation for 24 hours and 2-hit (MOI: 10/10) for 16 hours and 8 hours; #3: pre-stimulation for 24 hours and 24 hours with 1-hit (MOI: 100); #4: pre-stimulation for 24 hours and 2-hit (MOI: 10/10) for 24 hours and 24 hours; #5: pre-stimulation for 48 hours and 2-hit (MOI: 10/10) for 16 hours and 8 hours; #6: pre-stimulation for 48 hours and 24 hours with 1-hit (MOI: 100). The duration of pre-stimulation time did not show the significant difference of VCN. One-hit (MOI: 100) or 2-hit (MOI: 10) protocol did not show the significant difference of VCN. However, protocol #2 yielded the best transduction as seen in FIG. 13C.

The preliminary results confirm that this protocol allows efficient gene transfer of ALS17 into HSPC derived from bone marrow. This vector already showed promising results in achieving curative levels of β-globin production at 1-2 copies per cell (or even less) in HSPC derived from peripheral blood of patients affected by hemoglobinopathies. It is therefore fundamental to move forward with these studies to minimize the number of genomic integrations and reduce the chances of genome toxicity.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

---

What is claimed is:

1. A lentiviral vector comprising a nucleic acid molecule comprising:
   i) a 5' long terminal repeat (LTR) and a 3' LTR, wherein one of said LTRs is self-inactivating;
   ii) at least one polyadenylation signal;
   iii) at least one promoter;
   iv) a globin gene locus control region (LCR), wherein said LCR comprises HS1, HS2, HS3, and HS4, wherein said LCR comprises the nucleotide sequence of nucleotides 6766-10641 of SEQ ID NO: 1;
   v) an ankyrin insulator element (Ank);
   vi) a Woodchuck Post-Regulatory Element (WPRE), wherein the WPRE is 3' of the 3'LTR; and
   vii) a sequence encoding human beta-globin.

2. The lentiviral vector of claim 1, wherein said 3' LTR is 411 nucleotides in length.

3. The lentiviral vector of claim 1, further comprising a Rev response element (RRE).

4. The lentiviral vector of claim 3, wherein said RRE is located between the LCR and the 3'LTR.

5. The lentiviral vector of claim 1, wherein the lentiviral vector is present in CD34+ cells.

6. The lentiviral vector of claim 5, wherein the CD34+ cells have been isolated from an individual who has a hemoglobinopathy.

7. A composition comprising the lentiviral vector of claim 1 and a pharmaceutically acceptable carrier.

8. A composition comprising viral particles, wherein the viral particles comprise the lentiviral vector of claim 1.

9. A method for inducing expression of human beta-globin in erythrocytes comprising introducing into erythrocyte progenitor cells a lentiviral vector of claim 1.

10. A lentiviral vector comprising SEQ ID NO: 1.

* * * * *

SEQUENCE LISTING

```
<160> NUMBER OF SEQ ID NOS: 6

<210> SEQ ID NO 1
<211> LENGTH: 14135
<212> TYPE: DNA
<213> ORGANISM: Artificial Sequence
<220> FEATURE:
<223> OTHER INFORMATION: ALS17

<400> SEQUENCE: 1
ctgtcagacc aagtttactc atatatactt tagattgatt taaaacttca tttttaattt        60
aaaaggatct aggtgaagat ccttttttgat aatctcatga ccaaaatccc ttaacgtgag       120
ttttcgttcc actgagcgtc agaccccgta gaaaagatca aaggatcttc ttgagatcct       180 tttttctgc gcgtaatctg ctgcttgcaa acaaaaaaac caccgctacc agcggtggtt        240
tgtttgccgg atcaagagct accaactctt tttccgaagg taactggctt cagcagagcg       300
cagataccaa atactgtcct tctagtgtag ccgtagttag gccaccactt caagaactct       360
gtagcaccgc ctacatacct cgctctgcta atcctgttac cagtggctgc tgccagtggc       420
gataagtcgt gtcttaccgg gttggactca agacgatagt taccggataa ggcgcagcgg       480
tcgggctgaa cggggggttc gtgcacacag cccagcttgg agcgaacgac ctacaccgaa       540
ctgagatacc tacagcgtga gctatgagaa agcgccacgc ttcccgaagg gagaaaggcg       600
gacaggtatc cggtaagcgg cagggtcgga acaggagagc gcacgaggga gcttccaggg       660
```

-continued

```
ggaaacgcct ggtatcttta tagtcctgtc gggtttcgcc acctctgact tgagcgtcga      720
tttttgtgat gctcgtcagg ggggcggagc ctatggaaaa acgccagcaa cgcggccttt      780
ttacggttcc tggccttttg ctggcctttt gctcacatgt tctttcctgc gttatcccct      840
gattctgtgg ataaccgtat taccgccttt gagtgagctg ataccgctcg ccgcagccga      900
acgaccgagc gcagcgagtc agtgagcgag gaagcggaag agcgcccaat acgcaaaccg      960
cctctccccg cgcgttggcc gattcattaa tgcagctggc acgacaggtt tcccgactgg     1020
aaagcgggca gtgagcgcaa cgcaattaat gtgagttagc tcactcatta ggcaccccag     1080
gctttacact ttatgcttcc ggctcgtatg ttgtgtggaa ttgtgagcgg ataacaattt     1140
cacacaggaa acagctatga ccatgattac gccaagcgcg caattaaccc tcactaaagg     1200
gaacaaaagc tggagctgca agcttggcca ttgcatacgt tgtatccata tcataatatg     1260
tacatttata ttggctcatg tccaacatta ccgccatgtt gacattgatt attgactagt     1320
tattaatagt aatcaattac ggggtcatta gttcatagcc catatatgga gttccgcgtt     1380
acataactta cggtaaatgg cccgcctggc tgaccgccca cgacccccg cccattgacg     1440 tcaataatga cgtatgttcc catagtaacg ccaataggga ctttccattg acgtcaatgg     1500
gtggagtatt tacggtaaac tgcccacttg gcagtacatc aagtgtatca tatgccaagt     1560
acgcccccta ttgacgtcaa tgacggtaaa tggcccgcct ggcattatgc ccagtacatg     1620
acctatgggg actttcctac ttggcagtac atctacgtat tagtcatcgc tattaccatg     1680
gtgatgcggt tttggcagta catcaatggg cgtggatagc ggtttgactc acggggattt     1740
ccaagtctcc accccattga cgtcaatggg agtttgtttt ggcaccaaaa tcaacgggac     1800
tttccaaaat gtcgtaacaa ctccgcccca ttgacgcaaa tgggcggtag gcgtgtacgg     1860
tgggaggtct atataagcag agctcgttta gtgaaccggg gtctctctgg ttagaccaga     1920
tctgagcctg ggagctctct ggctaactag ggaacccact gcttaagcct caataaagct     1980
tgccttgagt gcttcaagta gtgtgtgccc gtctgttgtg tgactctggt aactagagat     2040
ccctcagacc cttttagtca gtgtggaaaa tctctagcag tggcgcccga cagggacct      2100 gaaagcgaaa gggaaaccag agctctctcg acgcaggact cggcttgctg aagcgcgcac     2160
ggcaagaggc gaggggcggc gactggtgag tacgccaaaa attttgacta gcggaggcta     2220
gaaggagaga gatgggtgcg agagcgtcag tattaagcgg gggagaatta gatcgcgatg     2280
ggaaaaaatt cggttaaggc caggggggaaa gaaaaaatat aaattaaaac atatagtatg    2340
ggcaagcagg gagctagaac gattcgcagt taatcctggc ctgttagaaa catcagaagg     2400
ctgtagacaa atactgggac agctacaacc atcccttcag acaggatcag aagaacttag     2460
atcattatat aatacagtag caaccctcta ttgtgtgcat caaaggatag agataaaaga     2520
caccaaggaa gctttagaca agatagagga agagcaaaac aaaagtaaga ccaccgcaca     2580
gcaagcggcc gctgatcttc agacctggag gaggagatat gagggacaat tggagaagtg     2640
aattatataa atataaagta gtaaaaattg aaccattagg agtagcaccc accaaggcaa     2700
agagaagagt ggtgcagaga gaaaaaagag cagtgggaat aggagctttg ttccttgggt     2760
tcttgggagc agcaggaagc actatgggcg cagcctcaat gacgctgacg gtacaggcca     2820
gacaattatt gtctggtata gtgcagcagc agaacaattt gctgagggct attgaggcgc     2880
aacagcatct gttgcaactc acagtctggg gcatcaagca gctccaggca agaatcctgg     2940
ctgtggaaag atacctaaag gatcaacagc tcctggggat ttggggttgc tctggaaaac     3000
tcatttgcac cactgctgtg ccttggaatg ctagttggag taataaatct ctggaacaga    3060
```

```
tttggaatca cacgacctgg atggagtggg acagagaaat taacaattac acaagcttaa    3120
tacactcctt aattgaagaa tcgcaaaacc agcaagaaaa gaatgaacaa gaattattgg    3180
aattagataa atgggcaagt ttgtggaatt ggtttaacat aacaaattgg ctgtggtata    3240
taaaattatt cataatgata gtaggaggct tggtaggttt aagaatagtt tttgctgtac    3300
tttctatagt gaatagagtt aggcagggat attcaccatt atcgtttcag acccacctcc    3360
caaccccgag gggacccgac aggcccgaag gaatagaaga agaaggtgga gagagagaca    3420
gagacagatc cattcgatta gtgaacggat ctcgacggta tcggttaact tttaaaagaa    3480 aagggggggat tggggggtac agtgcagggg aaagaatagt agacataata gcaacagaca    3540
tacaaactaa agaattacaa aaacaaatta caaaaattca aaattttatc gataagcttg    3600
ggagttccgc gtgttggggg tggaccatcc tctaggtatt gaataagaaa aatgaagtta    3660
aggtggttga tggtaacact atgctaataa ctgcagagcc agaagcacca taagggacat    3720
gataagggag ccagcagacc tctgatctct tcctgaatgc taatcttaaa catcctgagg    3780
aagaatggga cttccatttg gggtgggcct atgatagggt aataagacag tagtgaatat    3840
caagctacaa aaagcccct ttcaaattct tctcagtcct aacttttcat actaagccca    3900
gtccttccaa agcagactgt gaaagagtga tagttccggg agactagcac tgcagattcc    3960
gggtcactgt gagtggggga ggcagggaag aagggctcac aggacagtca aaccatgccc    4020 cctgttttttc cttcttcaag tagacctcta taagacaaca gagacaacta aggctgagtg    4080
gccaggcgag gagaaaccat ctcgccgtaa aacatggaag gaacacttca ggggaaaggt    4140
ggtatctcta agcaagagaa ctgagtggag tcaaggctga gagatgcagg ataagcaaat    4200
gggtagtgaa aagacattca tgaggacagc taaaacaata agtaatgtaa aatacagcat    4260
agcaaaactt taacctccaa atcaagcctc tacttgaatc cttttctgag ggatgaataa    4320
ggcataggca tcaggggctg ttgccaatgt gcattagctg tttgcagcct caccttcttt    4380
catggagttt aagatatagt gtattttccc aaggtttgaa ctagctcttc atttctttat    4440 gtttttaaatg cactgacctc ccacattccc tttttagtaa aatattcaga aataatttaa    4500
atacatcatt gcaatgaaaa taaatgtttt ttattaggca gaatccagat gctcaaggcc    4560
cttcataata tcccccagtt tagtagttgg acttagggaa caaaggaacc tttaatagaa    4620
attggacagc aagaaagcga gcttagtgat acttgtgggc cagggcatta gccacaccag    4680
ccaccacttt ctgataggca gcctgcactg gtgggtgaa ttctttgcca aagtgatggg    4740
ccagcacaca gaccagcacg ttgcccagga gctgtgggag gaagataaga ggtatgaaca    4800
tgattagcaa aagggcctag cttggactca gaataatcca gccttatccc aaccataaaa    4860
taaaagcaga atggtagctg gattgtagct gctattagca atatgaaacc tcttacatca    4920
gttacaattt atatgcagaa atatttatat gcagaaatat tgctattgcc ttaacccaga    4980
aattatcact gttattcttt agaatggtgc aagaggcat gatacattgt atcattattg    5040
ccctgaaaga aagagattag ggaaagtatt agaaataaga taaacaaaaa agtatattaa    5100
aagaagaaag catttttttaa aattacaaat gcaaaattac cctgatttgg tcaatatgtg    5160
tacacatatt aaaacattac actttaaccc ataaatatgt ataatgatta tgtatcaatt    5220
aaaaataaaa gaaataaag tagggagatt atgaatatgc aaataagcac acatatattc    5280
caaatagtaa tgtactaggc agactgtgta aagttttttt ttaagttact taatgtatct    5340
cagagatatt tccttttgtt atacacaatg ttaaggcatt aagtataata gtaaaaattg    5400
```

-continued

```
cggagaagaa aaaaaaagaa agcaagaatt aaacaaaaga aaacaattgt tatgaacagc     5460
aaataaaaga aactaaaacg atcctgagac ttccacactg atgcaatcat tcgtctgttt     5520
cccattctaa actgtaccct gttacttctc cccttcctat gacatgaact taaccataga     5580
aaagaagggg aaagaaaaca tcaagggtcc catagactca ccctgaagtt ctcaggatcc     5640
acgtgcagct tgtcacagtg cagctcactc actgtggcaa aggtgccctt gaggttgtcc     5700
aggtgagcca ggccatcact aaaggcaccg agcactttct tgccatgagc cttcacctta     5760
gggttgccca taacagcatc aggagtggac agatccccaa aggactcaaa gaacctctgg     5820
gtccaagggt agaccaccag cagcctaagg gtgggaaaat agaccaatag gcagagagag     5880
tcagtgccta tcagaaaccc aagagtcttc tctgtctcca catgcccagt ttctattggt     5940
ctccttaaac ctgtcttgta accttgatac caacctgccc agggcctcac caccaacttc     6000
atccacgttc accttgcccc acagggcagt aacggcagac ttctcctcag gagtcaggtg     6060
caccatggtg tctgtttgag gttgctagtg aacacagttg tgtcagaagc aaatgtaagc     6120
aatagatggc tctgccctga cttttatgcc cagccctggc tcctgccctc cctgctcctg     6180
ggagtagatt ggccaaccct agggtgtggc tccacagggt gaggtctaag tgatgacagc     6240
cgtacctgtc cttggctctt ctggcactgg cttaggagtt ggacttcaaa ccctcagccc     6300
tccctctaag atatatctct tggccccata ccatcagtac aaattgctac taaaaacatc     6360
ctcctttgca agtgtattta cgtaatattt ggaatcacag cttggtaagc atattgaaga     6420
tcgttttccc aattttctta ttacacaaat aagaaattga tgcactaaaa gtggaagagt     6480
tttgtctacc ataattcagc tttgggtatat gtagatggat ctcttcctgc gtctccagaa     6540
tatgcaaaat acttacagga cagaatggat gaaaactcta cctcagttct aagcatatct     6600
tctccttatt tggattaaaa ccttctggta agaaaagaaa aaaatatat atatatatgt     6660 gtatatatac acacatacat atacatatat atgcattcat ttgttgttgt ttttcttaat     6720
ttgctcatgg tatatgtgta tatatatata tatatattca ggaaataata tattctagac     6780
tcaagcctca ttcagacact agtgtcacca gtctcctcat atacctattg tattttcttc     6840
ttcttgctgg tttagtcatg tttttctggga gcttaggggc ttattttatt ttgtttttgtt     6900 ttctaatcaa cagagatggg caaacccatt atttttttct ttagacttgg gatggtgata     6960
gctgggcagc gtcagaaact gtgtgtggat atagataaga gctcaggact atgctgagct     7020
gtgatgaggg aggggcctag ctaaaggcag tgagagtcag aatgctcctg ctattgcctt     7080
ctcagtcccc acgcttggtt tctacacaag tagatacata gaaaaggcta taggttagtg     7140
tttgagagtc ctgcatgatt agttgctcag aaatgcccga taaatatgtt atgtgtgttt     7200
atgtatatat atgtttttata tatatatata tgtgtgtgtg tgtgtgtgtg tgtgttgtgt     7260
ttacaaatat gtgattatca tcaaaacgtg agggctaaag tgaccagata acttgcaagt     7320
cctaggatac caggaaatct agaatatgtc acattctgtc tcaggcatcc attttctttta     7380 tgatgccgtt tgaggtggag ttttagtcag gtggtcagct tctcctttttt tttgccatct     7440 gccctgtaag catcctgctg gggacccaga taggagtcat cactctaggc tgagaacatc     7500
tgggcacaca ccctaagcct cagcatgact catcatgact cagcattgct gtgcttgagc     7560
cagaaggttt gcttagaagg ttacacagaa ccagaaggcg ggggtggggc actgaccccg     7620
acaggggcct ggccagaact gctcatgctt ggactatggg aggtcactaa tggagacaca     7680
cagaaatgta acaggaacta aggaaaaact gaagcttatt taatcagaga tgagatgctc     7740
gaagggatag agggagctga gcttgtaaaa agtatagtaa tcattcagca aatggttttg     7800
```

```
aagcacctgc tggatgctaa acactatttt cagtgcttga atcataaata agaataaaac    7860
atgtatctta ttccccacaa gagtccaagt aaaaaataac agttaattat aatgtgctct    7920
gtcccccagg ctggagtgca gtggcacgat ctcagctcac tgcaacctcc gcctcccggg    7980
ttcaagcaat tctcctgcct cagccaccct aatagctggg attacaggtg cacaccacca    8040
tgccaggcta attttttgtac tttttgtaga ggcagggtat caccatgttg tccaagatgg    8100
tcttgaactc ctgagctcca agcagtccac ccacctcagc ctcccaaagt gctatctgcg    8160
gccgcctatc tgtaccacta gtctcgagaa gctttcatta aaaaaagtct aaccagctgc    8220
attcgacttt gactgcagca gctggttaga aggttctact ggaggagggt cccagcccat    8280
tgctaaatta acatcaggct ctgagactgg cagtatatct ctaacagtgg ttgatgctat    8340
cttctggaac ttgcctgcta cattgagacc actgacccat acataggaag cccatagctc    8400
tgtcctgaac tgttaggcca ctggtccaga gagtgtgcat ctcctttgat cctcataata    8460
accctatgag atagacacaa ttattactct tactttatag atgatgatcc tgaaaacata    8520
ggagtcaagg cacttgcccc tagctggggg tataggggag cagtcccatg tagtagtaga    8580
atgaaaaatg ctgctatgct gtgcctcccc cacctttccc atgtctgccc tctactcatg    8640
gtctatctct cctggctcct gggagtcatg gactccaccc agcaccacca acctgaccta    8700
accacctatc tgagcctgcc agcctataac ccatctgggc cctgatagct ggtggccagc    8760
cctgacccca ccccacccte cctggaacct ctgatagaca catctggcac accagctcgc    8820
aaagtcaccg tgagggtctt gtgtttgctg agtcaaaatt ccttgaaatc caagtcctta    8880
gagactcctg ctcccaaatt tacagtcata gacttcttca tggctgtctc ctttatccac    8940
agaatgattc ctttgcttca ttgccccatc catctgatcc tcctcatcag tgcagcacag    9000
ggcccatgag cagtagctgc agagtctcac ataggtctgg cactgcctct gacatgtccg    9060
accttaggca aatgcttgac tcttctgagc tcagtcttgt catggcaaaa taaagataat    9120
aatagtgttt ttttatggag ttagcgtgag gatggaaaac aatagcaaaa ttgattagac    9180
tataaaaggt ctcaacaaat agtagtagat tttatcatcc attaatcctt ccctctcctc    9240
tcttactcat cccatcacgt atgcctctta attttccctt acctataata agagttattc    9300
ctcttattat attcttctta tagtgattct ggatattaaa gtgggaatga ggggcaggcc    9360
actaacgaag aagatgtttc tcaaagaagc cattctcccc acatagatca tctcagcagg    9420
gttcaggaag ataaaggagg atcaaggtcg aaggtaggaa ctaaggaaga acactgggac    9480
cggtactagt gcatgcaaat ctgacactca gtgggcctgg gtgaaggtga gaattttatt    9540
gctgaatgag agcctctggg gacatcttgc cagtcaatga gtctcaggtt caatttcctt    9600
ctcagtcttg gagtaacaga agctcatgca tttaataaac ggaaattttg tattgaaatg    9660
agagccattg gaaatcattt actccagact cctacttata aaaagagaaa ctgaggctca    9720
gagaagggtg gggactttct cagtatgaca tggaaatgat caggcttgga ttcaaagctc    9780
ctgactttct gtctagtgta tgtgcagtga gcccctttc ctctaactga aagaaggaaa    9840
aaaaaatgga acccaaaata ttctacatag tttccatgtc acagccaggg ctgggcagtc    9900
tcctgttatt tcttttaaaa taaatatatc atttaaatgc ataaataagc aaaccctgct    9960
cgggaatggg agggagagtc tctggagtcc accccttctc ggccctggct ctgcagatag   10020
tgctatcaaa gccctgacag agccctgccc attgctgggc cttggagtga gtcagcctag   10080
tagagaggca gggcaagcca tctcatagct gctgagtggg agagagaaaa gggctcattg   10140
```

-continued

```
tctataaact caggtcatgg ctattcttat tctcacacta agaaaaagaa tgagatgtct    10200
acatataccc tgcgtcccct cttgtgtact ggggtcccca agagctctct aaaagtgatg    10260
gcaaagtcat tgcgctagat gccatcccat ctattataaa cctgcatttg tctccacaca    10320
ccagtcatgg acaataaccc tcctcccagg tccacgtgct tgtctttgta taatactcaa    10380
gtaatttcgg aaaatgtatt ctttcaatct tgttctgtta ttcctgtttc aatggcttag    10440
tagaaaaagt acatacttgt tttcccataa attgacaata gacaatttca catcaatgtc    10500
tatatgggtc gttgtgtttg ctgtgtttgc aaaaactcac aataacttta tattgttact    10560
actctaagaa agttacaaca tggtgaatac aagagaaagc tattacaagt ccagaaaata    10620
aaagttatca tcttgaggcc tcctgcaggg tacctttaag accaatgact tacaaggcag    10680
ctgtagatct tagccacttt ttaaaagaaa agggggggact ggaagggcta attcactccc    10740
aacgaagaca agatctgctt tttgctgtgc gggccaggcc cccgagggcc ttatcggccc    10800
cagaggcgct tgctgtcggg ccgggcgctc ccggcacggg cgggcggagg ggtggcgccc    10860
gcctggggac cgcagattac aagagcacct cctcccccaa ccccaggagg ccccgctccc    10920
caggcctcgg ccggcgcgga cccctggttg ccccggactg ggtctctctg gttagaccag    10980
atctgagcct gggagctctc tggctaacta gggaacccac tgcttaagcc tcaataaagc    11040
ttgccttgag tgcttcaagt agtgtgtgcc cgtctgttgt gtgactctgg taactagaga    11100
tccctcagac cctttagtc agtgtggaaa atctctagca ggctagcaaa caaaagacgt    11160
acgagctatg ctttaattaa agctatgctg tcgacaatca acctctggat tacaaaattt    11220
gtgaaagatt gactggtatt cttaactatg ttgctccttt tacgctatgt ggatacgctg    11280
ctttaatgcc tttgtatcat gctattgctt cccgtatggc tttcattttc tcctccttgt    11340
ataaatcctg gttgctgtct ctttatgagg agttgtggcc cgttgtcagg caacgtggcg    11400
tggtgtgcac tgtgtttgct gacgcaaccc ccactggttg gggcattgcc accacctgtc    11460
agctcctttc cgggactttc gctttccccc tccctattgc cacggcggaa ctcatcgccg    11520
cctgccttgc ccgctgctgg acaggggctc ggctgttggg cactgacaat tccgtggtgt    11580
tgtcggggaa gctgacgtcc tttccatggc tgctcgcctg tgttgccacc tggattctgc    11640
gcgggacgtc cttctgctac gtcccttcgg ccctcaatcc agcggacctt ccttcccgcg    11700
gcctgctgcc ggctctgcgg cctcttccgc gtcttcgcct tcgccctcag acgagtcgga    11760
tctccctttg ggccgcctcc ccgcctggaa ttcgagctcg gtacctgatc agcctcgact    11820
gtgccttcta gttgccagcc atctgttgtt tgcccctccc ccgtgccttc cttgaccctg    11880
gaaggtgcca ctcccactgt cctttcctaa taaaatgagg aaattgcatc gcattgtctg    11940
agtaggtgtc attctattct ggggggtggg gtggggcagg acagcaaggg ggaggattgg    12000
gaagacaata gcaggcatgc tggggatgcg gtgggctcta tggcttctga ggaaagaacc    12060 agctgggggct cgagatccac tagttctagc ctcgaggcta gagcggccgc caccgcggta    12120
gtagttcatg tcatcttatt attcagtatt tataacttgc aaagaaatga atatcagaga    12180
gtgagaggaa cttgtttatt gcagcttata atggttacaa ataaagcaat agcatcacaa    12240
atttcacaaa taaagcattt ttttcactgc attctagttg tggtttgtcc aaactcatca    12300
atgtatctta tcatgtctgg ctctagctat cccgccccta actccgccca gttccgccca    12360
ttctccgccc catggctgac taatttttttt tatttatgca gaggccgagg ccgcctcggc    12420
ctctgagcta ttccagaagt agtgaggagg cttttttgga ggcctaggct tttgcgtcga    12480
gacgtaccca attcgcccta tagtgagtcg tattacgcgc gctcactggc cgtcgtttta    12540
```

-continued

```
caacgtcgtg actgggaaaa ccctggcgtt acccaactta atcgccttgc agcacatccc   12600
cctttcgcca gctggcgtaa tagcgaagag gcccgcaccg atcgcccttc ccaacagttg   12660
cgcagcctga atggcgaatg gcgcgacgcg ccctgtagcg gcgcattaag cgcggcgggt   12720
gtggtggtta cgcgcagcgt gaccgctaca cttgccagcg ccctagcgcc cgctcctttc   12780
gctttcttcc cttcctttct cgccacgttc gccggctttc cccgtcaagc tctaaatcgg   12840
gggctccctt tagggttccg atttagtgct ttacggcacc tcgaccccaa aaaacttgat   12900
tagggtgatg gttcacgtag tgggccatcg ccctgataga cggtttttcg ccctttgacg   12960
ttggagtcca cgttctttaa tagtggactc ttgttccaaa ctggacaac actcaaccct    13020 atctcggtct attcttttga tttataaggg attttgccga tttcggccta ttggttaaaa   13080
aatgagctga tttaacaaaa atttaacgcg aattttaaca aaatattaac gtttacaatt   13140
tcccaggtgg cacttttcgg ggaaatgtgc gcggaacccc tatttgttta ttttttctaaa  13200 tacattcaaa tatgtatccg ctcatgagac aataaccctg ataaatgctt caataatatt   13260
gaaaaaggaa gagtatgagt attcaacatt tccgtgtcgc ccttattccc ttttttgcgg   13320
cattttgcct tcctgttttt gctcacccag aaacgctggt gaaagtaaaa gatgctgaag   13380
atcagttggg tgcacgagtg ggttacatcg aactggatct caacagcggt aagatccttg   13440
agagttttcg ccccgaagaa cgttttccaa tgatgagcac ttttaaagtt ctgctatgtg   13500
gcgcggtatt atcccgtatt gacgccgggc aagagcaact cggtcgccgc atacactatt   13560
ctcagaatga cttggttgag tactcaccag tcacagaaaa gcatcttacg gatggcatga   13620
cagtaagaga attatgcagt gctgccataa ccatgagtga taacactgcg gccaacttac   13680
ttctgacaac gatcggagga ccgaaggagc taaccgcttt tttgcacaac atgggggatc   13740
atgtaactcg ccttgatcgt tgggaaccgg agctgaatga agccatacca aacgacgagc   13800
gtgacaccac gatgcctgta gcaatggcaa caacgttgcg caaactatta actggcgaac   13860
tacttactct agcttcccgg caacaattaa tagactggat ggaggcggat aaagttgcag   13920
gaccacttct gcgctcggcc cttccggctg gctggtttat tgctgataaa tctggagccg   13980
gtgagcgtgg gtctcgcggt atcattgcag cactggggcc agatggtaag ccctcccgta   14040
tcgtagttat ctacacgacg gggagtcagg caactatgga tgaacgaaat agacagatcg   14100
ctgagatagg tgcctcactg attaagcatt ggtaa                              14135
```

```
<210> SEQ ID NO 2
<211> LENGTH: 400
<212> TYPE: DNA
<213> ORGANISM: Artificial Sequence
<220> FEATURE:
<223> OTHER INFORMATION: shRNAmiR5mod within intron 1

<400> SEQUENCE: 2
ataatgatta tgtatcaatt aaaaataaaa gaaaataaag tagggagatt atgaatatgc     60
aaataagcac acatatattc caaatagtaa tgtactaggc agactgtgta aagttttttt    120
ttaagttact taatgtatct cagagatatt tccttttgtt atacacaatg ttaaggcatt    180
aagtataata gtaaaaattg cggagaagaa aaaaaaagaa agcaagaatt aaacaaaaga    240
aaacaattgt tatgaacagc aaataaaaga aactaaaacg atcctgagac ttccacactg    300
atgcaatcat tcgtctgttt cccattctaa actgtaccct gttacttctc cccttcctat    360
gacatgaact taaccataga aaagaagggg aaagaaaaca                          400
```

-continued

```
<210> SEQ ID NO 3
<211> LENGTH: 92
<212> TYPE: DNA
<213> ORGANISM: Artificial Sequence
<220> FEATURE:
<223> OTHER INFORMATION: coding region within the beta-globin gene

<400> SEQUENCE: 3
ctgcccaggg cctcaccacc aacttcatcc acgttcacct tgccccacag ggcagtaacg      60
gcagacttct cctcaggagt cagatgcacc at                                    92

<210> SEQ ID NO 4
<211> LENGTH: 92
<212> TYPE: DNA
<213> ORGANISM: Artificial Sequence
<220> FEATURE:
<223> OTHER INFORMATION: coding region within the beta-globin gene

<400> SEQUENCE: 4
ctgcccaggg cctcgccgcc gacttcatcc acgttcacct tgccccacag ggcagtaacg      60
gcagacttct cctcaggagt cagatgcacc at                                    92

<210> SEQ ID NO 5
<211> LENGTH: 100
<212> TYPE: DNA
<213> ORGANISM: Artificial Sequence
<220> FEATURE:
<223> OTHER INFORMATION: coding region within the beta-globin gene

<400> SEQUENCE: 5
actcagtgtg gcaaaggtgc ccttgaggtt gtccaggtga gccaggccat cactaaaggc      60
accgagcact ttcttgccat gagccttcac cttagggttg                           100

<210> SEQ ID NO 6
<211> LENGTH: 100
<212> TYPE: DNA
<213> ORGANISM: Artificial Sequence
<220> FEATURE:
<223> OTHER INFORMATION: coding region within the beta-globin gene

<400> SEQUENCE: 6
actcagtgtg gcaaaggtgc ccttgaggtt gtccaggtga gccaggccat cggagaaggc      60
accgagcact ttcttgccat gagccttcac cttagggttg                           100
```